United States Patent
Martin et al.

(10) Patent No.: US 7,977,489 B2
(45) Date of Patent: Jul. 12, 2011

(54) BENZYLTHIAZOLONE INHIBITORS OF ESTROGEN-RELATED RECEPTORS (ERR)

(75) Inventors: Richard Martin, San Diego, CA (US); Raju Mohan, Encinitas, CA (US); Brett B. Busch, San Diego, CA (US); Michael Charles Nyman, San Diego, CA (US); William C. Stevens, Jr., Escondido, CA (US)

(73) Assignee: Exelixis, Inc., South San Francisco, CA (US)

( * ) Notice: Subject to any disclaimer, the term of this patent is extended or adjusted under 35 U.S.C. 154(b) by 936 days.

(21) Appl. No.: 11/577,611

(22) PCT Filed: Oct. 21, 2005

(86) PCT No.: PCT/US2005/037853
§ 371 (c)(1),
(2), (4) Date: Apr. 20, 2007

(87) PCT Pub. No.: WO2006/047269
PCT Pub. Date: May 4, 2006

(65) Prior Publication Data
US 2009/0197870 A1  Aug. 6, 2009

Related U.S. Application Data

(60) Provisional application No. 60/621,296, filed on Oct. 22, 2004.

(51) Int. Cl.
*C07D 277/00* (2006.01)
(52) U.S. Cl. ...... 548/184; 514/369; 514/370; 514/236.8; 514/254.02; 514/227.8; 544/133; 544/369; 544/58.7
(58) Field of Classification Search .................. 514/369, 514/370, 236.8, 254.02; 544/133, 369; 548/184
See application file for complete search history.

(56) References Cited

U.S. PATENT DOCUMENTS 5,089,516 A  2/1992  Shiraishi et al.

OTHER PUBLICATIONS

Baihua Hu et al. (Bioorg. Med. Chem. Lett. 11 (2001) 981-984).*
Vippagunta et al, "Crystalline Solids", Advanced Drug Delivery Reviews, vol. 48, pp. 3-26 (2001).*
Gavezzotti, "Are Crystal Structures Predictable?", Accounts of Chemical Research, vol. 27, pp. 309-314 (1994).*
Wolff, Manfred E. "Burger's Medicinal Chemistry, 5ed, Part I", John Wiley & Sons, 1995, pp. 975-977.*
Banker et al, "Modern Pharmaceutics, 3ed.", Marcel Dekker, New York, 1996, pp. 451 and 596.*
Busch et al., "Identification of a selective inverse agonist for the orphan nuclear receptor estrogen-related receptor alpha", Journal of Medicinal Chemistry, 2004, 47(23), 5593-5596.

* cited by examiner

*Primary Examiner* — Yong Chu
*Assistant Examiner* — Valerie Rodriguez-Garcia
(74) *Attorney, Agent, or Firm* — McDonnell Boehnen Hulbert & Berghoff LLP

(57) ABSTRACT

Compounds of the following general structure for use in compositions and methods for modulating the activity of nuclear receptors are provided:

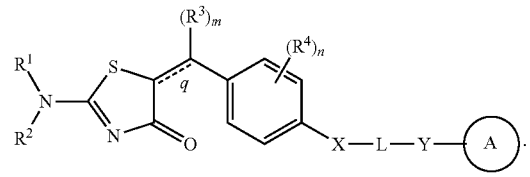

The compounds are useable in compositions and methods for modulating the estrogen related receptors and are agonists, partial agonists, antagonists. or inverse agonists of ERR or ERRα.

61 Claims, No Drawings

BENZYLTHIAZOLONE INHIBITORS OF ESTROGEN-RELATED RECEPTORS (ERR)

This application is a US national phase of international application PCT/US2005/037853 filed on Oct. 21, 2005, which claims priority to U.S. Provisional Patent Application Ser. No. 60/621,296 filed on Oct. 22, 2004, the disclosure of which is incorporated herein by reference.

FIELD OF THE INVENTION

Background of the Invention

Nuclear receptors are a superfamily of transcription factors that regulate a wide variety of cellular processes. Nuclear receptors share extensive homology at the amino acid and nucleotide sequence levels, the most highly conserved region being the DNA binding domain (DBD) which contains two zinc finger motifs and the next most highly conserved region being the ligand binding domain (LBD) which is responsible for ligand recognition, dimerization, coactivator interaction and ligand-dependent transcriptional activation. In general, these receptor proteins interact with recognition motifs in the promoter region of their target genes called the response element and modulate gene expression in response to ligands. Additionally, some orphan nuclear receptors may regulate target gene expression in the absence of a ligand.

Classic members of the nuclear receptor superfamily, such as the glucocorticoid receptor, mineralocorticoid receptor, estrogen receptor and the thyroid hormone receptor are receptors that were identified as a consequence of the initial discovery of their hormones. Orphan nuclear receptors, on the other hand, are those receptors that were identified by their structural similarities to the classic nuclear receptors, and which were not associated with a putative ligand at the time of their discovery. Examples of nuclear receptors that are referred to as "orphans" include the farnesoid X receptor (FXR (NR1H4)), liver X receptor (LXRα (NR1H2) and LXRβ (NR1H3)), estrogen related receptor (ERRα, ERRβ and ERRγ or NR3B1, NR3B2 and NR3B3, respectively).

ERR

The estrogen related receptor subfamily, currently comprised of three members, ERRα, ERRβ and ERRγ are close relatives of the estrogen receptor (ER), all sharing a high degree of homology in their DNA binding domains and ligand binding domains. It is now known that the ER and ERR subfamilies share some common promoter binding sites, a subset of common target genes, as well as some common co-regulator proteins and synthetic ligands.

ERRs bind to DNA as monomers or dimers to a variety of recognition motifs including the consensus ERR response element (ERRE) as well as to other elements including those recognized by ER (Sladek, R. et. al., Mol. Cell. Biol. 17, 5400-5409, 1997; Johnston, S. D. et. al., Mol. Endocrinol. 11, 342-352, 1997; Yang, N. et. al., J. Biol. Chem. 271, 5975-5804, 1996). Transcriptional crosstalk between the ER and ERR subfamilies therefore occurs at the level of competition for binding sites as well as for co-regulator proteins. Modulators of the ERR subfamily are therefore expected to act either by directly modulating the transcriptional effect of ERR or by indirect effects on ER signaling pathways, thereby having utility for both ERR and ER related diseases and disorders.

Transcriptional target genes common to both the ER and ERR subfamilies include those estrogen responsive genes such as the estrogen-inducible breast cancer marker gene, pS2 (Lu, D., et al., 2001, Cancer Res. 61: 6755-6761), aromatase cytochrome p450, a key enzyme involved in estrogen biosynthesis that is up-regulated in many estrogen-responsive breast cancers (Yang, N., et al. 1998, Cancer Research 58:5695-5700), lactoferrin, an immune response modulator (Yang, N., et al., 1996, J Biol. Chem. 271:5795-5804; Zhang, Z. and Teng, C. T., 2000, J Biol. Chem. 275:20837-20846) and osteopontin, an extracellular bone matrix molecule secreted by osteoblasts which is believed to play an important role in bone formation and remodeling (Vanacker J. M. et al., 1998, Cell Growth Differ 9:1007-1014).

Although it has been determined that 17-β estradiol and other natural ligands for ER are not ERR ligands, two synthetic ER ligands used clinically for the treatment of breast cancer, the synthetic estrogen diethylstilbestrol (DES) and 4-hydroxy tamoxifen (OHT), which belongs to a class of drugs called selective estrogen receptor modulators (SERMs), have been discovered to bind to the ERR subfamily with high affinity. DES acts as an inverse agonist to all three isoforms of ERR by interfering with coactivator interactions while OHT acts as an inverse agonist to ERRβ and ERRγ but not ERRα (Tremblay, G. B. et al, 2001, Genes Dev. 15:833-838; Tremblay, G. B. et al, 2001, Endocrinology 142(10): 4572-4575; Lu, D. et al., 2001, Cancer Res. 61:6755-6761; Coward, P. et. al., 2001, Proc. Natl. Acad. Sci. U.S.A. 98:8880-8884). This suggests that the ERR subfamily presents a new target for the development of new classes of drugs that are capable of selectively modulating a subset of estrogen's actions, without creating the same side effect profile of classical estrogen receptor modulators. The fact that well-established ER ligands such as DES and OHT are ERR ligands also suggests that classic ER modulating drugs may be exerting their effects at least in part through an ERR regulated pathway and that the modulation of ERR activity presents an alternative pathway for the treatment of diseases that were previously considered to be estrogen mediated.

In one embodiment, ERR modulators, including ERRα modulators, are expected to have therapeutic use in the treatment, prevention and diagnosis cancer, including breast cancer (See U.S. Patent Application No. 2003/0152959). ERRα modulators may also have therapeutic value as a general anti-cancer agent by inhibiting cell growth or tumor angiogenesis. ERRα modulators are also expected to have therapeutic value in the prevention and treatment of diseases of the bone and cartilage such as rheumatoid arthritis and osteoporosis (See U.S. Patent Application No. 2002/0187953). The functional interaction between ER and the proinflammatory transcription factor NF-kB suggests that ERR modulators may also play a role in preventing inflammatory diseases caused by the release of proinflammatory cytokines, such as rheumatoid arthritis or atherosclerosis. Because ERRs are highly expressed in the tissues of the central nervous system which are also estrogen target tissues, ERRα modulators are also contemplated for the prevention and treatment of psychoses and neurodegenerative or stress-related disorders such as Parkinson's disease, Alzheimer's disease, depression and anxiety.

ERRα has more recently been discovered to act as a metabolic regulator. ERRα regulates the expression of medium-chain acyl CoA dehydrogenase (MCAD), a key enzyme in fatty acid β oxidation (Vega, R. B. et al., 1997, J Biol Chem 272:31693-31699; Sladek, R. et. al., 1997, Mol. Cell. Biol. 17:5400-5409). It has also been discovered that the transcriptional coactivator PPARγ coactivator-1α (PGC-1α), which is believed to be a broad regulator of cellular energy metabolism, binds to ERRα and enhances the transactivation of the MCAD gene (Huss et al., 2002, J. Biol. Chem. 277:40265-40274). Since PGC-1α plays a key role in the upregulation of oxidative respiration and because there appears to be a correlation between reduced oxidative respiration and insulin resistance and/or type 2 diabetes mellitus (See Mootha et al., 2003, Nat Gen 34:267-273; Patti et al., 2003, Proc. Natl. Acad. Sci. U.S.A. 100:8466-8471), ERR modulators are expected to have therapeutic use in the treatment and prevention of diseases related to insulin resistance such as type 2 diabetes mellitus and the metabolic syndrome.

A study of the ERRα knockout mice model also suggests that ERRα plays a role as a key regulator of fat metabolism, including fatty acid synthesis, fatty acid oxidation, intestinal fat transfer and fat deposition in hepatic and adipocytic tissues. The knockout mice were found to have a lean phenotype with decreased white adipose tissue deposits and showing resistance to high-fat induced obesity. (Luo J. et al., 2003, Mol. Cell. Biol., 23:7947-7956; see also, US Patent Application No. 2003/0028910). Microarray analysis conducted on adipose tissues from the knockout mice showed altered regulation of several enzymes involved in lipid metabolism, including MCAD and fatty acid synthase. ERRα modulators are therefore contemplated for use in the treatment and prevention of diseases relating to fat metabolism, including hyperlipidemia, obesity and the metabolic syndrome.

Considering the wide range of activity of the nuclear hormone receptor ERRα, the compounds described herein which are capable of modulating ERRα activity, are useful for treating a range of disease states including cancer, diabetes, obesity, hyperlipidemia, arthritis, atherosclerosis, osteoporosis, anxiety, depression, Parkinson's disease and Alzheimer's disease.

SUMMARY OF THE INVENTION

Compounds for use in compositions and methods for modulating the activity of nuclear receptors are provided. In particular, compounds for use in compositions and methods for modulating the estrogen related receptors are provided. In one embodiment, the compounds provided herein are ERR modulators. In another embodiment, the compounds provided herein are agonists, partial agonists, antagonists or inverse agonists of ERR or ERRα. It is to be understood that partial agonists that, exhibit low efficacy are, in certain embodiments, antagonists.

In certain embodiments, the compounds of the invention, as described above in the Summary of the Invention, are compounds of formula (I):

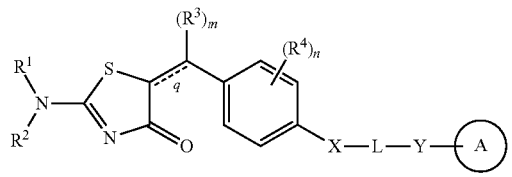

(I)

wherein.

bond q is a single bond or a double bond;

$R^1$ and $R^2$ are each independently optionally substituted alkyl, optionally substituted alkenyl, optionally substituted alkynyl, optionally substituted cycloalkyl, optionally substituted cycloalkylalkyl, optionally substituted heterocyclyl, optionally substituted heterocyclylalkyl, optionally substituted aryl, optionally substituted aralkyl, optionally substituted heteroaryl, optionally substituted heteroaralkyl, $-OR^{10}$ or $-C(O)R^{10}$; and $R^2$ can additionally be hydrogen; or $R^1$ and $R^2$, together with the nitrogen atom to which they are attached, form an optionally substituted heterocyclic or heteroaryl ring, wherein said optionally substituted heterocyclic or heteroaryl ring may be substituted with one to twelve substituents each independently selected from the group consisting of $R^5$ and $R^6$;

$R^3$ is hydrogen, halo or optionally substituted alkyl;

each $R^4$ is independently halo, cyano, nitro, optionally substituted alkyl, optionally substituted alkenyl, optionally substituted alkynyl, optionally substituted cycloalkyl, optionally substituted cycloalkylalkyl, optionally substituted heterocyclyl, optionally substituted heterocyclylalkyl, optionally substituted aryl, optionally substituted aralkyl, optionally substituted heteroaryl, optionally substituted heteroaralkyl, $-R^9-N(R^{21})(R^{22})$, $-R^9-OR^{20}$, $-R^9-SR^{20}$, $-R^9-C(O)R^{20}$, $-R^9-C(O)OR^{20}$, $-R^9-C(O)N(R^{21})(R^{22})$, $-R^9-OC(O)R^{20}$, $-R^9-N(R^8)C(O)R^{20}$, $-R^9-OC(O)OR^{20}$, $-R^9-OC(O)N(R^{21})(R^{22})$, $-R^9-N(R^8)C(O)OR^{20}$, $-R^9-N(R^8)C(O)N(R^{21})(R^{22})$, $-R^9-N(R^8)S(O)_2R^{23}$, $-R^9-S(O)_tR^{23}$ (where t is an integer from 1 to 2) or $-R^9-S(O)_2N(R^{21})(R^{22})$;

each $R^5$ and $R^6$ are independently selected from the group consisting of halo, cyano, nitro, optionally substituted alkyl, optionally substituted alkenyl, optionally substituted alkynyl, optionally substituted cycloalkyl, optionally substituted cycloalkylalkyl, optionally substituted heterocyclyl, optionally substituted heterocyclylalkyl, optionally substituted aryl, optionally substituted aralkyl, optionally substituted heteroaryl or optionally substituted heteroaralkyl and $-R^9-OR^{10}$, $-R^9-N(R^{11})(R^{12})$, $-R^9-SR^{10}$, $-R^9-C(J)R^{10}$, $-R^9-C(J)OR^{10}$, $-R^9-C(J)N(R^{11})(R^{12})$, $-R^9-N(R^8)C(O)OR^{10}$, $-R^9-OC(O)N(R^{11})(R^{12})$, $R^9-N(R^8)C(J)N(R^{11})(R^{12})$ and $-R^9-S(O)_tR^{13}$ (where t is an integer from 1 to 2); or $R^5$ and $R^6$, together with the carbon to which they are attached, form oxo, thioxo, cycloalkyl, heterocyclyl, ethylene dioxy or propylene dioxy;

m is an integer from 1 to 2;

n is an integer from 0 to 4;

X is $-O-$, $NR^8-$, $-S(O)_u-$ (where u is an integer from 0 to 2) or a direct bond;

L is an optionally substituted branched or linear alkylene chain having 1 to 6 carbons, an optionally substituted cycloalkyl having 3 to 6 carbons, an optionally substituted branched or linear alkenylene chain having 2 to 6 carbons and 1 to 2 double bonds or an optionally substituted branched or linear alkynylene chain having 2 to 6 carbons and 1 to 2-triple bonds;

Y is $-O-$, $-NR^8-$, $-S(O)_u-$ (where u is an integer from 0 to 2) or a direct bond;

A is an optionally substituted aryl or optionally substituted heteroaryl ring, wherein said optionally substituted aryl or said optionally substituted heteroaryl ring may be substituted with one to five substituents each independently selected from the group consisting of halo, nitro, cyano, optionally substituted alkyl, optionally substituted alkenyl, optionally substituted alkynyl, optionally substituted cycloalkyl, optionally substituted cycloalkylalkyl, optionally substituted heterocyclyl, optionally substituted heterocyclylalkyl, optionally substituted aryl, optionally substituted aralkyl, optionally substituted heteroaryl, optionally substituted heteroaralkyl, $-R^9-N(R^{31})(R^{32})$, $-R^9-OR^{30}$, $-R^9-SR^{30}$, $-R^9-C(J)R^{30}$, $-R^9-C(J)OR^{30}$, $-R^9-C(J)N(R^{31})(R^{32})$, $-R^9-OC(J)R^{30}$, $-R^9-N(R^8)C(J)R^3$, $-R^9-OC(J)OR^{30}$, —$R^9$—$OC(J)N(R^{31})(R^{32})$, —$R^9$—$N(R^8)C(J)OR^{30}$, —$R^9$—$N(R^8)C(J)N(R^{31})(R^{32})$, —$R^9$—$N(R^8)S(O)_2R^{33}$, —$R^9$—$S(O)_tR^{33}$ (where t is an integer from 1 to 2) and —$R^9$—$S(O)_2N(R^{31})(R^{32})$;

each $R^8$ is independently hydrogen or optionally substituted alkyl;

each $R^9$ is independently a direct bond or optionally substituted alkylene;

each $R^{10}$, $R^{20}$ and $R^{30}$ are each independently selected from the group consisting of hydrogen, optionally substituted alkyl, optionally substituted alkenyl, optionally substituted alkynyl, optionally substituted cycloalkyl, optionally substituted cycloalkylalkyl, optionally substituted heterocyclyl, optionally substituted heterocyclylalkyl, optionally substituted aryl, optionally substituted aralkyl, optionally substituted heteroaryl and optionally substituted heteroaralkyl;

$R^{11}$, $R^{12}$, $R^{21}$, $R^{22}$, $R^{31}$ and $R^{32}$ are selected from any combination of (i), (ii), (iii) or (iv):

(i) $R^{11}$, $R^{12}$, $R^{21}$, $R^{22}$, $R^{31}$ and $R^{32}$ are each independently selected from the group consisting of hydrogen, optionally substituted alkyl, optionally substituted alkenyl, optionally substituted alkynyl, optionally substituted cycloalkyl, optionally substituted cycloalkylalkyl, optionally substituted heterocyclyl, optionally substituted heterocyclylalkyl, optionally substituted aryl, optionally substituted aralkyl, optionally substituted heteroaryl and optionally substituted heteroaralkyl, (ii) $R^{11}$ and $R^{12}$, together with the nitrogen atom to which they are attached, form an optionally substituted heterocyclyl or optionally substituted heteroaryl, (iii) $R^{21}$ and $R^{22}$, together with the nitrogen atom to which they are attached, form an optionally substituted heterocyclyl or an optionally substituted heteroaryl, (iv) $R^{31}$ and $R^{32}$, together with the nitrogen atom to which they are attached, form an optionally substituted heterocyclyl or an optionally substituted heteroaryl, $R^{13}$, $R^{23}$ and $R^{33}$ are each independently selected from the group consisting of optionally substituted alkyl, optionally substituted alkenyl, optionally substituted alkynyl, optionally substituted cycloalkyl, optionally substituted cycloalkylalkyl, optionally substituted heterocyclyl, optionally substituted heterocyclylalkyl, optionally substituted aryl, optionally substituted aralkyl, optionally substituted heteroaryl and optionally substituted heteroaralkyl; and J is O, S or $NR^{14}$;

wherein $R^{14}$ is selected from the group consisting of hydrogen, optionally substituted alkyl, or optionally substituted cycloalkyl;

as a single isomer, a mixture of stereoisomers, or as a racemic mixture of isomers; as any tautomeric form; as a solvate or polymorph; or as a prodrug or metabolite; or as a pharmaceutically acceptable salt thereof;

wherein when $R^1$ and $R^2$, together with the nitrogen atom to which they are attached, form unsubstituted pyrrolidine, piperidine optionally substituted with methyl or with ethyl ester, or piperazine N-substituted with methyl, ethyl, cyanoethyl, substituted or unsubstituted phenyl, naphthyl, benzyl or acetyl, X is —O—, L is methylene, Y is a direct bond and A is an optionally substituted phenyl ring, then A is substituted with at least one substituent, but cannot be singly substituted with 4-nitro or 2-fluoro;

and that when $R^1$ and $R^2$, together with the nitrogen atom to which they are attached, form unsubstituted piperidine, unsubstituted azepine, unsubstituted morpholine or morpholine substituted with two methyl groups, n is 0 or 1, $R^4$ is methoxy or halo, X is —O—, L is methylene, Y is a direct bond and A is a phenyl ring, then A is substituted with at least one substituent, but cannot be singly substituted with 4-bromo, 4-chloro or 4-nitro;

and that when $R^1$ is unsubstituted phenyl optionally substituted with one to three substituents selected from methyl, ethyl, trifluoromethyl, halo, hydroxy, methoxy, ethoxy, nitro and sulfonamide, $R^2$ is hydrogen, X is —O—, L is methylene, Y is a direct bond and A is a phenyl ring, then A is not substituted with bromo, chloro or nitro;

and that when $R^1$ is benzyl substituted with two methyl groups, $R^4$ is alkoxy, halo or nitro, X is —O—, L is methylene, Y is a direct bond and A is a phenyl ring or an unsubstituted naphthyl ring, then A must be substituted with at least one substituent, but cannot be singly substituted with 2-chloro, 4-bromo, 4-fluoro, 4-nitro or doubly substituted with 2,4-dichloro;

and that when $R^1$ is —$C(O)R^{10}$ where $R^{10}$ is methyl or ethyl, $R^2$ is hydrogen, X is —O—, L is methylene, Y is a direct bond and A is a phenyl ring, then A is substituted with at least one haloalkyl group;

and that when $R^1$ and $R^2$, together with the nitrogen atom to which they are attached, form unsubstituted piperidine or piperidine substituted with methyl or benzyl, piperazine N-substituted with ethyl or hydroxyethyl, unsubstituted pyrrolidine, unsubstituted azepine or unsubstituted morpholine; X, L and Y are direct bonds and A is a phenyl ring, then A must be substituted with at least one substituent.

DETAILED DESCRIPTION OF THE INVENTION

A. Definitions

Unless defined otherwise, all technical and scientific terms used herein have the same meaning as is commonly understood by one of ordinary skill in the art to which this invention belongs. All patents, applications, published applications and other publications are incorporated by reference in their entirety. In the event that there are a plurality of definitions for a term herein, those in this section prevail unless stated otherwise.

"Alkyl" refers to a straight or branched hydrocarbon chain radical consisting solely of carbon and hydrogen atoms, containing no unsaturation, having from one to ten carbon atoms, and which is attached to the rest of the molecule by a single bond, e.g., methyl, ethyl, n-propyl, 1-methylethyl (iso-propyl), n-butyl, n-pentyl, 1,1-dimethylethyl (t-butyl), and the like.

"Alkenyl" refers to a straight or branched hydrocarbon chain radical consisting solely of carbon and hydrogen atoms, containing at least one double bond, having from two to ten carbon atoms, and which is attached to the rest of the molecule by a single bond or a double bond, e.g., ethenyl, prop-1-enyl, but-1-enyl, pent-1-enyl, penta-1,4-dienyl, and the like.

"Alkynyl" refers to a straight or branched hydrocarbon chain radical consisting solely of carbon and hydrogen atoms, containing at least one triple bond, having from two to ten carbon atoms, and which is attached to the rest of the molecule by a single bond or a triple bond, e.g., ethynyl, prop-1-ynyl, but-1-ynyl, pent-1-ynyl, pent-3-ynyl and the like.

"Alkylene" and "alkylene chain" refer to a straight or branched divalent hydrocarbon chain consisting solely of carbon and hydrogen, containing no unsaturation and having from one to eight carbon atoms, e.g., methylene, ethylene, propylene, n-butylene and the like. The alkylene chain may be attached to the rest of the molecule through any two carbons within the chain.

"Alkenylene" or "alkenylene chain" refers to a straight or branched chain unsaturated divalent radical consisting solely of carbon and hydrogen atoms, having from one to eight carbon atoms, wherein the unsaturation is present only as double bonds and wherein a double bond can exist between the first carbon of the chain and the rest of the molecule, e.g., ethenylene, prop-1-enylene, but-2-enylene and the like. The alkenylene chain may be attached to the rest of the molecule through any two carbons within the chain.

"Alkoxy" refers to the radical having the formula —OR wherein R is alkyl or haloalkyl. An "optionally substituted alkoxy" refers to the radical having the formula —OR wherein R is an optionally substituted alkyl as defined herein.

"Alkynylene" or "alkynylene chain" refers to a straight or branched chain unsaturated divalent radical consisting solely of carbon and hydrogen atoms, having from one to eight carbon atoms, wherein the unsaturation is present only as triple bonds and wherein a triple bond can exist between the first carbon of the chain and the rest of the molecule, e.g., ethynylene, prop-1-ynylene, but-2-ynylene, pent-1-ynylene, pent-3-ynylene and the like. The alkynylene chain may be attached to the rest of the molecule through any two carbons within the chain.

As used herein, "amidino" refers to a radical having the formula —C(=NR)N(R')R" where R, R' and R" are each independently hydrogen or alkyl.

"Amino" refers to a radical having the formula —NR'R" wherein R' and R" are each independently hydrogen, alkyl, alkenyl, haloalkyl or haloalkenyl. An "optionally substituted amino" refers to a radical having the formula —NR'R" wherein one or both of R' and R" are optionally substituted alkyl or optionally substituted alkenyl as defined herein.

"Aryl" refers to a radical of carbocylic ring system wherein at least one of the rings is aromatic. The aryl may be fully aromatic, examples of which are phenyl, naphthyl, anthracenyl, acenaphthylenyl, azulenyl, fluorenyl, indenyl and pyrenyl. The aryl may also contain an aromatic ring in combination with a non-aromatic ring, examples of which are acenaphene, indene, and fluorene.

"Aralkyl" refers to a radical of the formula —$R_aR_b$ where $R_a$ is an alkyl radical as defined above, substituted by $R_b$, an aryl radical, as defined above, one example of which is benzyl. Both the alkyl and aryl radicals may be optionally substituted as defined herein. "Optionally substituted aralkyl" refers to a radical of the formula —$R_aR_b$ where $R^a$ is an alkyl radical as defined above, substituted by $R_b$, an optionally substituted aryl radical, as defined herein.

"Atherosclerosis" refers to process whereby atherosclerotic plaques form within the inner lining of the artery wall leading to atherosclerotic cardiovascular diseases. Atherosclerotic cardiovascular diseases can be recognized and understood by physicians practicing in the relevant fields of medicine, and include without limitation, restenosis, coronary heart disease (also known as coronary artery heart disease or ischemic heart disease), cerebrovascular disease including ischemic stroke, multi-infarct dementia, and peripheral vessel disease, including intermittent claudication, and erectile dysfunction.

"Cycloalkyl" refers to a stable monovalent monocyclic or bicyclic hydrocarbon radical consisting solely of carbon and hydrogen atoms, having from three to ten carbon atoms, and which is saturated and attached to the rest of the molecule by a single bond, e.g., cyclopropyl, cyclobutyl, cyclopentyl, cyclohexyl, decalinyl, norbornane, norbornene, adamantyl, bicyclo[2.2.2]octane and the like.

"Cycloalkylalkyl" refers to a radical of the formula —$R_aR_d$ where $R_a$ is an alkyl radical as defined above and $R_d$ is a cycloalkyl radical as defined above. The alkyl radical and the cylcoalkyl radical may be optionally substituted as defined herein. "Optionally substituted cycloalkylalkyl" refers to a radical of the formula —$R_aR_d$ where $R_a$ is an alkyl radical as defined above and $R_d$ is an optionally substituted cycloalkyl radical as defined herein.

"Dyslipidemia" refers to abnormal levels of lipoproteins in blood plasma including both depressed and/or elevated levels of lipoproteins (e.g., elevated levels of Low Density Lipoprotein, (LDL), Very Low Density Lipoprotein (VLDL) and depressed levels of High Density Lipoprotein (HDL).

"$EC_{50}$" refers to a dosage, concentration or amount of a particular test compound that elicits a dose-dependent response at 50% of maximal expression of a particular response that is induced, provoked or potentiated by the particular test compound.

"ERRα-related disease, condition or disorder" and the like refers to a condition in which ERRα activity is implicated in the disease, condition or disorder, or in which the modulation of ERRα activity is useful or effective in the treatment of the disease, condition or disorder. In some instances, inappropriate ERRα activity may be only one of multiple underlying causes of the disease, condition or disorder, for example, when ER activity is also implicated in the disease, condition or disorder.

ERR related diseases, conditions or disorders, or more particularly, ERRα related diseases, conditions or disorders include (a) metabolic disorders such as hyperglycemia, insulin insensitivity, diabetes, obesity, hyperlipidemia, hypercholesterolemia, hyperlipoproteinemia, hypertriglyceridemia, dyslipidemia, hypertension, hyperinsulinemia, hyperuricemia, or a combination thereof to make up the disease state known as the metabolic syndrome (also called "Syndrome X"), (b) diseases, conditions or disorders relating to proliferative cell activity such as cancer, including breast cancer, (c) diseases, conditions or disorders relating to the bone or cartilage, including osteoporosis, osteoarthritis and rheumatoid arthritis, (d) diseases, conditions or disorders relating to the inflammatory response, including rheumatoid arthritis and atherosclerosis, and (e) psychoses and neurodegenerative or stress-related disorders including Parkinson's disease, Alzheimer's disease, depression, anxiety and chemical dependency.

"ERR modulator" or "a compound capable of modulating ERR activity" refer to those compounds which modulate the activity of nuclear receptors of the ERR subfamily, in the manner of an agonist, partial agonist, inverse agonist or antagonist.

As used herein, "ERR α" refers to all mammalian forms of such receptor including, for example, alternative splice isoforms and naturally occurring isoforms. Representative ERRα species include, without limitation the rat (Genbank Accession XM_215174), mouse (Genbank Accession NM_007953), and human (GenBank Accession NM_004451, XM_048286) forms of the receptor.

As used herein, "ERR β" refers to all mammalian forms of such receptor including, for example, alternative splice isoforms and naturally occurring isoforms. Representative ERR β species include, without limitation the rat (GenBank Accession NM_011934), mouse (Genbank Accession NM_011934), and human (GenBank Accession NM_00452) forms of the receptor.

As used herein, "ERR γ" refers to all mammalian forms of such receptor including, for example, alternative splice isoforms and naturally occurring isoforms. Representative ERR γ species include, without limitation the rat (GenBank Accession XM_341170), mouse (Genbank Accession NM_011935), and human (GenBank Accession NM_001438) forms of the receptor.

As used herein "ERR" "ERRs" or "ERR subfamily" refers to all species of ERRα, ERRβ and ERRγ.

As used herein, "guanidino" refers to a radical having the formula —N(R)C(=NR')NR"R''' wherein R, R', R" and R''' are each independently hydrogen or alkyl.

"Halo", "halogen" or "halide" refers to F, Cl, Br or I.

"Haloalkyl" refers to an alkyl group in which one or more of the hydrogen atoms are replaced by halogen. Such groups include, but are not limited to, chloromethyl, trifluoromethyl and 1-chloro-2-fluoroethyl.

"Haloalkenyl" refers to an alkenyl group in which one or more of the hydrogen atoms are replaced by halogen. Such groups include, but are not limited to, 1-chloro-2-fluoroethenyl.

"Heterocyclyl" refers to a stable 3- to 15-membered ring radical which consists of carbon atoms and from one to five heteroatoms selected from the group consisting of nitrogen, oxygen and sulfur. For purposes of this invention, the heterocyclic ring system radical may be a monocyclic, bicyclic or tricyclic ring or tetracyclic ring system, which may include fused or bridged ring systems; and the nitrogen or sulfur atoms in the heterocyclic ring system radical may be optionally oxidized; the nitrogen atom may be optionally quaternized; and the heterocyclyl radical may be partially or fully saturated or aromatic. The heterocyclic ring system may be attached to the main structure at any heteroatom or carbon atom which results in the creation of a stable compound. Examples of such heterocyclic radicals include, but are not limited to: acridinyl, azepinyl, benzimidazolyl, benzindolyl, benzisoxazinyl, benzo[4,6]imidazo[1,2-a]pyridinyl, benzodioxanyl, benzodioxolyl, benzofuranonyl, benzofuranyl, benzonaphthofuranyl, benzopyranonyl, benzopyranyl, benzotetrahydrofuranyl, benzotetrahydrothienyl, benzothiadiazolyl, benzothiazolyl, benzothiophenyl, benzotriazolyl, benzothiopyranyl, benzoxazinyl, benzoxazolyl, benzothiazolyl, β-carbolinyl, carbazolyl, chromanyl, chromonyl, cinnolinyl, coumarinyl, decahydroisoquinolinyl, dibenzofuranyl, dihydrobenzisothiazinyl, dihydrobenzisoxazinyl, dihydrofuryl, dihydropyranyl, dioxolanyl, dihydropyrazinyl, dihydropyridinyl, dihydropyrazolyl, dihydropyrimidinyl, dihydropyrrolyl, dioxolanyl, 1,4-dithianyl, furanonyl, furanyl, imidazolidinyl, imidazolinyl, imidazolyl, imidazopyridinyl, imidazothiazolyl, indazolyl, indolinyl, indolizinyl, indolyl, isobenzotetrahydrofuranyl, isobenzotetrahydrothienyl, isobenzothienyl, isochromanyl, isocoumarinyl, isoindolinyl, isoindolyl, isoquinolinyl, isothiazolidinyl, isothiazolyl, isoxazolidinyl, isoxazolyl, methylenedioxypiperidinyl, morpholinyl, naphthyridinyl, octahydroindolyl, octahydroisoindolyl, octahydroquinolinyl, octahydroisoquinolinyl, oxadiazolyl, oxazolidinonyl, oxazolidinyl, oxazolopyridinyl, oxazolyl, oxiranyl, perimidinyl, phenanthridinyl, phenathrolinyl, phenarsazinyl, phenazinyl, phenothiazinyl, phenoxazinyl, phthalazinyl, piperazinyl, piperidinyl, 4-piperidonyl, pteridinyl, purinyl, pyrazinyl, pyrazolidinyl, pyrazolyl, pyridazinyl, pyridinyl, pyridopyridinyl, pyrimidinyl, pyrrolidinyl, pyrrolinyl, pyrrolyl, quinazolinyl, quinolinyl, quinoxalinyl, quinuclidinyl, tetrahydrofuryl, tetrahydrofuranyl, tetrahydroisoquinolinyl, tetrahydropyranyl, tetrahydrothienyl, tetrazolyl, thiadiazolopyrimidinyl, thiadiazolyl, thiamorpholinyl, thiazolidinyl, thiazolyl, thiophenyl, triazinyl, triazolyl and 1,3,5-trithianyl.

"Heteroaralkyl" refers to a radical of the formula —$R_aR_f$ where $R_a$ is an alkyl radical as defined above and $R_f$ is a heteroaryl radical as defined herein. The alkyl radical and the heteroaryl radical may be optionally substituted as defined herein. "Optionally substituted heteroaralkyl" refers to a radical of the formula —$R_aR_f$ where $R_a$ is an alkyl radical as defined above and $R_f$ is an optionally substituted heteroaryl radical as defined herein.

"Heteroaryl" refers to a heterocyclyl radical as defined above which is aromatic. The heteroaryl radical may be attached to the main structure at any heteroatom or carbon atom which results in the creation of a stable compound. Examples of such heteroaryl radicals include, but are not limited to: acridinyl, benzimidazolyl, benzindolyl, benzisoxazinyl, benzo[4,6]imidazo-[1,2-a]pyridinyl, benzofuranyl, benzonaphthofuranyl, benzothiadiazolyl, benzothiazolyl, benzothiophenyl, benzotriazolyl, benzothiopyranyl, benzoxazinyl, benzoxazolyl, benzothiazolyl, β-carbolinyl, carbazolyl, cinnolinyl, dibenzofuranyl, furanyl, imidazolyl, imidazopyridinyl, imidazothiazolyl, indazolyl, indolizinyl, indolyl, isobenzothienyl, isoindolinyl, isoquinolinyl, isothiazolidinyl, isothiazolyl, naphthyridinyl, octahydroindolyl, octahydroisoindolyl, octahydroisoquinolin-1(2H)-yl, octahydroquinolin-1(2H)-yl, oxazolidinonyl, oxazolidinyl, oxazolopyridinyl, oxazolyl, oxiranyl, perimidinyl, phenanthridinyl, phenathrolinyl, phenarsazinyl, phenazinyl, phenothiazinyl, phenoxazinyl, phthalazinyl, pteridinyl, purinyl, pyrazinyl, pyrazolyl, pyridazinyl, pyridinyl, pyridopyridinyl, pyrimidinyl, pyrrolyl, quinazolinyl, quinolinyl, quinoxalinyl, tetrazolyl, thiadiazolyl, thiazolyl, thiophenyl, triazinyl, triazolyl, and xanthenyl.

"Heterocyclylalkyl" refers to a radical of the formula —$R_aR_e$ wherein $R_a$ is an alkyl radical as defined above and $R_e$ is a heterocyclyl radical as defined herein. The alkyl radical and the heterocyclyl radical may be optionally substituted as defined herein. "Optionally substituted heterocyclylalkyl" refers to a radical of the formula —$R_aR_e$ wherein $R_a$ is an alkyl radical as defined above and $R_e$ is an optionally substituted heterocyclyl radical as defined herein.

"Hyperlipidemia" refers to the presence of an abnormally elevated level of lipids in the blood. Hyperlipidemia can appear in at least three forms: (1) hypercholesterolemia, i.e., an elevated LDL cholesterol level above normal (2) hypertriglyceridemia, i.e., an elevated triglyceride level above normal and (3) combined hyperlipidemia, i.e., a combination of hypercholesterolemia and hypertriglyceridemia.

"$IC_{50}$" refers to an amount, concentration or dosage of a particular test compound that achieves a 50% inhibition of a maximal response, such as modulation of nuclear receptor. In the case of the constitutively active receptors ERRα, ERRβ, or ERRγ $IC_{50}$ refers to an amount, concentration or dosage of a particular test compound that achieves a 50% inhibition of constitutive receptor activity, in an assay that measures such response.

"Imino" refers to =NR, wherein R is hydrogen or alkyl.

"Optionally substituted alkyl", "optionally substituted alkenyl" and "optionally substituted alkynyl" refer to alkyl radicals, alkenyl radicals and alkynyl radicals, respectively, that may be optionally substituted by one or more substituents independently selected from the group consisting of nitro, halo, azido, cyano, cycloalkyl, aryl, heteroaryl, heterocyclyl, —$OR^x$, —$N(R^y)(R^z)$, —$SR^x$, —C(j)$R^x$, —C(J)$OR^x$, —C(J)N($R^y$)($R^z$), —C(J)$SR^x$, —S(O)$R^x$ (where t is 1 or 2), —Si($R^w$)$_3$, —N($R^x$)S(O)$_2R^w$ and —S(O)$_2$N($R^y$)($R^z$), wherein:

$R^x$ is hydrogen, alkyl, alkenyl, alkynyl, cycloalkyl, cycloalkylalkyl, heterocyclyl, heterocyclylalkyl, aryl, aralkyl, heteroaryl, or heteroaralkyl;

$R^y$ and $R^z$ are each independently hydrogen, alkyl, alkenyl, alkynyl, cycloalkyl, cycloalkylalkyl, heterocyclyl, heterocyclylalkyl, aryl, aralkyl, heteroaryl, or heteroaralkyl; or $R^y$ and $R^z$, together with the nitrogen atom to which they are attached, form a heterocyclyl or heteroaryl;

$R^w$ is alkyl, alkenyl, alkynyl, cycloalkyl, cycloalkylalkyl, heterocyclyl, heterocyclylalkyl, aryl, aralkyl, heteroaryl, or heteroaralkyl;

$R^v$ is alkyl, alkenyl, alkynyl, cycloalkyl, cycloalkylalkyl, heterocyclyl, heterocyclylalkyl, aryl, aralkyl, heteroaryl, heteroaralkyl, hydroxy, —$OR^x$ or —$N(R^y)(R^z)$; and J is O, $NR^x$ or S.

Unless stated otherwise specifically in the specification, it is understood that the substitution can occur on any carbon of the alkyl, alkenyl or alkynyl group. "Optionally substituted aryl", "optionally substituted cycloalkyl", "optionally substituted heteroaryl" and "optionally substituted heterocyclyl" refers to aryl, cycloalkyl, heterocyclyl and heteroaryl radicals, respectively, that are optionally substituted by one or more substituents selected from the group consisting of nitro, halo, haloalkyl, haloalkoxy, haloalkenyl, azido, cyano, oxo, dioxo, thioxo, alkyl optionally substituted with halo, cyano, hydroxy, optionally substituted alkoxy, optionally substituted amino or optionally substituted sulfide, alkenyl, alkynyl, cycloalkyl, cycloalkylalkyl, heterocyclyl, heterocyclylalkyl, aryl, aralkyl, heteroaryl, heteroaralkyl, —$R_u$—$OR^x$, —$R^u$—$N(R^y)(R^z)$, —$R^u$—$SR^x$, —$R^u$—$C(J)R^x$, —$R^u$—$C(J)OR^x$, —$R^U$—$C(J)N(R^y)(R^z)$, —$R^u$—$C(J)SR^x$, —$R^u$—$S(O)_tR^x$ (where t is 1 or 2), —$R^u$—$Si(R^w)_3$, —$R^uN(R^x)S(O)_2R^w$, —$RUN(R^y)C(J)(O)R^w$, $R^uN(R^y)C(J)R^w$, —$R^U$—$S(O)_2N(R^y)(R^z)$ and —$R^u$—$C(J)N(R^x)S(O)_2R^5$, wherein:

each $R^u$ is independently alkylene or a direct bond;

each $R^v$ is independently alkyl, alkenyl, alkynyl, cycloalkyl, cycloalkylalkyl, heterocyclyl, heterocyclylalkyl, aryl, aralkyl, heteroaryl, heteroaralkyl, hydroxy, —$OR^x$ or —$N(R^y)(R^z)$;

$R^w$ is alkyl, alkenyl, alkynyl, cycloalkyl, cycloalkylalkyl, heterocyclyl, heterocyclylalkyl, aryl, aralkyl, heteroaryl, or heteroaralkyl;

each $R^x$ is independently hydrogen, alkyl, alkenyl, alkynyl, cycloalkyl, cycloalkylalkyl, heterocyclyl, heterocyclylalkyl, aryl, aralkyl, heteroaryl, or heteroaralkyl;

$R^y$ and $R^z$ are each independently hydrogen, alkyl, alkenyl, alkynyl, cycloalkyl, cycloalkylalkyl, heterocyclyl, heterocyclylalkyl, aryl, aralkyl, heteroaryl, or heteroaralkyl;

$R^y$ and $R^z$, together with the nitrogen atom to which they are attached, form a heterocyclyl or heteroaryl; and J is O, $NR^x$ or S.

"Oxo" refers to =O.

"Thioxo" refers to =S.

"Pharmaceutically acceptable derivatives" of a compound include salts, esters, enol ethers, enol esters, acetals, ketals, orthoesters, hemiacetals, hemiketals, acids, bases, solvates, hydrates or prodrugs thereof. Such derivatives may be readily prepared by those of skill in this art using known methods for such derivatization. The compounds produced may be administered to animals or humans without substantial toxic effects and either are pharmaceutically active or are prodrugs. Pharmaceutically acceptable salts include, but are not limited to, amine salts, such as but not limited to N,N'-dibenzylethylenediamine, chloroprocaine, choline, ammonia, diethanolamine and other hydroxyalkylamines, ethylenediamine, N-methylglucamine, procaine, N-benzylphenethylamine, 1-para-chlorobenzyl-2-pyrrolidin-1'-ylmethyl-benzimidazole, diethylamine and other alkylamines, piperazine and tris(hydroxymethyl)aminomethane; alkali metal salts, such as but not limited to lithium, potassium and sodium; alkali earth metal salts, such as but not limited to barium, calcium and magnesium; transition metal salts, such as but not limited to zinc; and other metal salts, such as but not limited to sodium hydrogen phosphate and disodium phosphate; and also including, but not limited to, salts of mineral acids, such as but not limited to hydrochlorides and sulfates; and salts of organic acids, such as but not limited to acetates, lactates, malates, tartrates, citrates, ascorbates, succinates, butyrates, valerates and fumarates. Pharmaceutically acceptable esters include, but are not limited to, alkyl, alkenyl, alkynyl, aryl, heteroaryl, aralkyl, heteroaralkyl, cycloalkyl and heterocyclyl esters of acidic groups, including, but not limited to, carboxylic acids, phosphoric acids, phosphinic acids, sulfonic acids, sulfinic acids and boronic acids. Pharmaceutically acceptable enol ethers include, but are not limited to, derivatives of formula C=C(OR) where R is hydrogen, alkyl, alkenyl, alkynyl, aryl, heteroaryl, aralkyl, heteroaralkyl, cycloalkyl or heterocyclyl. Pharmaceutically acceptable enol esters include, but are not limited to, derivatives of formula C=C(OC(O)R) where R is hydrogen, alkyl, alkenyl, alkynyl, aryl, heteroaryl, aralkyl, heteroaralkyl, cycloalkyl or heterocyclyl. Pharmaceutically acceptable solvates and hydrates are complexes of a compound with one or more solvent or water molecules, or 1 to about 100, or 1 to about 10, or one to about 2, 3 or 4, solvent or water molecules.

"Polymorph" refers to the different crystal forms of a compound, resulting from the possibility of at least two different arrangements of the molecules of the compound in the solid state. Polymorphs of a given compound will be different in crystal structure but identical in liquid or vapor states. Different polymorphic forms of a given substance may differ from each other with respect to one or more physical properties, such as solubility and dissociation, true density, crystal shape, compaction behavior, flow properties, and/or solid state stability.

"Prodrug" is a compound that, upon in vivo administration, is metabolized by one or more steps or processes or otherwise converted to the biologically, pharmaceutically or therapeutically active form of the compound. To produce a prodrug, the pharmaceutically active compound is modified such that the active compound will be regenerated by metabolic processes. The prodrug may be designed to alter the metabolic stability or the transport characteristics of a drug, to mask side effects or toxicity, to improve the flavor of a drug or to alter other characteristics or properties of a drug. By virtue of knowledge of pharmacodynamic processes and drug metabolism in vivo, those of skill in this art, once a pharmaceutically active compound is known, can design prodrugs of the compound (see, e.g., Nogrady (1985) *Medicinal Chemistry A Biochemical Approach*, Oxford University Press, New York, pages 388-392).

"Sulfide" refers to the radical having the formula —SR wherein R is an alkyl or haloalkyl group. An "optionally substituted sulfide" refers to the radical having the formula —SR wherein R is an optionally substituted alkyl as defined herein.

Unless specifically stated otherwise, where a compound may assume alternative tautomeric, regioisomeric and/or stereoisomeric forms, all alternative isomers are intended to be encompassed within the scope of the present invention. For example, where a compound is described as having one of two tautomeric forms sketched below, it is also intended that the other tautomer be encompassed within the scope of the present invention.

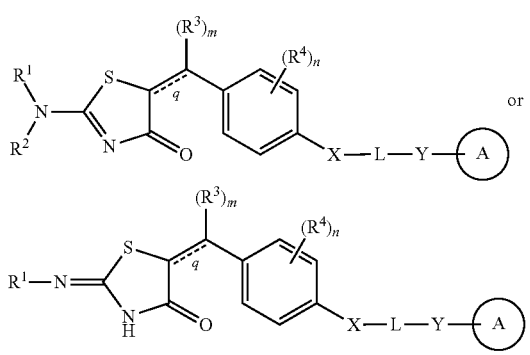

When the compounds described herein contain olefinic double bonds, it is intended that the compound descriptions include both E and Z geometric isomers. For example, where a compound is described as having one of the E and Z configurations sketched below, it is intended that both configurations be included in the scope of the present invention.

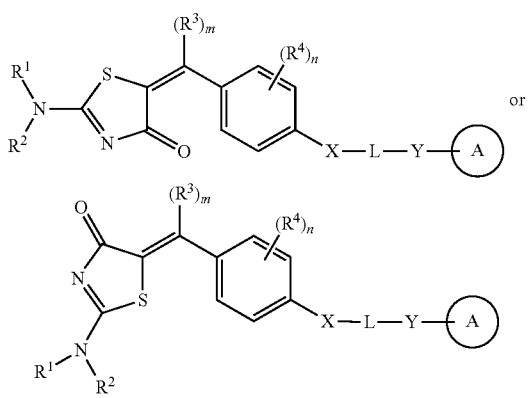

In some instances, a crossed double bond as shown below is used to depict a compound as having either an E or Z configuration.

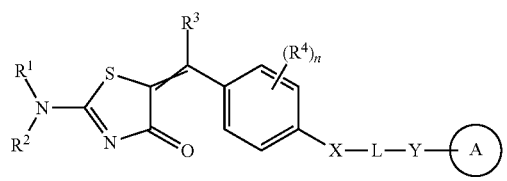

It is to be understood that the compounds provided herein may contain chiral centers. Such chiral centers may be of either the (R) or (S) configuration, or may be a mixture thereof. Thus, the compounds provided herein may be enantiomerically pure, or be stereoisomeric or diastereomeric mixtures. It is to be understood that the chiral centers of the compounds provided herein may undergo epimerization in vivo. As such, one of skill in the art will recognize that administration of a compound in its (R) form is equivalent, for compounds that undergo epimerization in vivo, to administration of the compound in its (S) form.

Optically active (+) and (−), (R)- and (S)-isomers may be prepared using chiral synthons or chiral reagents, or resolved using conventional techniques, such as reverse phase HPLC.

As used herein, substantially pure means sufficiently homogeneous to appear free of readily detectable impurities as determined by standard methods of analysis, such as thin layer chromatography (TLC), gel electrophoresis, high performance liquid chromatography (HPLC) and mass spectrometry (MS), used by those of skill in the art to assess such purity, or sufficiently pure such that further purification would not detectably alter the physical and chemical properties, such as enzymatic and biological activities, of the substance. Methods for purification of the compounds to produce substantially chemically pure compounds are known to those of skill in the art. A substantially chemically pure compound may, however, be a mixture of stereoisomers. In such instances, further purification might increase the specific activity of the compound.

Where the number of any given substituent is not specified (e.g., haloalkyl), there may be one or more substituents present. For example, "haloalkyl" may include one or more of the same or different halogens.

As used herein, the abbreviations for any protective groups, amino acids and other compounds, are, unless indicated otherwise, in accord with their common usage, recognized abbreviations, or the IUPAC-IUB Commission on Biochemical Nomenclature (see, *Biochem.* 1972, 11:942-944).

| | |
|---|---|
| AcOH | acetic acid |
| anhyd | anhydrous |
| CDI | 1,1'-carbonyldiimidazole |
| CHCl$_3$ | chloroform |
| conc | concentrated |
| DCM | dichloromethane |
| DOTAP | N-[1-(2,3-Dioleoyloxy)]-N,N,N-trimethylammonium propane methylsulfate |
| DMF | N,N-dimethylformamide |
| DMSO | dimethyl sulfoxide |
| Et$_2$O | diethyl ether |
| EtOAc | ethyl acetate |
| EtOH | ethanol (100%) |
| Hex | hexanes |
| MeOH | methanol |
| NH$_4$OAc | ammonium acetate |
| Pd/C | palladium on activated carbon |
| Pd[PPH$_3$]$_4$ | Tetrakis(triphenylphosphine)palladium (0) |
| satd | saturated |
| TBAF | Tetrabutylammonium fluoride |
| TBSCl | Tert-butyldimethylsilyl chloride |
| TEA | triethylamine |
| THF | tetrahydrofuran |

B. Preparation of the Compounds

Starting materials in the synthesis examples provided herein are either available from commercial sources or via literature procedures. All commercially available compounds and solvents were used without further purification unless otherwise indicated. Flash chromatography was performed using Merck Silica Gel 60 (230-400 mesh) following standard protocol (Still et al., (1978) *J. Org. Chem.* 43, 2923). Proton ($^1$H) nuclear magnetic resonance (NMR) spectra were recorded on a Bruker Avance 400 MHz NMR spectrometer. CDCl$_3$ (99.8% D, Cambridge Isotope Laboratories) or DMSO-d$_6$ (99.9% D, Cambridge Isotope Laboratories) was used in all experiments as indicated. Significant peaks are tabulated and typically include: number of protons, and multiplicity (s, singlet; d, doublet; t, triplet; q, quartet; m, multiplet; br s, broad singlet). Chemical shifts are reported as parts per million (δ) relative to the middle point of the solvent peak. Low-resolution mass spectra (MS) were obtained as electrospray ionization (ESI) mass spectra, which were recorded on a Perkin-Elmer SCIEX HPLC/MS instrument using reverse-phase conditions (acetonitrile/water, 0.05% trifluoroacetic acid). The infrared (IR) spectra were acquired on an Avatar 360 FT-IR instrument. The samples were prepared as KBr pellets, and the absorptions are reported as wavenumbers (v) in the unit of reciprocal centimeters (cm$^{-1}$).

Starting materials in the synthesis examples provided herein are either available from commercial sources or via literature procedures. All commercially available compounds and solvents were used without further purification unless otherwise indicated. Purification of synthetic products was typically carried out by flash chromatography using Merck Silica Gel 60 (230-400 mesh) following standard protocol (Still et al. *J. Org. Chem.* (1978) 43, 2923). In certain cases, compounds were purified by reverse-phase preparative HPLC using a mobile phase consisting of water and acetonitrile. Proton ($^1$H) nuclear magnetic resonance (NMR) spectra were recorded on a Bruker Avance 400 MHz NMR spectrometer. CDCl$_3$ (99.8% D, Cambridge Isotope Laboratories) or DMSO-d$_6$ (99.9% D, Cambridge Isotope Laboratories) was used in all experiments as indicated. Significant peaks are tabulated and typically include: number of protons, and multiplicity (s, singlet; d, doublet; t, triplet; q, quartet; m, multiplet; br s, broad singlet). Chemical shifts are reported as parts per million (δ) relative to the middle point of the solvent peak. Low-resolution mass spectra (MS) were obtained as electrospray ionization (ESI) mass spectra, which were recorded on a Perkin-Elmer SCIEX HPLC/MS instrument using reverse-phase conditions (acetonitrile/water, 0.05% trifluoroacetic acid).

It is understood that in the following description, combinations of substituents and/or variables of the depicted formulae are permissible only if such contributions result in stable compounds. It will also be appreciated by those skilled in the art that in the process described below the functional groups of intermediate compounds may need to be protected by suitable protecting groups. Such functional groups include hydroxyl, amino, mercapto and carboxylic acid. Protecting groups may be added or removed in accordance with standard techniques, which are well known to those skilled in the art and as described herein. The use of protecting groups is described in detail in Green, T. W. and P. G. M. Wutz, *Protective Groups in Organic Synthesis* (1991), 2nd Ed., Wiley-Interscience. Also it will be apparent to one skilled in the art that many of the products could exist as one or more geometrical isomers, that is E/Z isomers, enantiomers, diastereomers, or tautomers.

The following illustrations depict general preparations of compounds claimed herein and consist of reactions typically known to one skilled in the art of chemical synthesis. The substituents R$^1$-R$^{33}$, X, L, Y, A and J are as defined above in the Summary of the Invention, and in selected examples, defined below in the text or in the synthesis Schemes. One of ordinary skill in the art could easily ascertain which choices for each substituent are possible for the reaction conditions of each Scheme. Moreover, the substituents are selected from components as indicated in the specification heretofore, and may be attached to starting materials, intermediates, and/or final products according to methods known to those of ordinary skill in the art. The synthetic process used to prepare compounds defined in the Summary of Invention will be described first from the general perspective of Formula I, such as in Scheme 1. Specific reaction examples and reagents will be given in order to highlight the synthetic methods relevant to compounds in the Claim Formulae.

In general, compounds of Formula I, such as 2-aminothiazol-4-one (3) in Scheme 1, can be synthesized from methylthiol intermediate (2) by reaction of an amine (R$^1$R$^2$NH) in a solvent inert to the reaction, for example, in an organic solvent such as acetonitrile, THF, or benzene (Omar, M. T.; Sherif, F. A. *J. Prakt. Chem.* (1980), 322(5), 835; Unangst, P. C.; Connor, D. T. et al. *J. Med. Chem.* (1994), 37, 322). The amine as the starting material is a compound that is either commercially available or obtainable in a synthetic manner known to those of ordinary skill in the art. The amine reagent can be a primary or secondary, acyclic amine, such as ethylamine or dimethylamine respectively. Also, the amine can be secondary cyclic amines such as morpholine and piperidine. Methylthiol intermediate (2) can be prepared from aryl-methylidine-2-thioxo-thiazolidin-4-one (1) by reaction with iodomethane. The methylation reaction can be carried out in an organic solvent such as 1,4-dioxane, acetonitrile, or ethanol in the presence of an amine bases such as triethylamine or diisopropylethylamine. The two-step reaction sequence shown in Scheme 1 can be carried out when bond q is either a single or double carbon-carbon bond.

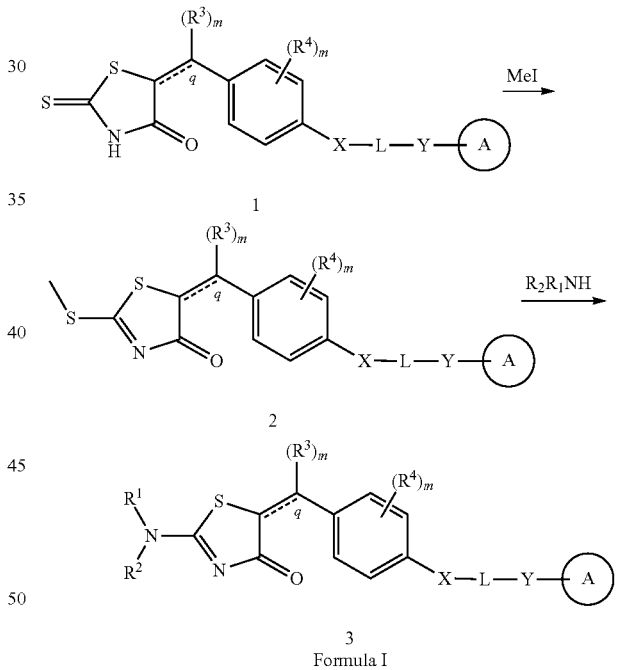

Scheme 1

In general, the aryl-methylidene-2-thioxo-thiazolidin-4-one (1a, b) can be synthesized by the combination of aromatic aldehyde (4a) (R$^3$=H) or ketone (4b) R$^3$=alkyl, aryl) with 2-thioxo-thiazolidin-4-one (rhodanine) (5) under conventional Knoevenagel condensation reaction conditions (Tietz, L. F et al. *Comp. Org. Syn.* (1991) 2, 341; Watson, B. T. et al. *Tetrahedron Lett.* (1998) 39, 6087; Brown, Newbold *J Chem Soc.* (1952), 4397). The condensation can be carried out by heating the reactants in the presence of an acidic or basic catalyst, in an organic solvent such as dimethylformamide or benzene. The condensation of aromatic aldehydes, such as (4a), with rhodanine (5) can be efficiently carried out in refluxing acetic acid in the presence of several equivalents of sodium acetate. When the Knoevenagel reaction involves condensation of arylketone (4b) with rhodanine (5), neutral reaction conditions using ammonium acetate in refluxing toluene affords products of structure (1). The condensation reaction between reactants (4a, b) and (5) may produce a single geometrical isomer or a mixture of E and Z isomers around the carbon-carbon double bond. The compounds described in the Summary of Invention are typically isolated as a single geometrical isomer following work up from the reaction mixture and purification by flash chromatography (Tanikana, R.; Nonya, N. et al. *Bull. Chem. Soc. Jpn.* (1988), 61, 3211).

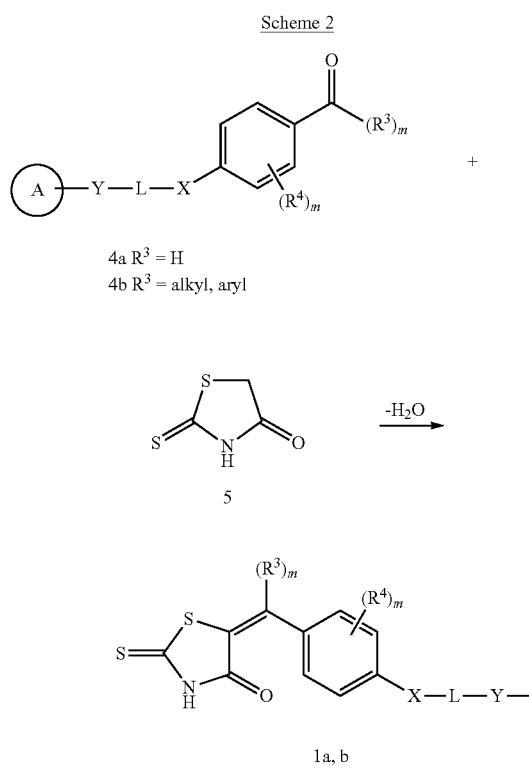

The double bond in aryl-methylidene-2-thioxo-thiazolidin-4-one (1a, b) can be converted to the single bond analogs (1c, d) upon treatment with various hydride reducing agents (Scheme 3). For example, the double bond can be reduced by treatment with either NaBH$_3$CN in acetic acid or in a mixture of LiBH$_4$ and pyridine/THF (Giles, R. G.; Lewis, N. J.; Quick, J. K.; et al. *Tetrahedron* (2000), 56, 4531). The reduction of the double bond using borohydride reductants produces a racemic mixture of compounds. Stereoselective reduction methods that provide a high enantiomeric excess of one stereoisomer can be used to produce chiral compounds (1c, d). Catalytic hydrogenation conditions can also convert the double bond on compounds (1a, b) to a single bond (March, J *Advanced Organic Chemistry*, 4$^{th}$ Ed.; John Wiley: New York (1992); Carruthers, W. *Some Modern Methods of Organic Synthesis*, 3$^{rd}$ Ed.; Cambridge University Press: Cambridge, UK (1986)).

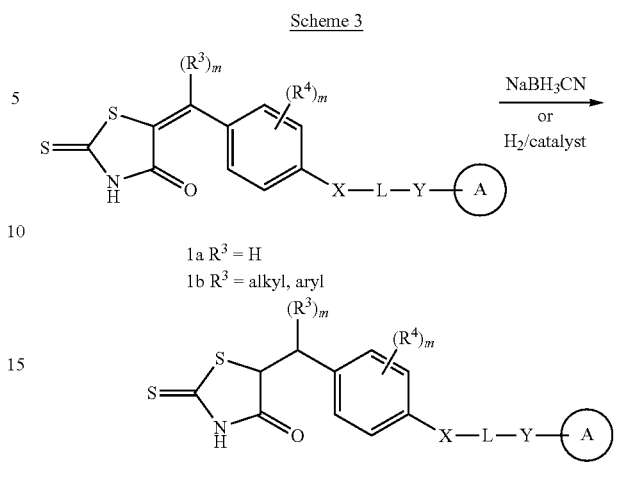

In general, the substituted aromatic aldehydes (4a) and ketones (4b) are obtainable either from commercial sources or synthesized using methodology known to those of ordinary skill in the art (Carey, F. A., Sundberg, R. J. *Advanced Organic Chemistry*, 3$^{rd}$ Ed.; Plenum: New York (1993)). The group R$^4$ on benzaldehyde (4a) can be widely varied in order to prepare the type of analogs described in the Examples. Several selected examples of the synthesis of substituted aromatic aldehydes (4c-f), relevant to the Invention, are shown in Scheme 4, eqs 1-5. When the aromatic aldehyde precursor (6) contains a hydroxyl, amino, or thiol group (X=O, NH, S), alkylation with a wide range of alkyl halides (7) can provide a facile method for installing substituent groups on the aromatic ring to yield (4a) (eq 1). By example, benzaldehyde (4c), an important intermediate for compounds in this patent, was synthesized by common alkylation methods using vanillin (8) and 2-trifluoromethylbenzyl bromide (9) in a heated mixture of potassium carbonate and acetonitrile (eq 2). For the purpose of attaching an alkyl ether linkage to the aromatic aldehyde, such as with compound (4d), the reaction sequence shown in equations 3 of Scheme 4 can be used. By example, aromatic aldehyde precursor (10) can be alkylated using 2-bromoethanol (11) to prepare ethylene ether compound (12). Compound (12) can be reacted under Mitsunobu coupling conditions with phenol (13) to synthesize aromatic aldehyde (4d) (eq 3). Transition metal mediated coupling reactions, such as the copper based reaction with arylboronic acid and phenol (10) shown in equation 4 of Scheme 4, can be employed for the installation of ring substituents to prepare phenyloxy-benzaldehyde (4e).

Moreover, installation of the aromatic ring substituents can proceed via various aromatic substitution reactions and metal mediated coupling reactions using aldehyde intermediates that do not contain a hydroxyl group. As a result, aromatic aldehyde precursor (6) may also posses X=alkylene and aryl. For example, Suzuki coupling reactions mediated with Pd catalyst can be used to prepare biphenyl aldehyde (4f) from bromoaromatic aldehyde (14) and phenylboronic acid. It is understood that the synthetic transformations summarized in Scheme 4 can also be used not only to prepare aldehyde or ketone intermediates but also can be applied later in the synthesis, such as after the Knoevenagel condensation and 2-amino-thiazol-4-one formation.

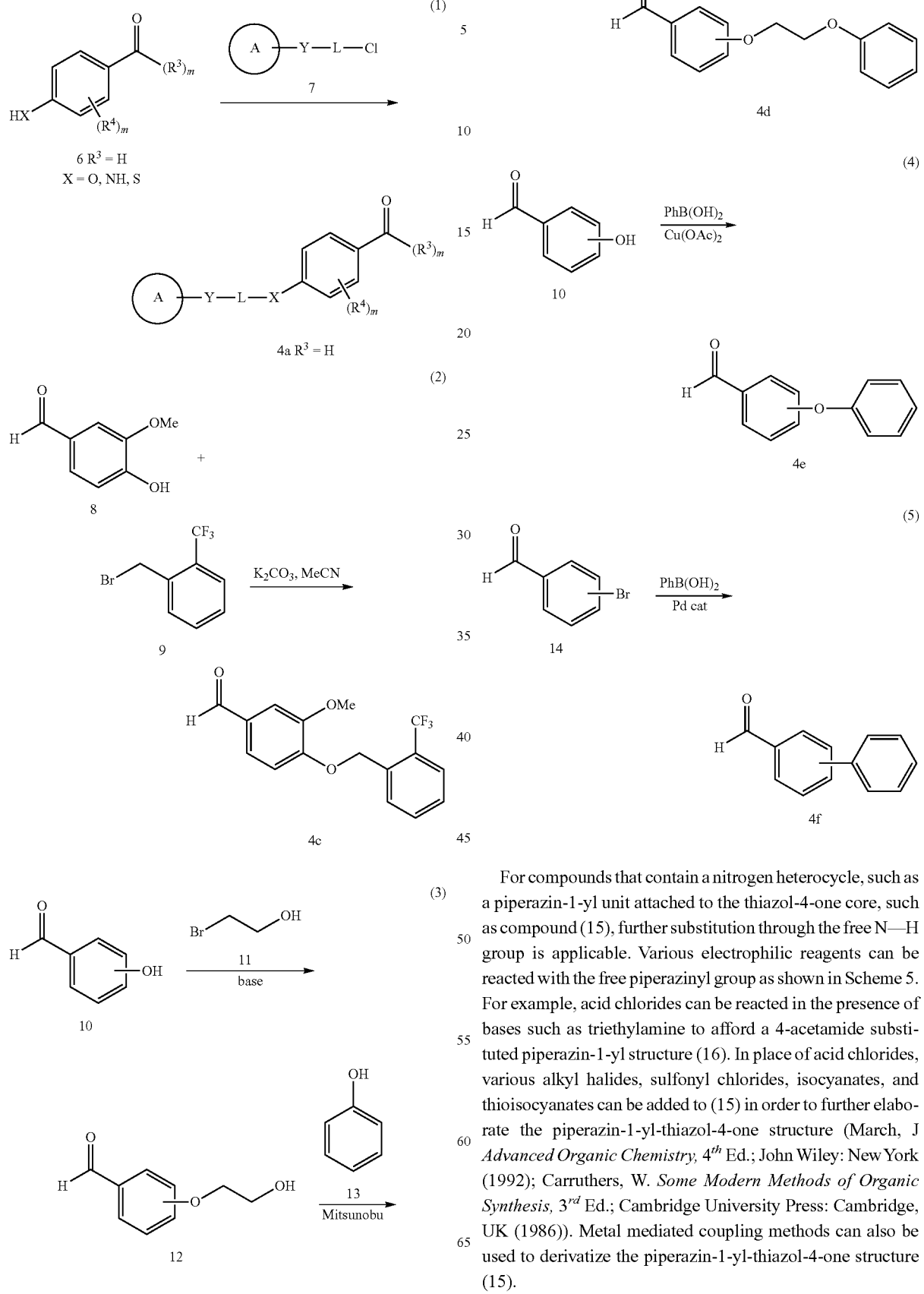

For compounds that contain a nitrogen heterocycle, such as a piperazin-1-yl unit attached to the thiazol-4-one core, such as compound (15), further substitution through the free N—H group is applicable. Various electrophilic reagents can be reacted with the free piperazinyl group as shown in Scheme 5. For example, acid chlorides can be reacted in the presence of bases such as triethylamine to afford a 4-acetamide substituted piperazin-1-yl structure (16). In place of acid chlorides, various alkyl halides, sulfonyl chlorides, isocyanates, and thioisocyanates can be added to (15) in order to further elaborate the piperazin-1-yl-thiazol-4-one structure (March, J *Advanced Organic Chemistry*, 4$^{th}$ Ed.; John Wiley: New York (1992); Carruthers, W. *Some Modern Methods of Organic Synthesis*, 3$^{rd}$ Ed.; Cambridge University Press: Cambridge, UK (1986)). Metal mediated coupling methods can also be used to derivatize the piperazin-1-yl-thiazol-4-one structure (15).

Scheme 5

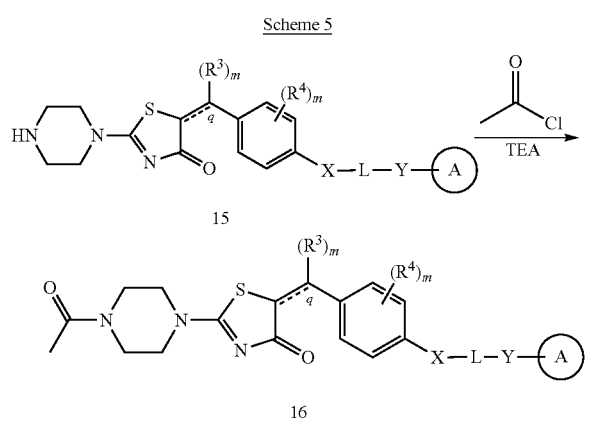

C. Evaluation of the Activity of the Compounds

Those of skill in the art recognize that various methods may be used to characterize and profile the activity of the claimed compounds and compositions. Suitable cell based assays for assaying the activity of the claimed compounds include, but are not limited to, the co-transfection assay, the use of GAL4 chimeras and protein-protein interaction assays (see, for example, Lehmann. et al., *J. Biol. Chem.* 1997, 272(6):3137-3140).

In addition many biochemical screening formats exist for screening compound activities to identify high affinity ligands which include, but are not limited to, direct binding assays, ELISAs, fluorescence polarization assays, fluorescence resonance energy transfer assays (FRET) and Time resolved FRET based coactivator recruitment assays (see, generally, Glickman et al., *J. Biomolecular Screening,* 2002, 7(1):3-10).

Binding assays employing fluorescent materials that are well known in the art are described in, e.g., Lakowicz, J. R., *Principles of Fluorescence Spectroscopy*, New York: Plenum Press (1983); Herman, B., Resonance energy transfer microscopy, in: *Fluorescence Microscopy of Living Cells in Culture, Part B, Methods in Cell Biology*, vol. 30, ed. Taylor, D. L. & Wang, Y. L., San Diego: Academic Press (1989), pp. 219-243; Turro, N. J., *Modern Molecular Photochemistry*, Menlo Park: Benjamin/Cummings Publishing Col, Inc. (1978), pp. 296-361.

For example, fluorescence polarization assays are based on the principle that a fluorescent-labeled compound that is excited by plane polarized light will emit fluorescent light displaying a degree of polarization that is related to the bulk and rotational mobility of the fluorescent-labeled compound. A fluorescent compound that is bound to a protein or receptor will be relatively immobile and have a slow rate of rotation. When the immobilized fluorescent compound is excited by plane-polarized light, it will emit polarized fluorescent light in the same plane since the molecule will have rotated very little during its brief period of fluorescence. An unbound fluorescent compound, on the other hand, will exhibit greater rotational mobility and hence emit less polarized or depolarized light during its period of fluorescence when excited by plane-polarized light. A high fluorescence polarization value therefore indicates that a fluorescent labeled compound has high affinity for a receptor molecule.

If a fluorescent labeled ligand is available, fluorescence polarization assays provide a way of detecting binding of compounds to the nuclear receptor of interest by measuring changes in fluorescence polarization from competitive displacement or binding inhibition of a trace amount of the label ligand by the compound. Alternatively, a fluorescent labeled coactivator peptide to the nuclear receptor of interest having the receptor binding motif LXXLL can be used to detect ligand binding to the nuclear receptor of interest.

FRET-based assays rely upon the fact that energy transfer from a labeled donor molecule to a labeled acceptor molecule only occurs when donor and acceptor are in close proximity. Typically, FRET is exploited to measure the ligand dependent interaction of a co-activator peptide with a nuclear receptor in order to characterize the agonist or antagonist activity of the compounds disclosed herein. The assay in such a case involves the use of a recombinant epitope, or affinity tagged nuclear receptor ligand binding domain (LBD) fusion protein and a synthetic biotinylated peptide derived from the receptor interacting domain (–LXXLL motif) of a co-activator peptide such as the steroid receptor coactivator 1 (SRC-1), TIF2, DRIP1 or AIB1. Typically the tagged-LBD is labeled with a lanthanide chelate such as europium (Eu), via the use of antibody specific for the tag, and the co-activator peptide is labeled with allophycocyanin via a streptavidin-biotin linkage.

In the presence of an agonist for the nuclear receptor, the peptide is recruited to the tagged-LBD bringing europium and allophycocyanin into close proximity to enable energy transfer from the europium chelate to the allophycocyanin. Upon excitation of the complex with light at 340 nm excitation energy absorbed by the europium chelate is transmitted to the allophycocyanin moiety resulting in emission at 665 nm. If the europium chelate is not brought in to close proximity to the allophycocyanin moiety there is little or no energy transfer and excitation of the europium chelate results in emission at 615 nm. Thus the intensity of light emitted at 665 nm gives an indication of the strength of the protein-protein interaction. The activity of a nuclear receptor antagonist can be measured by determining the ability of a compound to competitively inhibit the activity of an agonist for the nuclear receptor. In the case of a constitutively active receptor, compound activity may be measured in terms of its ability to disrupt interaction between the receptor and the co-activator peptide.

Fluorescence in a sample can be measured using a fluorimeter, a fluorescent microscope or a fluorescent plate reader. Suitable instrumentation for fluorescence microplate readers include without limitation the CytoFluor™ 4000 available from PerSeptive Biosystems. For 96-well based assays, black walled plates with clear bottoms, such as those manufactured by Costar may be used. In general, all of these systems have an excitation light source which can be manipulated to create a light source with a defined wavelength maxima and band width which passes through excitation optics to excite the sample.

Typically, the excitation wavelength is designed to selectively excite the fluorescent sample within its excitation or absorption spectrum. For most FRET based assays the excitation wavelength is usually selected to enable efficient excitation of the donor while minimizing direct excitation of the acceptor. In response the sample (if fluorescent) emits radiation that has a wavelength that is different from the excitation wavelength. Collection optics then collect the emission from the sample, and direct it to one or more detectors, such as photomultiplier tubes or CCD cameras. Preferably the detector will include a filter to select specific wavelengths of light to monitor. For time resolved applications, for example time resolved FRET, the excitation and or emission optical paths include control mechanisms to precisely terminate illumination and then to wait for a precise period of time before collecting emitted light. By using compounds such as lanthanides that exhibit relatively long-lived light emission it is possible to gain significant enhancements in detection sensitivity and accuracy.

The detection devices can include a temperature controller to maintain the sample at a specific temperature while it is being scanned. According to one embodiment, a multi-axis translation stage moves a microtiter plate holding a plurality of samples in order to position different wells to be exposed. The multi-axis translation stage, temperature controller, autofocusing feature, and electronics associated with imaging and data collection can be managed by an appropriately programmed digital computer. The computer also can transform the data collected during the assay into another format for presentation.

Suitable instrumentation for luminescence measurements include standard liquid scintillation plate readers, including without limitation the Wallac Microbeta, or PE Biosystems Northstar, or equivalents commercially available from Packard, Perkin Elmer and a number of other manufacturers.

In addition to the binding assays mentioned above, a variety of cell based assay methodologies may be successfully used in screening assays to identify and profile the affinity of compounds of the present invention for ERR. These approaches include the co-transfection assay, translocation assays, complementation assays and the use of gene activation technologies to over express endogenous nuclear receptors.

Three basic variants of the co-transfection assay strategy exist, co-transfection assays using full-length nuclear receptor, co transfection assays using chimeric nuclear receptors comprising the ligand binding domain of the nuclear receptor of interest fused to a heterologous DNA binding domain, and assays based around the use of the mammalian two hybrid assay system.

The basic co-transfection assay is based on the co-transfection into the cell of an expression plasmid to express the nuclear receptor of interest in the cell with a reporter plasmid comprising a reporter gene whose expression is under the control of a promoter sequence that is capable of interacting with that nuclear receptor. (See for example U.S. Pat. Nos. 5,071,773, 5,298,429 and 6,416,957). Treatment of the transfected cells with an agonist for the nuclear receptor increases the transcriptional activity of that receptor which is reflected by an increase in expression of the reporter gene which may be measured by a variety of standard procedures. Alternatively, the host cell may be a primary cell or a cell line derived directly from a primary cell type, which endogenously expresses the nuclear receptor and appropriate co-factors. An assay system may comprise of transfecting into such a host cell a suitable reporter gene(s) and monitoring the transcriptional activity of the nuclear receptor in response to the addition of a test compound.

Typically, the expression plasmid comprises: (1) a promoter, such as an SV40 early region promoter, HSV tk promoter or phosphoglycerate kinase (pgk) promoter, CMV promoter, Srα promoter or other suitable control elements known in the art, (2) a cloned polynucleotide sequence, such as a cDNA encoding a receptor, co-factor, or a fragment thereof, ligated to the promoter in sense orientation so that transcription from the promoter will produce a RNA that encodes a functional protein, and (3) a polyadenylation sequence. As an example not to be construed as a limitation, an expression cassette of the invention may comprise the cDNA expression cloning vectors, or other preferred expression vectors known and commercially available from vendors such as Invitrogen, (CA), Stratagene, (CA) or Clontech, (CA). Alternatively expression vectors developed by academic groups such as the pCMX vectors originally developed in the Evans lab may also be used (Umesono et al., 1991, Cell 65:1255-1266).

The transcriptional regulatory sequences in an expression cassette are selected by the practitioner based on the intended application; depending upon the specific use, transcription regulation can employ inducible, repressible, constitutive, cell-type specific, developmental stage-specific, sex-specific, or other desired type of promoter or control sequence.

Alternatively, the expression plasmid may comprise an activation sequence to activate or increase the expression of an endogenous chromosomal sequence. Such activation sequences include for example, a synthetic zinc finger motif (for example see U.S. Pat. Nos. 6,534,261 and 6,503,7171) or a strong promoter or enhancer sequence together with a targeting sequence to enable homologous or non-homologous recombination of the activating sequence upstream of the gene of interest.

In another embodiment of these methods, chimeras may be used in place of the full-length nuclear receptor. Such chimeras typically comprise the ligand binding domain of the ERR coupled to a heterologous DNA binding domain (DBD).

Typically for such chimeric constructs, DNA binding domains from yeast or bacterially derived transcriptional regulators such as members of the GAL 4 and Lex A (GenBank accession number ILEC)/Umud super families may be used. GAL4 (GenBank Accession Number P04386,) is a positive regulator for the expression of the galactose-induced genes. (see, for example, Keegan et al., 1986, Science 231: 699-704). Reporter plasmids may be constructed using standard molecular biological techniques by placing cDNA encoding for the reporter gene downstream from a suitable minimal promoter. For example, luciferase reporter plasmids may be constructed by placing cDNA encoding firefly luciferase (typically with SV40 small t intron and poly-A tail, (de Wet et al., 1987, Mol. Cell. Biol. 7:725-735) down stream from the herpes virus thymidine kinase promoter (located at nucleotides residues −105 to +51 of the thymidine kinase nucleotide sequence, pBLCAT2 (Luckow & Schutz, 1987, Nucl. Acid. Res. 15:5490-5494)) which is linked in turn to the appropriate response elements.

Alternatively, heterologous DNA binding domains from distinct, well-defined nuclear receptors are used, for example including without limitation, the DBDs of the glucocorticoid receptor, GR (accession no. NM__000176) (amino acids 421-486), mineralocorticoid receptor, MR (accession no. NM__055775) (amino acids 603-668), androgen receptor, AR (accession no XM__010429NM__055775) (amino acids 929-1004), progesterone receptor, PR (amino acids 622-695), and estrogen receptor alpha, ERα (accession no. XM__045967) (amino acids 185-250).

The choice of hormone response element is dependent upon the type of assay to be used. In the case of the use of the full length ERR, a known ER or ERRE would typically be used. In the case of an ERR-LBD-GAL4 fusion, a GAL4 UAS would be used. An example of a GAL4 UAS binding site typically used is the MH100 binding site (Kang et al., 1993, J. Biol. Chem. 268(13): 9629-9363).

Numerous reporter gene systems are known in the art and include, for example, alkaline phosphatase (see, Berger, J., et al., 1988, Gene, 66:1-10; and Kain, S. R., 1997, Methods. Mol. Biol. 63:49-60), β-galactosidase (See, U.S. Pat. No. 5,070,012 and Bronstein, I., et al., 1989, J. Chemilum. Biolum. 4:99-111), chloramphenicol acetyltransferase (See, Gorman et al., 1982, Mol. Cell. Biol. 2:1044-5), β-glucuronidase, peroxidase, β-lactamase (U.S. Pat. Nos. 5,741,657 and 5,955,604), catalytic antibodies, luciferases (U.S. Pat. Nos. 5,221,623; 5,683,888; 5,674,713; 5,650,289; and 5,843,746) and naturally fluorescent proteins (Tsien, R. Y., 1998, *Annu. Rev. Biochem.* 67: 509-544,).

Numerous methods of co-transfecting the expression and reporter plasmids are known to those of skill in the art and may be used for the co-transfection assay to introduce the plasmids into a suitable cell type. One method for identifying compounds that promote co-factor recruitment or nuclear receptor heterodimerization is the mammalian two-hybrid assay (see, for example, U.S. Pat. Nos. 5,667,973, 5,283,173 and 5,468,614). A typical two-hybrid assay involves the expression of two fusion proteins, one of which can be the GAL4 DNA binding domain fused to a "bait" protein such as a coactivator peptide, and the other of which can be a strong transactivation domain of a transcriptional activator such as VP16 fused to a "prey" protein such as a nuclear receptor. The interaction of the "bait" and "prey" protein brings the transcriptional activator to the promoter which leads to transcriptional activity which can be detected by the activation of a reporter gene (Fields, S. and Song, O., 1989, Nature 340: 245; Willy et al., 1995, Gene & Development 9:1033-1045). In one example of a two-hybrid assay, functional interaction between a GAL4-SRC-1 fusion protein and VP16-ERR fusion protein leads to constitutive activation of a suitable reporter plasmid, such as luciferase reporter construct comprising GAL4 Upstream Activating Sequences (UAS). Any compound which is a candidate for modulation of ERR may be tested by any of the above methods. Generally, compounds are tested at several different concentrations to optimize the chances that regulation of the receptor will be detected and recognized if present. Typically assays are performed in triplicate and vary within experimental error by less than 15%. Each experiment is typically repeated three or more times with similar results.

Agonist activity may be measured by the activity of the reporter gene normalized to the internal control and the data plotted as fold activation relative to untreated cells. Antagonist activity can be measured by determining the ability of a compound to competitively inhibit the activity of an agonist or the receptor's constitutive activity. A control compound (agonist or antagonist) may be included along with DMSO for normalization of the assay data.

Additionally, the compounds and compositions can be evaluated for their ability to increase or decrease the expression of genes known to be modulated by ERR and other nuclear receptors in vivo, using Northern-blot, RT PCR or oligonucleotide microarray analysis to analyze RNA levels. Western-blot analysis can be used to measure expression of proteins encoded by ERR target genes. Genes that are known to be regulated by the ERR include without limitation, osteopontin, medium-chain acyl CoA dehydrogenase (MCAD), arcomatase, lactoferrin and pS2.

All methods discussed thus far may be adapted for use in high throughput screening. High throughput screening systems are commercially available (see, e.g., Zymark Corp., Hopkinton, Mass.; Air Technical Industries, Mentor, Ohio; Beckman Instruments Inc., Fullerton, Calif.; Precision Systems, Inc., Natick, Mass.) that enable these assays to be run in a high throughput mode. These systems typically automate entire procedures, including all sample and reagent pipetting, liquid dispensing timed incubations, and final readings of the microplate in detector(s) appropriate for the assay. These configurable systems provide high throughput and rapid start up as well as a high degree of flexibility and customization. The manufacturers of such systems provide detailed protocols for various high throughput systems. Thus, for example, Zymark Corp. provides technical bulletins describing screening systems for detecting the modulation of gene transcription, ligand binding, and the like.

Assays that do not require washing or liquid separation steps are preferred for such high throughput screening systems and include biochemical assays such as fluorescence polarization assays (see, for example, Owicki, J., 2000, *Biomol. Screen* 5(5):297), scintillation proximity assays (SPA) (see, for example, Carpenter et al., 2002, *Methods Mol. Biol.* 190:31-49) and fluorescence resonance energy transfer energy transfer (FRET) or time resolved FRET based coactivator recruitment assays (Mukherjee et al., 2002, *J. Steroid Biochem. Mol. Biol.* 81(3):217-25; Zhou et al., 1998, *Mol. Endocrinol.* 12(10):1594-604).

Established animal models exist for a number of diseases of direct relevance to the claimed compounds and these can be used to further profile and characterize the claimed compounds. These model systems include Zucker (fa/fa) rats or (db/db) mice for studying diabetic dyslipidemia, nude mice transplanted with tumor cells for tumor growth studies, non-obese diabetic mouse (NOD) for type-1 diabetes studies and ovariectimized rats (OVX) for osteoporosis studies.

Additionally ERR animal models (e.g., knockout mice) can be used to further evaluate the present compounds and compositions in vivo (Luo J. et al., 2003, Mol. Cell. Biol., 23:7947-7956).

D. Administration of the Compounds of the Invention

Also provided herein are methods of using the disclosed compounds and composition for the local or systemic treatment or prophylaxis of human and veterinary diseases, disorders and conditions mediated by ERRα, including without limitation:

(a) diseases or disorder relating to the metabolic syndrome including hyperglycemia, insulin insensitivity, diabetes, obesity, hyperlipidermia, hypercholesterolemia, hyperlipoproteinemia, hypertriglyceridemia, dyslipidemia, hypertension, hyperinsulinemia, hyperuricemia, or a combination thereof;

(b) diseases or disorders relating to cancer;

(c) diseases or disorder relating to the bone or cartilage, including arthritis, osteoarthritis and rheumatoid arthritis, (d) inflammatory diseases, conditions or disorders due to the release of proinflammatory cytokines including rheumatoid arthritis and atherosclerosis, and (e) psychosis and neurodegenerative or stress-related disorders including Parkinson's disease, Alzheimer's disease, depression, anxiety and chemical dependency.

In one embodiment, the disclosed compounds and compositions are ERRα modulators. In another embodiment, the disclosed compounds and compositions are ERRα antagonists. In yet another embodiment, the disclosed compounds and compositions are ERRα partial agonists. In yet another embodiment, the disclosed compounds and compositions are ERRα inverse agonists.

Administration of the disclosed compounds and compositions, or their pharmaceutically acceptable salts, in pure form or in an appropriate pharmaceutical composition, can be carried out via any of the accepted modes of administration of agents for serving similar utilities. The pharmaceutical compositions of the invention can be prepared by combining a compound of the invention with an appropriate pharmaceutically acceptable carrier, diluent or excipient, and may be formulated into preparations in solid, semi-solid, liquid or gaseous forms, such as tablets, capsules, powders, granules, ointments, solutions, suppositories, injections, inhalants, gels, microspheres, and aerosols. Typical routes of administering such pharmaceutical compositions include, without limitation, oral, topical, transdermal, inhalation, parenteral, sublingual, rectal, vaginal, and intranasal. The term parenteral as used herein includes subcutaneous injections, intravenous, intramuscular, intrasternal injection or infusion techniques. Pharmaceutical compositions of the invention are formulated so as to allow the active ingredients contained therein to be bioavailable upon administration of the composition to a patient. Compositions that will be administered to a subject or patient take the form of one or more dosage units, where for example, a tablet may be a single dosage unit, and a container of a compound of the invention in aerosol form may hold a plurality of dosage units. Actual methods of preparing such dosage forms are known, or will be apparent, to those skilled in this art; for example, see Remington's Pharmaceutical Sciences, 18th Ed., (Mack Publishing Company, Easton, Pa., 1990). The composition to be administered will, in any event, contain a therapeutically effective amount of a compound of the invention, or a pharmaceutically acceptable salt thereof, for treatment of a disease-state associated with the activity of a nuclear receptor in accordance with the teachings of this invention.

In one embodiment, the pharmaceutical composition may be in the form of a solid or liquid. In one aspect, the carrier(s) are particulate, so that the compositions are, for example, in tablet or powder form. The carrier(s) may be liquid, with the compositions being, for example, an oral syrup, injectable liquid or an aerosol, which is useful in, e.g., inhalatory administration.

When intended for oral administration, the pharmaceutical composition is preferably in either solid or liquid form, where semi-solid, semi-liquid, suspension and gel forms are included within the forms considered herein as either solid or liquid.

As a solid composition for oral ad ministration, the pharmaceutical composition may be formulated into a powder, granule, compressed tablet, pill, capsule, chewing gum, wafer or the like form. Such a sol id composition will typically contain one or more inert diluents or edible carriers. In addition, one or more of the following may be present: binders such as carboxymethylcellulose, ethyl cellulose, microcrystalline cellulose, gum tragacanth or gelatin; excipients such as starch, lactose or dextrins, disintegrating agents such as alginic acid, sodium alginate, Primogel, corn starch and the like; lubricants such as magnesium stearate or Sterotex; glidants such as colloidal silicon dioxide; sweetening agents such as sucrose or saccharin; a flavoring agent such as peppermint, methyl salicylate or orange flavoring; and a coloring agent.

When the pharmaceutical composition is in the form of a capsule, e.g., a gelatin capsule, it may contain, in addition to materials of the above type, a liquid carrier such as polyethylene glycol or oil.

The pharmaceutical composition may be in the form of a liquid, e.g., an elixir, syrup, solution, emulsion or suspension. The liquid may be for oral administration or for delivery by injection, as two examples. When intended for oral administration, preferred composition contain, in addition to the present compounds, one or more of a sweetening agent, preservatives, dye/colorant and flavor enhancer. In a composition intended to be administered by injection, one or more of a surfactant, preservative, wetting agent, dispersing agent, suspending agent, buffer, stabilizer and isotonic agent may be included.

In one embodiment, the liquid pharmaceutical compositions, whether they are solutions, suspensions or other like form, may include one or more of the following adjuvants: sterile diluents such as water for injection, saline solution, preferably physiological saline, Ringer's solution, isotonic sodium chloride, fixed oils such as synthetic mono or diglycerides which may serve as the solvent or suspending medium, polyethylene glycols, glycerin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or pi astic. Physiological saline is a preferred adjuvant. An injectable pharmaceutical composition is preferably sterile.

In one embodiment, the liquid pharmaceutical composition intended for either parenteral or oral administration should contain an amount of a compound of the invention such that a suitable dosage will be obtained. Typically, this amount is at least 0.01% of a compound of the invention in the composition. When intended for oral administration, this amount may be varied to be between 0.1 and about 70% of the weight of the composition. Preferred oral pharmaceutical compositions contain between about 4% and about 50% of the compound of the invention. Preferred pharmaceutical compositions and preparations according to the present invention are prepared so that a parenteral dosage unit contains between 0.01 to 1% by weight of the compound of the invention.

In another embodiment, the pharmaceutical composition may be intended for topical administration, in which case the carrier may suitably comprise a solution, emulsion, ointment or gel base. The base, for example, may comprise one or more of the following: petrolatum, lanolin, polyethylene glycols, bee wax, mineral oil, diluents such as water and alcohol, and emulsifiers and stabilizers. Thickening agents may be present in a pharmaceutical composition for topical administration. If intended for transdermal administration, the composition may include a transdermal patch or iontophoresis device. Topical formulations may contain a concentration of the compound of the invention from about 0.1 to about 10% w/v (weight per unit volume).

In another embodiment, the pharmaceutical composition may be intended for rectal administration, in the form, e.g., of a suppository, which will melt in the rectum and release the drug. The composition for rectal administration may contain an oleaginous base as a suitable nonirritating excipient. Such bases include, without limitation, lanolin, cocoa butter and polyethylene glycol.

In another embodiment, the pharmaceutical composition may include various materials, which modify the physical form of a solid or liquid dosage unit. For example, the composition may include materials that form a coating shell around the active ingredients. The materials that form the coating shell are typically inert, and may be selected from, for example, sugar, shellac, and other enteric coating agents. Alternatively, the active ingredients may be encased in a gelatin capsule.

In another embodiment, the pharmaceutical composition in solid or liquid form may include an agent that binds to the compound of the invention and thereby assists in the delivery of the compound. Suitable agents that may act in this capacity include a monoclonal or polyclonal antibody, a protein or a liposome.

In another embodiment, the pharmaceutical composition may consist of dosage units that can be administered as an aerosol. The term aerosol is used to denote a variety of systems ranging from those of colloidal nature to systems consisting of pressurized packages. Delivery may be by a liquefied or compressed gas or by a suitable pump system that dispenses the active ingredients. Aerosols of compounds of the invention may be delivered in single phase, bi-phasic, or tri-phasic systems in order to deliver the active ingredient(s). Delivery of the aerosol includes the necessary container, activators, valves, subcontainers, and the like, which together may form a kit. One skilled in the art, without undue experimentation may determine preferred aerosols.

In another embodiment, the pharmaceutical composition may be prepared by methodology well known in the pharmaceutical art. For example, a pharmaceutical composition intended to be administered by injection can be prepared by combining a compound of the invention with sterile, distilled water so as to form a solution. A surfactant may be added to facilitate the formation of a homogeneous solution or suspension. Surfactants are compounds that non-covalently interact with the compound of the invention so as to facilitate dissolution or homogeneous suspension of the compound in the aqueous delivery system.

In one embodiment, the disclosed compounds, or their pharmaceutically acceptable salts, are administered in a therapeutically effective amount, which will vary depending upon a variety of factors including the activity of the specific compound employed; the metabolic stability and length of action of the compound; the age, body weight, general health, sex, and diet of the patient; the mode and time of administration; the rate of excretion; the drug combination; the severity of the particular disorder or condition; and the subject undergoing therapy. Generally, a therapeutically effective daily dose is from about 0.1 mg to about 20 mg/kg of body weight per day of a compound of the invention, or a pharmaceutically acceptable salt thereof; preferably, from about 0.1 mg to about 10 mg/kg of body weight per day; and most preferably, from about 0.1 mg to about 7.5 mg/kg of body weight per day.

Compounds of the invention, or pharmaceutically acceptable derivatives thereof, may also be administered simultaneously with, prior to, or after administration of one or more of the therapeutic agents described above in the Summary of the Invention. Such combination therapy includes administration of a single pharmaceutical dosage formulation which contains a compound of the invention and one or more additional active agents, as well as administration of the compound of the invention and each active agent in its own separate pharmaceutical dosage formulation.

Suitable agents for combination therapy include those that are commercially available and those currently in development or that will be developed. Exemplary agents useful for treatment of metabolic disorders in combination with the compounds and composition disclosed herein include, but are not limited to: (a) anti-diabetic agents including sulfonylureas (such as chlorpropamide, tolbutamide, acetohexamide, tolazamide, glyburide, gliclazide, glynase, glimepiride, and glipizide), biguanides (such as metformin), thiazolidinediones (such as ciglitazone, pioglitazone, troglitazone, and rosiglitazone), and related insulin sensitizers, such as selective and non-selective activators of PPARα, PPARβ and PPARγ; dehydroepiandrosterone (also referred to as DHEA or its conjugated sulphate ester, DHEA-SO$_4$); antiglucocorticoids; TNFα inhibitors; α-glucosidase inhibitors (such as acarbose, miglitol, and voglibose), pramlintide (a synthetic analog of the human hormone amylin), other insulin secretogogues (such as repaglinide, gliquidone, and nateglinide), insulin; agonists, partial agonists, antagonists, or inverse agonists of LXRα and/or LXRβ; FXR agonists, partial agonists, antagonists, or inverse agonists; (b) agents for the treatment of obesity including phenylpropanolamine, phentermine, diethylpropion, mazindol, fenfluramine, dexfenfluramine, phentiramine, β$_3$ adrenoceptor agonist agents; sibutramine, gastrointestinal lipase inhibitors (such as orlistat), and leptins. Other agents used in treating obesity or obesity-related disorders include neuropeptide Y, enterostatin, cholecytokinin, bombesin, amylin, histamine H$_3$ receptors, dopamine D$_2$ receptors, melanocyte stimulating hormone, corticotrophin releasing factor, galanin and gamma amino butyric acid (GABA); (c) anti-atherosclerotic agents including antihyperlipidemic agents, plasma HDL raising agents, antihypercholesterolemic agents, cholesterol biosynthesis inhibitors including HMG-CoA reductase inhibitor, such as lovastatin (MEVACOR®; see, U.S. Pat. No. 4,231,938); simvastatin (ZOCOR®; see, U.S. Pat. No. 4,444,784); pravastatin sodium (PRAVACHOL®; see, U.S. Pat. No. 4,346,227); fluvastatin sodium (LESCOL®; see, U.S. Pat. No. 5,354,772); atorvastatin calcium (LIPITOR®; see, U.S. Pat. No. 5,273,995) and rivastatin (also known as cerivastatin; see, U.S. Pat. No. 5,177,080), acyl-coenzyme A:cholesterol acytransferase (ACAT) inhibitors, probucol, raloxifene, nicotinic acid, niacinamide, cholesterol absorption inhibitors, bile acid sequestrants (such as anion exchange resins, or quaternary amines (e.g., cholestyramine or colestipol)), low density lipoprotein receptor inducers, clofibrate, fenofibrate, benzofibrate, cipofibrate, gemfibrizol, vitamin B$_6$, vitamin B$_{12}$, anti-oxidant vitamins, β-blockers, angiotensin II antagonists, angiotensin converting enzyme inhibitors, platelet aggregation inhibitors, fibrinogen receptor antagonists, aspirin or fibric acid derivatives; (d) anti-cancer agents including anti-metabolites (e.g., 5-fluoro-uracil, methotrexate, fludarabine), antimicrotubule agents (e.g., vinca alkaloids such as vincristine, vinblastine; taxanes such as paclitaxel, docetaxel), an alkylating agent (e.g., cyclophosphamide, melphalan, carmustine, nitrosoureas such as bischloroethylnitrosurea and hydroxyurea), platinum agents (e.g. cisplatin, carboplatin, oxaliplatin, JM-216, CI-973), anthracyclines (e.g., doxrubicin, daunorubicin), antitumor antibiotics (e.g., mitomycin, idarubicin, adriamycin, daunomycin), topoisomerase inhibitors (e.g., etoposide, camptothecins) or any other cytotoxic agents, (estramustine phosphate, prednimustine), hormones or agents acting on nuclear hormone receptors (steroids and anti-steroids, estrogens, anti-estrogens, androgens, anti-androgens, glucocorticoids, dexamethasone),
(e) agents for the treatment of osteoporosis including parathyroid hormone (PTH) or physiologically active fragment thereof, (hPTHF 1-34) or dietary calcium supplement; and (f) anti-arthritic agents including matrix metalloproteinase inhibitor, an inhibitor of pro-inflammatory cytokines (e.g., anti-TNF molecules, TNF soluble receptors, and IL1 beta, non-steroidal anti-inflammatory drugs (NSAIDs) such as prostaglandin synthase inhibitors (e.g., choline magnesium salicylate, salicylsalicyclic acid), or corticosteroids, such as methylprednisone, prednisone, or cortisone.

Combination therapy can also include co-administration of the compound or composition disclosed herein with a treatment method such as radiation therapy for the treatment of cancer. Another combination therapy comprises administration to a human afflicted with a neurological disorder, a combination of a monoamine oxidase inhibitor such as phenelzine, tranylcypromine, pargyline, deprenyl, moclobemide, brofaromine, moclobemide or selegiline with any of the claimed compounds or compositions.

The foregoing examples are provided only to illustrate the present invention and are in no way intended to limit to the scope thereof. The skilled practitioner will understand that considerable variations in the practice of this invention are possible within the spirit and scope as claimed below.

Although only one of two possible geometric isomers around the double bond (i.e., the E and Z isomers) is exemplified, alternative geometric isomers are also meant to be included in the compound descriptions. For those compounds with alternative tautomeric forms, although only one of two possible tautomers is exemplified, the alternative isomers are also meant to be included in the compound descriptions. The $^1$H NMR data indicate that the compounds are one isomer, but it is not known which isomer is the actual compound prepared. The NMR spectra were acquired on a Bruker 400 MHz instrument. The chemical shifts are reported in ppm (δ) and are relative to the central peak of the solvent. The following abbreviations are used: br s=broad singlet, s=singlet, d=doublet, t=triplet, q=quartet, dd=doublet of doublet, m=multiplet.

Low-resolution mass spectra (MS) were obtained as electrospray ionization (ESI) mass spectra, which were recorded on a Perkin-Elmer SCIEX HPLC/MS instrument using reverse-phase conditions (acetonitrile/water, 0.05% trifluoroacetic acid). The infrared (IR) spectra were acquired on an Avatar 360 FT-IR instrument. The samples were prepared as KBr pellets, and the absorptions are reported as wavenumbers (ν) in the unit of reciprocal centimeters ($cm^{-1}$). Flash chromatography was performed using Merck Silica Gel 60 (230-400 mesh) following standard protocol (Still et al. (1978) *J. Org. Chem.* 43, 2923).

The following examples are included for illustrative purposes only and are not intended to limit the scope of the invention. The structures contained in the examples reflect only one of two possible C═C geometrical isomers (E and Z). The 1H NMR data indicate that the compounds are one isomer, but it is not known which isomer is the actual compound prepared. The NMR spectra were acquired on a Bruker Avance 400 MHz instrument. The chemical shifts are reported in ppm (δ) and are relative to the central peak of the solvent. The following abbreviations are used: br s=broad singlet, s=singlet, d=doublet, t=triplet, q=quartet, dd=doublet of doublet, m=multiplet.

Example 1

Preparation of '5-[1-[4-(2,4-Bis-trifluoromethyl-benzyloxy)-3-methoxy-phenyl]-methylidene]-2-thioxo-thiazolidin-4-one

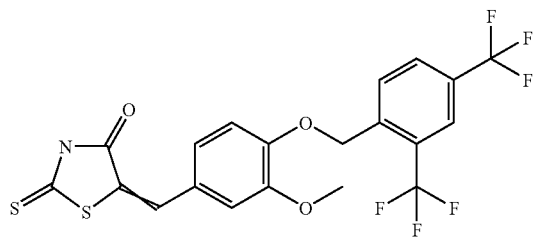

A. Preparation of 4-(2,4-bis(trifluoromethyl)benzyloxy)-3-methoxybenzaldehyde

To a flask was added 1-bromomethyl-2,4-bis-trifluoromethyl-benzene (2.27 g, 7.39 mmol), vanillin (1.12 g, 1 equiv), DMF (23 mL) and fine mesh $K_2CO_3$ (5.11 g, 37 mmol). The reaction slurry was stirred at 70° C. for 15 h. The reaction solution was diluted with EtOAc (120 mL), filtered through a Buchner funnel, washed with sat $NH_4Cl$ (50 mL×2), dried over $Na_2SO_4$, filtered, and concentrated. The crude material was chromatographed ($SiO_2$, Hex/EtOAc: 100:0 to 70:30) to yield intermediate product (2.79 g, 86%). $^1$H NMR (400 MHz, $CDCl_3$) δ 9.88 (s, 1H), 7.97 (d, J=8 Hz, 1H), 7.96 (s, 1H), 7.85 (d, J=8 Hz, 1H), 7.48 (s, 1H), 7.42 (d, J=8 Hz, 1H), 6.93 (d, J=8 Hz, 1H), 5.48 (s, 2H), 3.99 (s, 3H); MS (ESI) 379 ($MH^+$).

B. Preparation of Title Compound

To a flask was added 4-(2,4-bis(trifluoromethyl)benzyloxy)-3-methoxybenzaldehyde from Step A (164 mg, 433 μmol), rhodanine (58 mg, 433 μmol), absolute EtOH (7 mL), and TEA (120 μL, 870 μmol). The reaction solution was allowed to stir at 65° C. for 14 h. The reaction solution was diluted with EtOAc (100 mL), washed with sat. $NH_4Cl$ (75 mL×3), dried over $Na_2SO_4$, filtered, and concentrated to ⅓ the original volume. The yellow precipitates were isolated by filtration under reduced pressure, washed with EtOAc (50 mL) and $Et_2O$ (50 mL) to afford the title compound (47 mg, 23%). $^1$H NMR (DMSO-$d_6$) δ 13.25 (1H, br s), 7.90 (1H, d, J=8.1 Hz), 7.86 (1H, s), 7.80 (1H, d, J=8.60 Hz), 7.48 (1H, s), 6.99 (1H, dd, J=2.0 Hz, 8.6 Hz), 6.96 (1H, d, J=2.0 Hz), 6.86 (1H, d, J=8.3 Hz), 5.35 (2H, s), 3.88 (3H, s); MS (ESI) 494 ($MH^+$).

Example 2

Preparation of '5-[1-[4-(2,4-Bis-trifluoromethyl-benzyloxy)-3-methoxy-phenyl]-methylidene]-2-ethylamino-thiazol-4-one

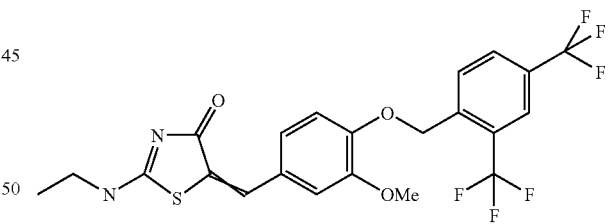

To a flask was added '5-[1-[4-(2,4-Bis-trifluoromethyl-benzyloxy)-3-methoxy-phenyl]-methylidene]-2-thioxo-thiazolidin-4-one (59 mg, 120 μmol), anhydrous DMF (1 mL), and iodomethane (3.0 mL). The solution was allowed to stir at 40° C. for 2.5 h. The reaction solution was concentrated under reduced pressure, and the residue was dissolved in anhydrous MeCN (3 mL). To the mixture was added a 2.0 M solution of $EtNH_2$ in THF (1.0 mL). The solution was stirred at 60° C. for 2 h. The solution was concentrated under reduced pressure, and the crude material was chromatographed ($SiO_2$ DCM/MeOH 100:0 to 90:10) to provide the title product (21 mg, 34%). $^1$H NMR (DMSO-$d_6$) δ 9.58 (1H, t, J=5.6 Hz), 8.17 (1H, d, J=8.1 Hz), 8.10 (1H, s), 8.03 (1H, d, J=8.3 Hz), 7.57 (1H, s), 7.17-7.26 (3H, m), 5.40 (2H, s), 3.85 (3H, s), 3.53 (2H, m), 1.19 (3H, t, J=7.3 Hz); MS (ESI) 505 (MH$^+$),

Example 3

Preparation of '5-[1-[4-(2,4-Bis-trifluoromethyl-benzyloxy)-3-methoxy-phenyl]-methylidene]-2-(2-methoxy-ethylamino)-thiazol-4-one

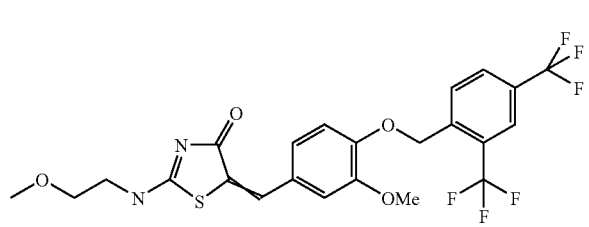

The title compound was prepared in a manner similar to that described in Example 2 by using 2-methoxyethyl amine in place of EtNH$_2$ and by using organic solvents acetonitrile and DMF in place of THF. $^1$H NMR (DMSO-d$_6$) δ 9.71 (1H, t, J=5.6 Hz), 8.17 (1H, d, J=8.1 Hz), 8.10 (1H, s), 8.02 (1H, d, J=8.1 Hz), 7.57 (1H, s), 7.25 (1H, d, J=1.9 Hz), 7.12-7.20 (2H, m), 5.40 (2H, s), 3.87 (3H, s), 3.66 (2H, m), 3.52 (2H, t, J=5.3 Hz), 3.29 (3H, s); MS (ESI) 435 (MH$^+$).

Example 4

Preparation of '5-[1-[4-(2,4-Bis-trifluoromethyl-benzyloxy)-3 methoxy-phenyl]-methylidene]-2-(4-methoxy-benzylamino)-thiazol-4-one

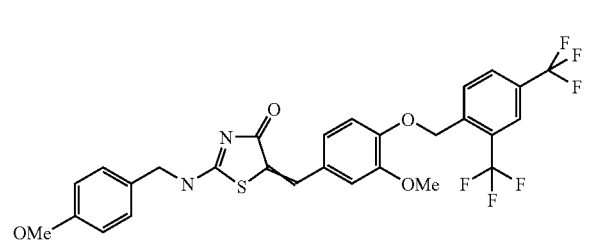

The title compound was prepared in a manner similar to that described in Example 2 by using 4-methoxybenzyl amine in place of EtNH$_2$ and by using organic solvents acetonitrile and DMF in place of THF. MS (ESI) 597 (MH$^+$).

Example 5

Preparation of '5-[1-[4-(2,4-Bis-trifluoromethyl-benzyloxy)-3-methoxy-phenyl]-methylidene]-2-(2,4-difluoro-benzylamino)-thiazol-4-one

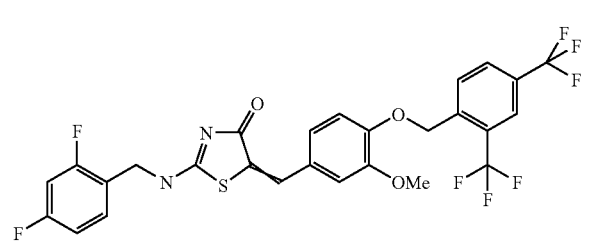

The title compound was prepared in a manner similar to that described in Example 2 by using 2,4-difluorobenzyl amine in place of EtNH$_2$ and by using organic solvents acetonitrile and DMF in place of THF. MS (ESI) 603 (MH$^+$).

Example 6

Preparation of '5-[1-[4-(2,4-Bis-trifluoromethyl-benzyloxy)-3-methoxy-phenyl]-methylidene]-2-(2-N,N-dimethylamino-ethylamino)-thiazol-4-one The title compound was prepared in a manner similar to that described in Example 2 by using 2(N,N-dimethylamino) ethyl amine in place of EtNH$_2$ and by using organic solvents acetonitrile and DMF in place of THF. MS (ESI) 562 (MH$^+$).

Example 7

Preparation of '5-[1-[4-(2,4-Bis-trifluoromethyl-benzyloxy)-3-methoxy-phenyl]-methylidene]-2-(2-ethoxy-ethylamino)-thiazol-4-one The title compound was prepared in a manner similar to that described in Example 2 by using 2-ethoxyethylamine in place of EtNH$_2$. MS (ESI) 449 (MH$^+$).

Example 8

Preparation of '5-[1-[4-(2,4-Bis-trifluoromethyl-benzyloxy)-3-methoxy-phenyl]-methylidene]-2-methylamino-thiazol-4-one The title compound was prepared in a manner similar to that described in Example 2 by using methylamine in place of EtNH$_2$ and by carrying out the reaction in a Kontes sealed tube. MS (ESI) 491 (MH$^+$).

Example 9

Preparation of '5-[1-[4-(2,4-Bis-trifluoromethyl-benzyloxy)-3-methoxy-phenyl]-methylidene]-2-phenethylamino-thiazol-4-one

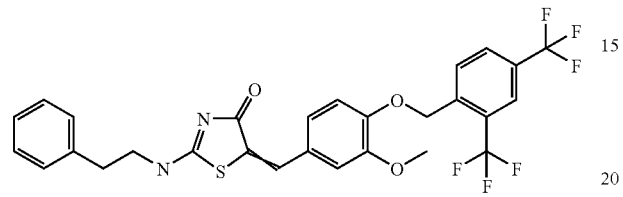

The title compound was prepared in a manner similar to that described in Example 2 by using phenylethylamine in place of EtNH$_2$ and by using organic solvents acetonitrile and DMF in place of THF. MS (ESI) 581 (MH$^+$).

Example 10

Preparation of '5-[1-[4-(2,4-Bis-trifluoromethyl-benzyloxy)-3-methoxy-phenyl]-methylidene]-2-propylamino-thiazol-4-one

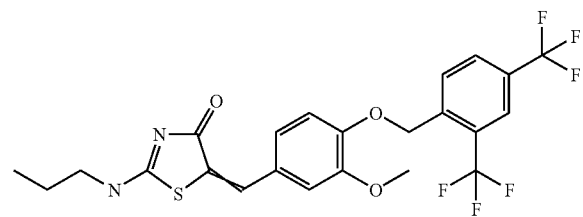

The title compound was prepared in a manner similar to that described in Example 2 by using n-propylamine in place of EtNH$_2$— MS (ESI) 519 (MH$^+$).

Example 11

Preparation of '5-[1-[4-(2,4-Bis-trifluoromethyl-benzyloxy)-3-methoxy-phenyl]-methylidene]-2-dimethylamino-thiazol-4-one

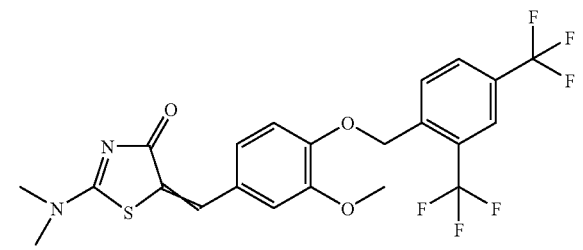

The title compound was prepared in a manner similar to that described in Example 2 by using N,N-dimethylamine in place of EtNH$_2$ and by carrying out the reaction in a Kontes sealed tube. $^1$H NMR (DMSO-d$_6$) δ 8.16 (1H, d, J=8.1 Hz), 8.10 (1H, s), 8.02 (1H, d, J=8.1 Hz), 7.59 (1H, s), 7.29 (1H, d, J=2.0 Hz), 7.14-7.19 (2H, m), 5.41 (2H, s), 3.86 (3H, s), 3.31 (3H, s), 3.25 (3H, s); MS (ESI) 505 (MH$^+$).

Example 12

Preparation of '5-[1-[4-(2,4-Bis-trifluoromethyl-benzyloxy)-3-methoxy-phenyl]-methylidene]-2-cyclohexylamino-thiazol-4-one

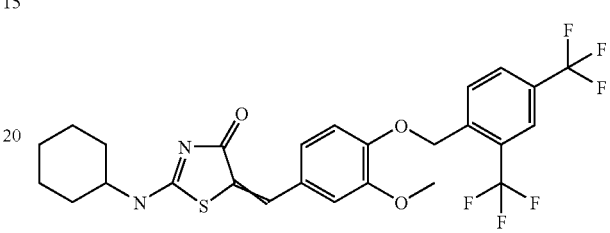

The title compound was prepared in a manner similar to that described in Example 2 by using cyclohexylamine in place of EtNH$_2$ and by using organic solvents acetonitrile and DMF in place of THF. MS (ESI) 559 (MH$^+$).

Example 13

Preparation of '5-[1-[4-(2,4-Bis-trifluoromethyl-benzyloxy)-3-methoxy-phenyl]-methylidene]-2-(2-morpholin-4-yl-ethylamino)-thiazol-4-one

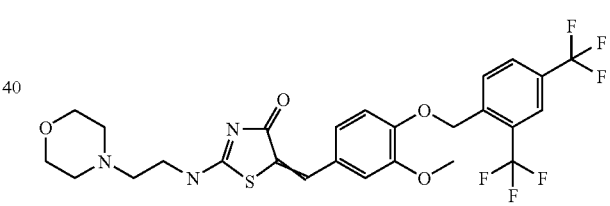

The title compound was prepared in a manner similar to that described in Example 2 by using 4-ethylamine morpholine in place of EtNH$_2$ and by using organic solvents acetonitrile and DMF in place of THF. MS (ESI) 590 (MH$^+$).

Example 14

Preparation of '5-[1-[4-(2,4-Bis-trifluoromethylbenzyloxy)-3-methoxy-phenyl]-methylidene]-2-hydroxyamino-thiazol-4-one

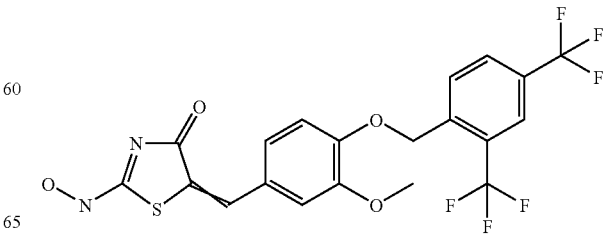

The title compound was prepared in a manner similar to that described in Example 2 by using hydroxylamine-HCl in place of EtNH₂. MS (ESI) 493 (MH⁺).

Example 15

Preparation of '3-{5-[1-[4-(2,4-Bis-trifluoromethyl-benzyloxy)-3-methoxy-phenyl]-methylidene]-4-oxo-4,5-dihydro-thiazol-2-ylamino}-benzoic acid ethyl ester

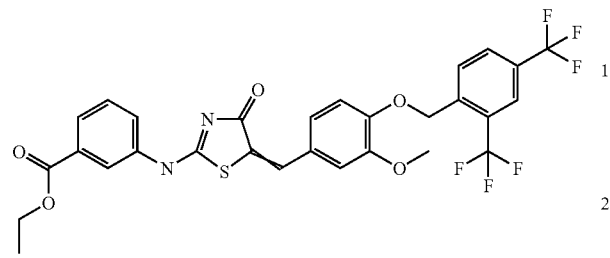

The title compound was prepared in a manner similar to that described in Example 2 by using 3-amino benzoic acid ethyl ester in place of EtNH₂— MS (ESI) 625 (MH⁺).

Example 16

Preparation of '5-[1-[4-(2,4-Bis-trifluoromethyl-benzyloxy)-3-methoxy-phenyl]-methylidene]-2-phenylamino-thiazol-4-one

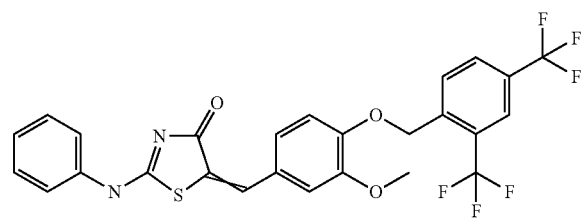

The title compound was prepared in a manner similar to that described in Example 2 by using phenylamine in place of EtNH₂ and by using organic solvents acetonitrile and DMF in place of THF. MS (ESI) 553 (MH⁺).

Example 17

Preparation of '5-[1-[4-(2,4-Bis-trifluoromethyl-benzyloxy)-3-methoxy-phenyl]-methylidene]-2-(ethyl-phenyl-amino)-thiazol-4-one

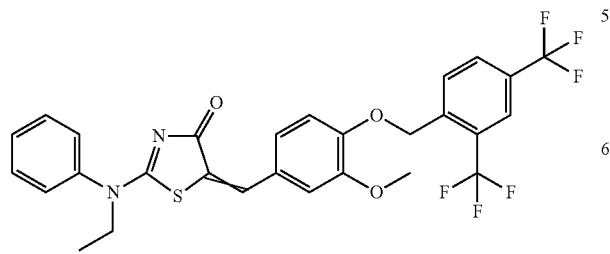

The title compound was prepared in a manner similar to that described in Example 2 by using N-ethyl-phenylamine in place of EtNH₂ and by using organic solvents acetonitrile and DMF in place of THF. MS (ESI) 581 (MH⁺).

Example 18

Preparation of 5-[1-[4-(2,4-Bis-trifluoromethyl-benzyloxy)-3-methoxy-phenyl]-methylidene]-2-(4-methyl-piperazin-1-yl)-thiazol-4-one

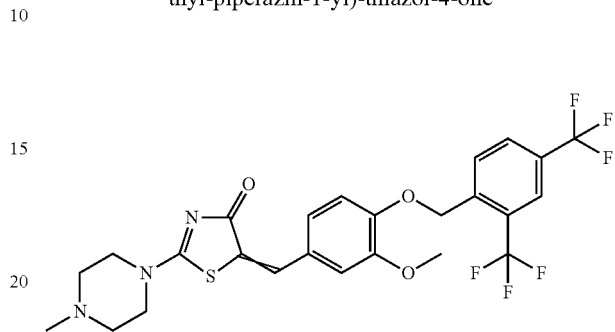

To a flask purged with N₂ was added '5-[1-[4-(2,4-Bis-trifluoromethyl-benzyloxy)-3-methoxy-phenyl]-methylidene]-2-thioxo-thiazolidin-4-one, (1.12 g, 2.27 mmol), iodomethane (5.5 mL, 88 mmol) and DMF (35 mL). The solution was al lowed to stir at 40° C. for 20 h. The reaction solution was concentrated under reduced pressure, and the residue was dissolved in MeCN (25 mL). To the mixture was added 1-methyl piperazine (0.76 mL, 6.8 mmol), and the solution was stirred at 65° C. for 2 h. The solution was then diluted with EtOAc (150 mL), washed with sat NH₄Cl (70 mL×2), dried over Na₂SO₄, filtered and concentrated. The crude material was chromatographed (SiO₂ DCM/MeOH 100:0 to 90:10) to provide the title product (470 mg, 37% yield). ¹H NMR (DMSO-d₆) δ 8.17 (1H, d, J=8.1 Hz), 8.11 (1H, s), 8.02 (1H, d, J=8.1 Hz), 7.61 (1H, s), 7.29 (1H, d, J=2.0 Hz), 7.20 (1H, dd, J=2.0 Hz, J₂=8.4 Hz), 7.14 (1H, d, J=8.4 Hz), 5.41 (2H, s), 3.90 (2H, t, J=4.8 Hz), 3.86 (3H, s), 3.65 (2H, t, J=4.8 Hz), 2.43-2.50 (4H, m), 2.24 (3H, s); ¹⁹F NMR (DMSO-d₆) d −59.5, −61.6; MS (ESI) 560 (MH⁺).

Example 19

Preparation of 5-[1-[4-(2,4-Bis-trifluoromethyl-benzyloxy)-3-methoxy-phenyl]-methylidene]-2-morpholin-4-yl-thiazol-4-one

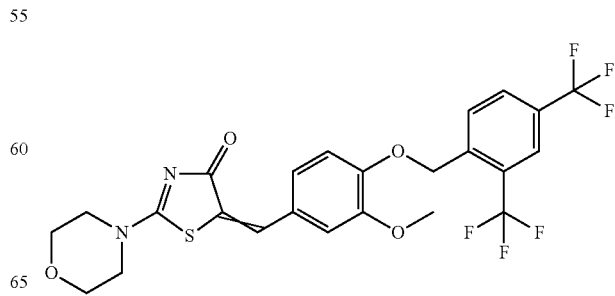

The title compound was prepared in a manner similar to that described in Example 18 by using morpholine in place of 1-methyl piperazine. MS (ESI) 547 (MH+).

Example 20

Preparation of 5-[1-[4-(2,4-Bis-trifluoromethyl-benzyloxy)-3-methoxy-phenyl]-methylidene]-2-(3,5-dimethyl-morpholin-4-yl)-thiazol-4-one

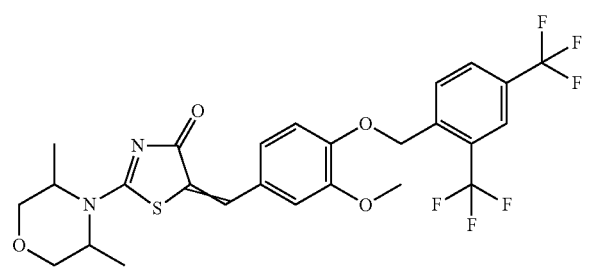

The title compound was prepared in a manner similar to that described in Example 18 by using 3,5-dimethyl morpholine in place of 1-methyl piperazine. MS (ESI) 575 (MH+).

Example 21

Preparation of 5-[1-[4-(2,4-Bis-trifluoromethyl-benzyloxy)-3-methoxy-phenyl]-methylidene]-2-piperidin-1-yl-thiazol-4-one

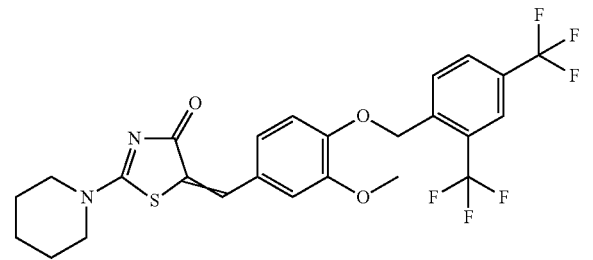

The title compound was prepared in a manner similar to that described in Example 18 by using piperidine in place of 1-methyl piperazine. MS (ESI) 545 (MH+).

Example 22

Preparation of 5-[1-[4-(2,4-Bis-trifluoromethyl-benzyloxy)-3-methoxy-phenyl]-methylidene]-2-thiomorpholin-4-yl-thiazol-4-one

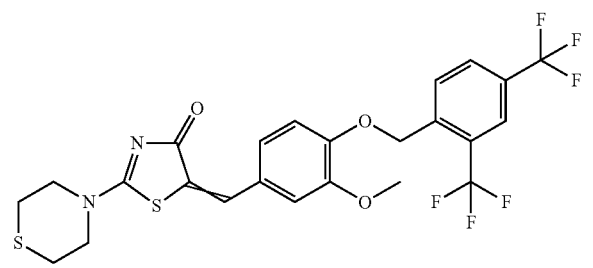

The title compound was prepared in a manner similar to that described in Example 18 by using thiomorpholine in place of 1-methyl piperazine. MS (ESI) 563 (MH+).

Example 23

Preparation of 5-[1-[4-(2,4-Bis-trifluoromethyl-benzyloxy)-3-methoxy-phenyl]-methylidene]-2-piperazin-1-yl-thiazol-4-one

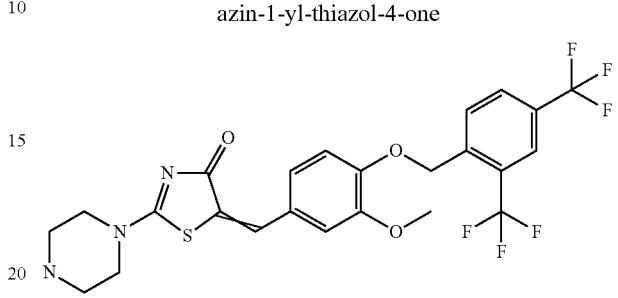

The title compound was prepared in a manner similar to that described in Example 18 by using piperazine in place of 1-methyl piperazine. MS (ESI) 546 (MH+).

Example 24

Preparation of 5-[1-[4-(2,4-Bis-trifluoromethyl-benzyloxy)-3-methoxy-phenyl]-methylidene]-2-(2-methyl-piperazin-1-yl)-thiazol-4-one

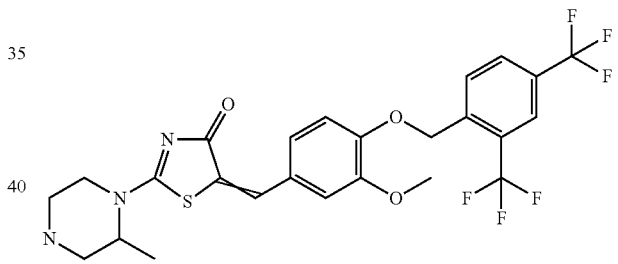

The compound was prepared in a manner similar to that described in Example 18 by using 2-methyl piperazine in place of 1-methyl piperazine. MS (ESI) 560 (MH+).

Example 25

Preparation of 5-[1-[4-(2,4-Bis-trifluoromethyl-benzyloxy)-3-methoxy-phenyl]-methylidene]-2-(4-pyridin-2-yl-piperazin-1-yl)-thiazol-4-one

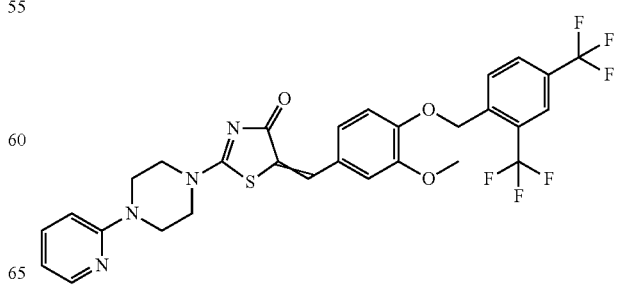

The title compound was prepared in a manner similar to that described in Example 18 by using 1-(2-pyridyl)-piperazine in place of 1-methyl piperazine. MS (ESI) 623 (MH+).

Example 26

Preparation of 5-[1-[4-(2,4-Bis-trifluoromethyl-benzyloxy)-3-methoxy-phenyl]-methylidene]-2-(4-phenyl-piperazin-1-yl)-thiazol-4-one

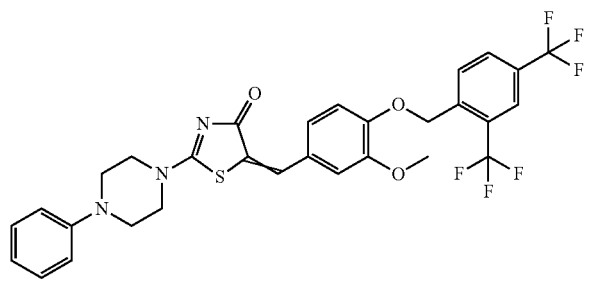

The title compound was prepared in a manner similar to that described in Example 18 by using 1-phenyl piperazine in place of 1-methyl piperazine. MS (ESI) 622 (MH+).

Example 27

Preparation of 5-[1-[4-(2,4-Bis-trifluoromethyl-benzyloxy)-phenyl]-methylidene]-2-(4-methyl-piperazin-1-yl)-thiazol-4-one

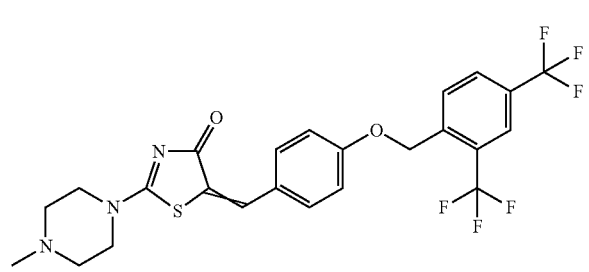

A. Preparation of 4-(2,4-trifluoromethyl benzyloxy)benzaldehyde

In a $N_2$-purged flask was added 4-hydroxy benzaldehyde (155 mg, 1.27 mmol), 2,4-bis trifluoromethyl benzyl chloride (390 mg, 1 equiv), DMF (9 mL) and $K_2CO_3$ (530 mg, 3.8 mmol). The reaction solution was allowed to stir at 60° C. under $N_2$ for 14 h. The reaction solution was diluted with EtOAc (150 mL), vacuum filtered to remove the $K_2CO_3$, washed with sat $NH_4Cl$ (30 mL×2), washed again with water (50 mL), dried over $Na_2SO_4$, filtered, and concentrated in vacuo to provide the crude product.

B. Preparation of 5-[1-[4-(2,4-bis-trifluoromethyl-benzyloxy)-phenyl]-methylidene]-2-thioxo-thiazolidin-4-one This intermediate was prepared in a manner similar to that described in Example 1B by replacing 4-(2,4-bis(trifluoromethyl)benzyloxy)-3-methoxybenzaldehyde with 4-(2,4-trifluoromethyl benzyloxy)benzaldehyde in Step A.

C. Preparation of Title Compound

The title compound was prepared in a manner similar to that described in Example 18, but replacing '5-[1-[4-(2,4-bis-trifluoromethyl-benzyloxy)-3-methoxy-phenyl]-methylidene]-2-thioxo-thiazolidin-4-one with 5-[1-[4-(2,4-Bis-trifluoromethyl-benzyloxy)-phenyl]-methylidene]-2-thioxo-thiazolidin-4-one from Step B to afford 45 mg, (33%) of title compound. $^1$H NMR (DMSO-$d_6$) δ 8.15 (1H, d, J=8.1 Hz), 8.11 (1H, s), 8.03 (1H, d, J=8.1 Hz), 7.62 (2H, d, J=8.5 Hz), 7.60 (1H, s), 7.16 (2H, d, J=8.5 Hz), 5.42 (2H, s), 3.90 (2H, t, J=4.7 Hz), 3.63 (2H, t, J=4.7 Hz), 2.43-2.50 (4H, m), 2.24 (3H, s); MS (ESI) 530 (MH+).

Example 28

Preparation of 2-(4-Acetyl-piperazin-1-yl)-5-[1-[4-(2,4-bis-trifluoromethyl-benzyloxy)-3-m ethoxy-phenyl]-methylidene]-thiazol-4-one

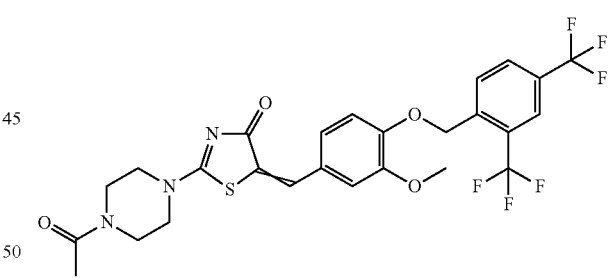

To a flask was added 5-[1-[4-(2,4-bis-trifluoromethyl-benzyloxy)-3-methoxy-phenyl]-methylidene]-2-piperazin-1-yl-thiazol-4-one (51, mg, 94 μL) from Example 23, chloroform (5 mL), acetyl chloride (1.5 equiv, 10 μL) and TEA (3 equiv, 40 μL). The reaction solution was stirred at 45° C. for 1.5 hours. The solution was then diluted with EtOAc (75 mL) and filtered through a Buchner funnel to remove excess $K_2CO_3$. The solution was washed with aq $NH_4Cl$ (50 ml×2), dried over $Na_2SO_4$, filtered, and concentrated in vacuo. The crude material was chromatographed ($SiO_2$, DCM/MeOH 100:0 to 94:06) to provide the title compound (19 mg, 40% yield). $^1$H NMR (CDCl$_3$) δ 7.95-7.97 (2H, m), 7.84 (2H, d, J=7.7 Hz), 7.77 (1H, s), 7.08-7.11 (2H, m), 6.87 (1H, d, J=8.2 Hz), 5.44

(2H, s), 4.09-4.11 (2H, m), 3.97 (3H, s), 3.79-3.81 (2H, m), 3.61-3.66 (4H, m), 2.17 (3H, s), 1.60 (3H, s); MS (ESI) 588 (MH+).

Example 29

Preparation of 5-[1-[4-(2,4-Bis-trifluoromethyl-benzyloxy)-3-methoxy-phenyl]-methylidene]-2-(4-methanesulfonyl-piperazin-1-yl)-thiazol-4-one

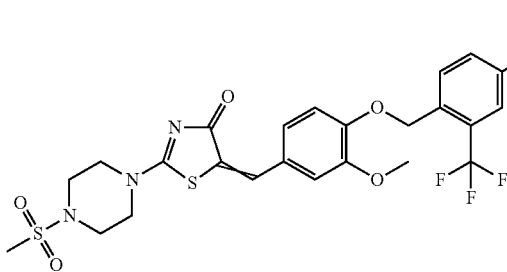

To a flask was added 5-[1-[4-(2,4-bis-trifluoromethyl-benzyloxy)-3-methoxy-phenyl]-methylidene]-2-piperazin-1-yl-thiazol-4-one (50 mg, 92 µmol) (from Example 23) chloroform (5 mL), methyl sulfonyl chloride (3 equiv, 32 µL) and TEA (3 equiv, 40 µL). The reaction was stirred at 60° C. under $N_2$. The reaction solution was diluted with DCM (70 mL), washed with aq $NH_4Cl$, dried over $Na_2SO_4$, filtered, and concentrated in vacuo. The crude material was chromatographed (SiO$_2$, DCM/MeOH 100:0 to 90:10) to provide the title compound as a white solid (30 mg, 52%). $^1$H NMR (DMSO-d$_6$) δ 7.99 (2H, s), 7.94 (1H, s), 7.62 (1H, s), 7.18 (1H, s), 7.13 (1H, dd, $J_1$=2.0 Hz, $J_2$=8.4 Hz), 7.01 (1H, d, J=8.4 Hz), 5.37 (2H, s), 4.06 (2H, m), 3.88 (3H, s), 3.74 (2H, m), 3.31-3.36 (4H, m), 2.85 (3H, s); MS (ESI) 624 (MH+).

Example 30

Preparation of 4-{5-[1-[4-(2,4-Bis-trifluoromethyl-benzyloxy)-3-methoxy-phenyl]-methylidene]-4-oxo-4,5-dihydro-thiazol-2-yl}-piperazine-1-carbothioic acid (4-methoxy-phenyl)-amide

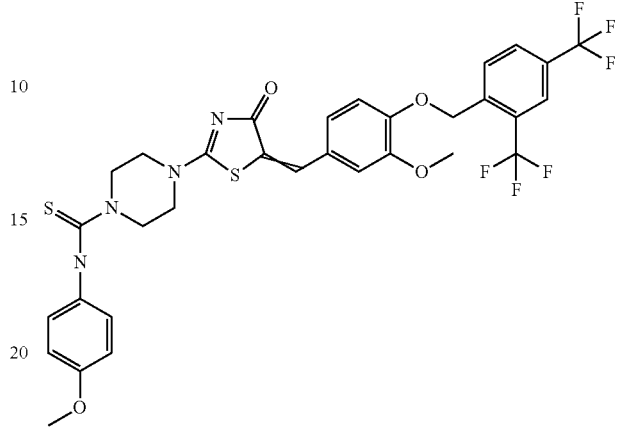

To a $N_2$ purged flask was added 5-[1-[4-(2,4-bis-trifluoromethyl-benzyloxy)-3-methoxy-phenyl]-methylidene]-2-piperazin-1-yl-thiazol-4-one (120 mg, 220 µmol) from Example 23, DMF (8 mL) and MeCN (8 mL). To the reaction solution was added 4-methoxylphenyl isothiocyanate (55 mg, 330 µmol). The reaction was stirred at 55° C. for 20 h and LC analysis should product was formed. The reaction solution was concentrated under reduced pressure and then taken into EtOAc (100 mL), washed with aq. NH4Cl (70 mL) and brine (50 mL), dried over Na2SO4, filtered, and concentrated in vacuo. The crude material was chromatographed using reverse phase preparative HPLC, H$_2$O/MeCN gradient 90:10 to 10:90) to provide the title compound as a white solid (24 mg, 13% yield). $^1$H NMR (DMSO-d$_6$) δ 8.17 (1H, d, J=8.1 Hz), 8.11 (1H, s), 8.02 (1H, d, J=8.1 Hz), 7.64 (1H, s), 7.15-7.23 (5H, m), 6.88 (2H, d, J=8.9 Hz), 5.42 (2H, s), 4.16 (2H, br s), 4.09 (2H, m), 4.03 (2H, m), 3.86 (3H, s), 3.80 (2H, m), 3.74 (3H, s); MS (ESI) 711 (MH+).

Example 31

Preparation of 4-{5-[1-[4-(2,4-Bis-trifluoromethyl-benzyloxy)-3-methoxy-phenyl]-7-methylidene]-4-oxo-4,5-dihydro-thiazol-2-yl}-piperazine-1-carbothioic acid phenethyl-amide

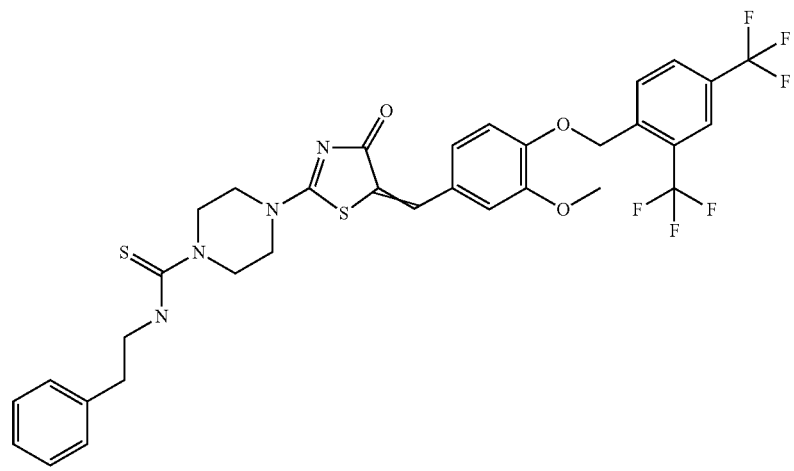

The title compound was prepared in a manner similar to that described in Example 30 by using phenylethyl isothiocyanate in place of 4-methoxyphenyl isothiocyanate. MS (ESI) 709 (MH+).

Example 32

Preparation of 5-[(4-{5-[1-[4-(2,4-Bis-trifluoromethyl-benzyloxy)-3-methoxy-phenyl]-methylidene]-4-oxo-4,5-dihydro-thiazol-2-yl}-piperazine-1-carbothioyl)-amino]-2-(6-hydroxy-3-oxo-3H-xanthen-9-yl)-benzoic acid

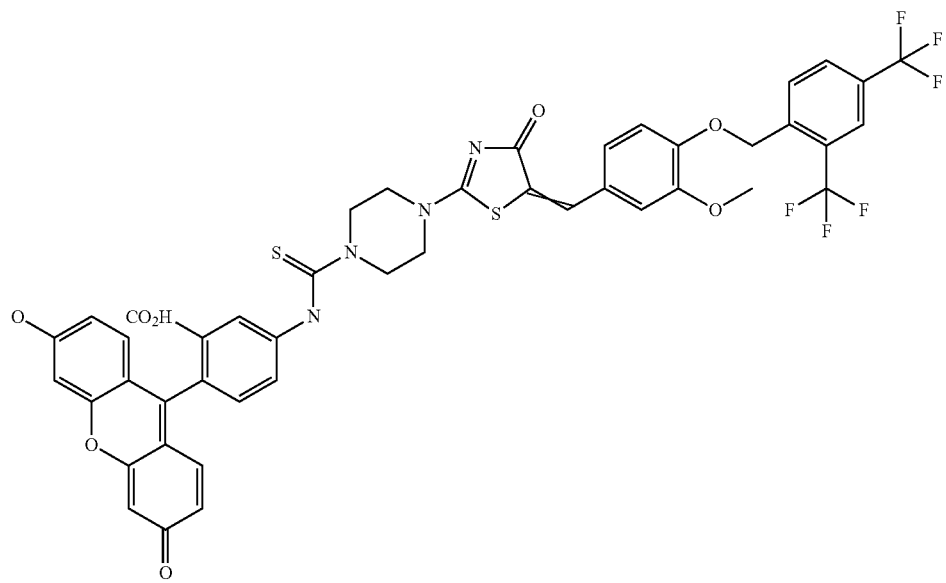

The title compound was prepared in a manner similar to that described in Example 30 by using fluorescien isothiocyanate in place of 4-methoxyphenyl isothiocyanate. MS (ESI) 935 (MH+).

Example 33

Preparation of 5-[1-[4-(2,4-Bis-trifluoromethyl-benzyloxy)-3-methoxy-phenyl]-ethylidene]-2-(4-methyl-piperazin-1-yl)-thiazol-4-one

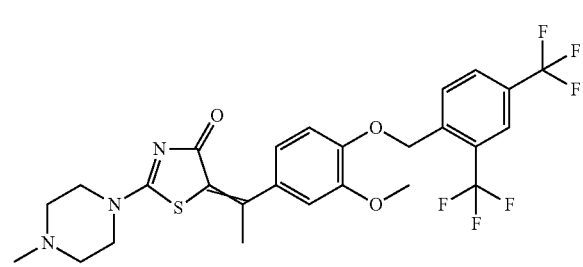

A. Preparation of intermediate 1-[4-(2,4-Bis-trifluoromethyl-benzyloxy)-3-methoxy-phenyl]-ethanone To a $N_2$ purged flask was added 2,4-bis-trifluoromethyl benzyl bromide (2.21 g, 7.20 mmol), acetovanillone (1.32 g, 7.92 mmol), and DMF (15 mL). To the reaction solution was added fine mesh $K_2CO_3$ (3 equiv, 21.6 mmol). The reaction was allowed to stir at 70° C. for 1 h, then at 60° C. for 14 h. The reaction solution was then diluted with EtOAc (150 mL), filtered through a Buchner funnel, washed with sat'd $NH_4Cl$ (70 mL×2) washed with sat NaCl (50 mL), dried over $Na_2SO_4$, and then filtered and concentrated in vacuo to provide a crude product (2.8 g, 99% yield).

B. Preparation of intermediate 5-[1-[4-(2,4-Bis-trifluoromethyl-benzyloxy)-3-methoxy-phenyl]-ethylidene]-2-thioxo-thiazolidin-4-one To a flask with a stir bar and attached to a condenser, was added 1-[4-(2,4-Bis-trifluoromethyl-benzyloxy)-3-methoxy-phenyl]-ethanone from Step A (244 mg, 622 μmol), rhodanine (133 ng, 1.0 mmol), $NH_4OAc$ (77 mg, 1.0 mmol) and toluene (5 mL). The reaction mixture was heated to reflux and stirred for 8 h at reflux. Additional $NH_4OAc$ (50 mg) and toluene (2 mL) was added to the mixture and allowed to reflux for an additional 24 hours. The reaction solution was then diluted with EtOAc (75 mL), washed with $NH_4Cl$ (50 mL×3), dried over $Na_2SO_4$, filtered, and concentrated in vacuo. The crude material was chromatographed (TLC, DCM/EtOAc 100:0 to 85:15) to provide the intermediate compound. (195 mg, 62% yield).

C. Preparation of Title Compound

To a $N_2$-purged flask was added 5-[1-[4-(2,4-Bis-trifluoromethyl-benzyloxy)-3-methoxy-phenyl]-ethylidene]-2- thioxo-thiazolidin-4-one from Step B, anhydrous MeCN (5 mL), and iodomethane (3.5 mL). The reaction solution was stirred under dry N₂ at 40° C. for 3.5 h. The solvent was removed in vacuo and the resulting yellow solid was redissolved in anhydrous MeCN. 1-Methyl piperazine was added to the solution, followed by DMF (0.5 mL) for better dissolution. The solution was stirred at 65° C. for 3.5 h. The reaction solution was then diluted with EtOAc (50 mL). The precipitated 1-methyl piperazine was removed. The solution was concentrated in vacuo and chromatographed (SiO₂, DCM (with 0.2% TEA)/MeOH 100:0 to 92:8). The product, isolated as a viscous oil, was reprecipitated by adding to cold hexane. (43 mg, 28% yield). ¹H NMR (DMSO-d₆) δ 8.17 (1H, d, J=8.1 Hz), 8.10 (1H, s), 8.04 (1H, d, J=8.1 Hz), 7.07-7.10 (2H, m), 6.99 (1H, dd, J₁=2.0 Hz, J₂=8.3 Hz), 5.36 (2H, s), 3.81 (5H, br s), 3.41 (2H, t, J=4.4 Hz), 2.64 (3H, s), 2.39 (4H, br s), 2.21 (3H, s); ¹⁹F NMR (DMSO-d₆) d −59.4, −61.4; MS (ESI) 574 (MH⁺).

Example 34

Preparation of 5-[4-(2,4-Bis-trifluoromethyl-benzyloxy)-3-methoxy-benzyl]-2-(4-methyl-piperazin-1-yl)-thiazol-4-one

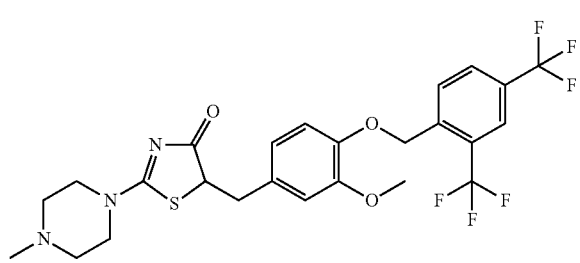

A. Preparation of intermediate 5-[4-(2,4-bis-trifluoromethyl-benzyloxy)-3-methoxy-benzyl]-2-thioxothiazolidin-4-one To a N₂-purged flask was added '5-[1-[4-(2,4-bis-trifluoromethyl-benzyloxy)-3-methoxy-phenyl]-methylidene]-2-thioxo-thiazolidin-4-one (42 mg, 85 µmol) and DME (4 mL). To the solution was added NaBH₃CN (20 mg, 255 µmol) followed by acetic acid (2 mL). The reaction was stirred at rt for 2 h. The reaction solution was then diluted with EtOAc (100 mL), neutralized by successive washings of sat NaHCO₃ (100 mL×3), washed with sat. NaCl (100 mL), dried over Na₂SO₄, filtered and concentrated under reduced pressure. The crude material was chromatographed (SiO₂, DCM/MeOH 100:0 to 98:2) to provide intermediate compound (155 mg, 50% yield). ¹H NMR (CDCl₃) δ 9.29 (1H, br s), 7.99 (1H, d, J=8.1 Hz), 7.94 (1H, s), 7.83 (1H, d, J=8.1 Hz), 6.72-6.81 (3H, m), 5.38 (2H, s), 4.60 (1H, dd, J₁=3.9 Hz, J₂=9.8 Hz), 3.92 (3H, s), 3.48 (1H, dd, J=3.9 Hz, J₂=14.2 Hz), 3.14 (1H, m); MS (ESI) 496 (MH⁺).

B. Preparation of Title Compound

To a flask was added 5-[4-(2,4-bis-trifluoromethyl-benzyloxy)-3-methoxy-benzyl]-2-thioxo-thiazolidin-4-one from Step A (140 mg, 282 µmol), DMSO (1 mL) and iodomethane (2 mL). The reaction solution was allowed to stir under N₂ for 3 h. The excess iodomethane was removed in vacuo. To the reaction mixture was added MeCN (6 mL) and N-methyl piperazine (95 µL, 850 µmol). The reaction solution was stirred at 55° C. for 2 h. The reaction solution was then diluted with EtOAc (200 mL), washed with aq. NH₄Cl and water, dried over Na₂SO₄ and concentrated. The crude material was chromatographed (SiO₂, DCM/MeOH 100:0 to 90:10) to provide title compound (55 mg, 35% yield). ¹H NMR (CDCl₃) δ 8.10 (1H, d, J=8.1 Hz), 7.92 (1H, s), 7.83 (1H, d, J=8.1 Hz), 6.83 (1H, s), 6.73 (2H, br s), 5.36 (2H, s), 4.46 (1H, dd, J₁=3.6 Hz, J₂=10.4 Hz), 3.96 (2H, t, J=4.9 Hz), 3.90 (3H, s), 3.57 (1H, dd, J=3.6 Hz, J₂=14.3 Hz), 3.49 (2H, t, J=4.9 Hz), 2.92 (1H, dd, J₁=10.4 Hz, J₂=14.3 Hz), 2.46 (4H, m), 2.32 (3H, s); MS (ESI) 562 (MH⁺).

Example 35

Preparation of '5-[1-[3-Methoxy-4-(2-methoxy-ethoxy)-phenyl]-methylidene]-2-(4-methyl-piperazin-1-yl)-thiazol-4-one

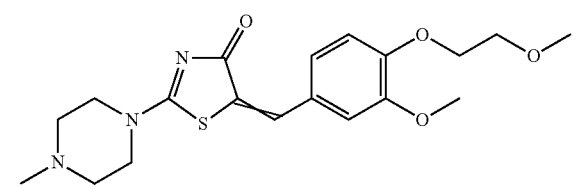

A. Preparation of 3-methoxy-4-(2-methoxy-ethoxy)-benzaldehyde

To a flask was added vanillin (3.28 g, 21.6 mmol) and 2-bromoethyl methyl ether (3.04 mL, 1.5 equiv) in a solution of DMF (20 mL). K₂CO₃ (5.5 g, 2 equiv) was then added to the solution and the reaction slurry was stirred at 90° C. for 16 h under N₂. The reaction solution was diluted with EtOAc (100 mL), filtered, washed with sat NH₄Cl, dried over Na₂SO₄, filtered and concentrated in vacuo. The crude material was chromatographed (SiO₂, Hex/EtOAc 100:D to 70:30) to afford the intermediate compound.

B. Preparation of 5-[1-[3-methoxy-4-(2-methoxy-ethoxy)-phenyl]-methylidene]-2-thioxothiazolidin-4-one To a N₂-purged flask was added 3-methoxy-4-(2-methoxy-ethoxy)-benzaldehyde from Step A (162 mg, 771 mmol), rhodanine (103 mg, 1 equiv), NaOAc (190 mg, 2.31 mmol) and HOAc (3 mL). The mixture was stirred and heated at 90° C. for 14 h under a condenser, resulting in a yellow precipitate. The reaction mixture was diluted with water (100 mL) and the solid precipitate was filtered in a Buchner funnel. The solid was washed with water, washed with hexane, and dried under high vacuum to yield the intermediate compound (179 mg, 72% yield).

C. Preparation of Title Compound

To a N₂-purged flask was added 5-[1-[3-methoxy-4-(2-methoxy-ethoxy)-phenyl]-methylidene]-2-thioxothiazolidin-4-one from Step B (77 mg, 237 μmol), anhydrous DMF (5 mL) and iodomethane (1 mL). The reaction solution was stirred at 40° C. for 24 h followed by a removal of the iodomethane and DMF in vacuo. To the residual material was added MeCN (5 mL) and DMF (0.5 mL) followed by the addition of 1-methyl piperazine. The reaction solution was stirred at 65° C. for 3 h. The reaction solution was diluted with EtOAc (70 mL), washed with sat NH$_4$Cl (40 mL×2), washed with aq NaHCO$_3$ (40 mL), and then with water (30 mL), dried over Na$_2$CO$_3$, filtered and concentrated in vacuo. The crude material was chromatographed (SiO$_2$, DCM/MeOH 100:0 to 92:8) to afford the title compound (28 mg, 33% yield). $^1$H NMR (CDCl$_3$) δ 7.75 (1H, s), 7.12 (1H, dd, J$_1$=2.0 Hz, J$_2$=8.4 Hz), 7.03 (1H, d, J=2.0 Hz), 6.96 (1H, d, J=8.4 Hz), 4.21 (2H, dd, J=4.8 Hz, J$_2$=5.9 Hz), 4.08 (2H, t, J=4.8 Hz), 3.90 (3H, s), 3.80 (2H, dd, J=4.8 Hz, J$_2$=5.9 Hz), 3.63 (2H, t, J=4.8 Hz), 3.45 (3H, s), 2.52-2.57 (4H, m), 2.36 (3H, s); MS (ESI) 392 (MH$^+$).

Example 36

Preparation of '5-[1-(4-Hydroxy-3-methoxy-phenyl)-methylidene]-2-(4-methyl-piperazin-1-yl)-thiazol-4-one

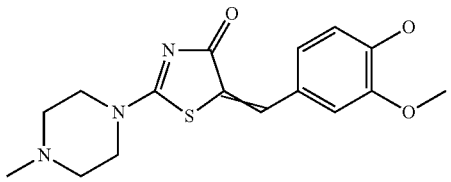

A. Preparation of 5-[1-(4-hydroxy-3-methoxy-phenyl)-methylidene]-2-thioxo-thiazolidin-4-one To a N$_2$-purged flask was added rhodanine (574 mg, 4.31 mmol), vanillin (656 mg, 1 equiv), NaOAc (354 mg, 3.5 equiv) and acetic acid (8.5 mL). The mixture was heated at 90° C. under N$_2$ for 20 h to yield a yellow precipitate. The reaction solution was diluted with water (150 mL) and the solid precipitate was filtered through a Buchner funnel. The solid product was washed with water, and then with hexane, then dried under high vacuum to yield the intermediate compound (770 mg, 67% yield).

B. Preparation of Title Compound

To a flask was added 5-[1-(4-hydroxy-3-methoxy-phenyl)-methylidene]-2-thioxo-thiazolidin-4-one (760 mg, 2.84 mmol), DMF (7.0 mL) and iodomethane (5.0 mL). The reaction solution was allowed to stir under N$_2$ for 4 h. The solvent and excess iodomethane was removed in vacuo. To the yellow residue was added MeCN (13 mL) and 1-methyl piperazine (570 mg, 630 μL), and the solution was stirred at 55° C. under N$_2$ for 2.5 h. The reaction solution was diluted with EtOAc (200 mL), washed with aq NH$_4$Cl, and then water and dried over conc. Na$_2$SO$_4$. The crude material was chromatographed (SiO$_2$, DCM/MeOH 100:0 to 92:8) to provide title compound (430 mg, 45%). $^1$H NMR (CDCl$_3$) δ 7.74 (1H, s), 7.12 (1H, dd, J$_1$=2.0 Hz), J$_2$=8.3 Hz), 6.97-7.01 (2H, m), 5.97 (1H, br s), 4.08 (2H, t, J=5.1 Hz), 3.94 (3H, s), 3.64 (2H, t, J=5.1 Hz), 2.52-2.58 (4H, m), 2.36 (3H, s); MS (ESI) 334 (MH$^+$).

Example 37

Preparation of '5-[1-(4-Benzyloxy-3-methoxy-phenyl)-methylidene]-2-(4-methyl-piperazin-1-yl)-thiazol-4-one

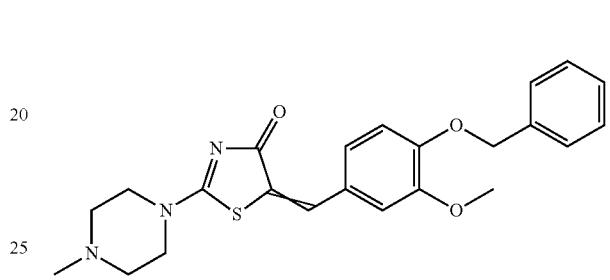

To a N$_2$-purged flask was added '5-[1-(4-Hydroxy-3-methoxy-phenyl)-methylidene]-2-(4-methyl-piperazin-1-yl)thiazol-4-one (57 mg, 0.17 mmol), MeCN (5 mL), benzyl chloride (30 μL, 1.5 equiv), and K$_2$CO$_3$ (70 mg, 3 equiv). The reaction mixture was stirred at 70° C. for 6 h. The reaction mixture was diluted with EtOAc (100 mL), and the excess K$_2$CO$_3$ was removed by filtration through a fritted glass funnel. The product solution was washed with aq NH$_4$Cl (50 mL×2) and H$_2$O (50 mL). The organic phase was dried over Na$_2$SO$_4$, filtered, and concentrated under reduced pressure. The crude product was chromatographed (SiO$_2$, DCM/MeOH 100:0 to 92:8) to provide pure title compound (20 mg, 28% yield). $^1$H NMR (DMSO-d$_6$) δ 7.66 (1H, s), 7.44-7.52 (5H, m), 7.29 (1H, s), 7.23-724 (2H, m), 5.22 (2H, s), 3.96 (2H, t, J=4.6 Hz), 3.89 (3H, s), 3.70 (2H, t, J=4.6 Hz), 2.48-2.52 (4H, m), 2.29 (3H, s); MS (ESI) 424 (MH$^+$).

Example 38

Preparation of '5-[1-[4-(2-Fluoro-benzyloxy)-3-methoxy-phenyl]-methylidene]-2-(4-methyl-piperazin-1-yl)-thiazol-4-one

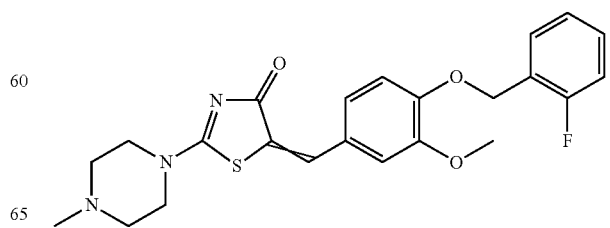

The title compound was prepared in a manner similar to that described in Example 37 by substituting benzyl chloride with 2-fluoro benzyl chloride. MS (ESI) 442 (MH+).

Example 39

Preparation of '5-[1-[3-Methoxy-4-(2-trifluoromethyl-benzyloxy)-phenyl]-methylidene]-2-(4-methyl-piperazin-1-yl)-thiazol-4-one

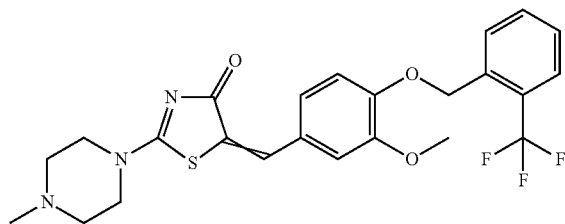

The title compound was prepared in a manner similar to that described in Example 37 by substituting benzyl chloride with 2-trifluoromethyl benzyl chloride. MS (ESI) 492 (MH+).

Example 40

Preparation of '5-[1-[4-(4-Fluoro-benzyloxy)-3-methoxy-phenyl]-methylidene]-2-(4-methyl-piperazin-1-yl)-thiazol-4-one

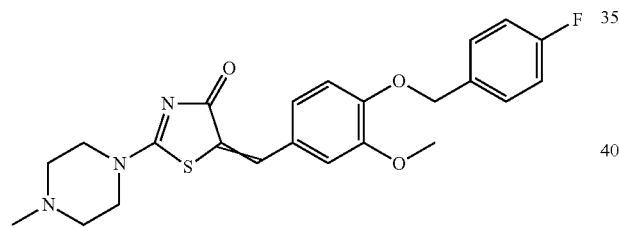

The title compound was prepared in a manner similar to that described in Example 37 by substituting benzyl chloride with 4-fluoro benzyl bromide. MS (ESI) 442 (MH+).

Example 41

Preparation of '5-[1-[3-Methoxy-4-(4-trifluoromethyl-benzyloxy)-phenyl]-methylidene]-2-(4-methyl-piperazin-1-yl)-thiazol-4-one

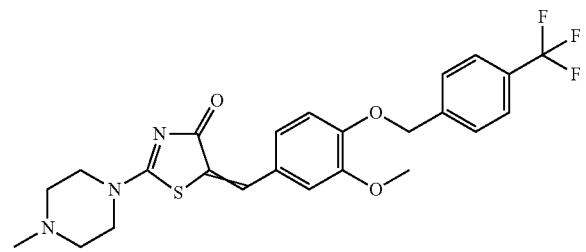

The title compound was prepared in a manner similar to that described in Example 37 by substituting benzyl chloride with 4-trifluoromethyl benzyl bromide. MS (ESI) 492 (MH+).

Example 42

Preparation of '2-{2-Methoxy-4-[2-(4-methyl-piperazin-1-yl)-4-oxo-4H-thiazolylidenemethyl]-phenoxymethyl}-benzonitrile

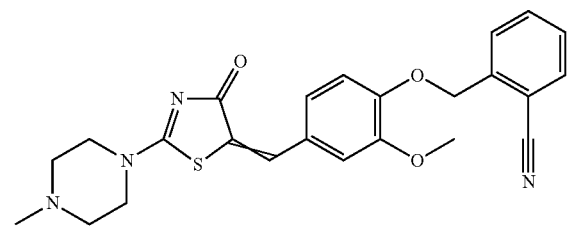

The title compound was prepared in a manner similar to that described in Example 37 by substituting benzyl chloride with 2-cyanobenzyl bromide. MS (ESI) 449 (MH+).

Example 43

Preparation of '5-[1-(3-Methoxy-4-phenethyloxy-phenyl)-methylidene]-2-(4-methyl-piperazin-1-yl)-thiazol-4-one

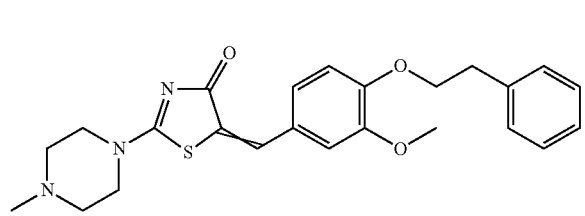

The title compound was prepared in a manner similar to that described in Example 37 by substituting benzyl chloride with 2-phenyl-chloroethane. MS (ESI) 438 (MH+).

Example 44

Preparation of 5-[1-[3-Methoxy-4-(4,4,4-trifluoro-butoxy)-phenyl]-methylidene]-2-(4-methyl-piperazin-1-yl)-thiazol-4-one

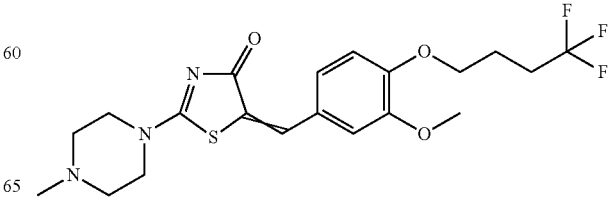

The title compound was prepared in a manner similar to that described in Example 37 by substituting benzyl chloride with 4-chloro-1,1,1-trifluorobutane. MS (ESI) 444 (MH+).

Example 45

Preparation of '5-[1-(2-Methoxy-4'-methyl-biphenyl-4-yl)-methylidene]-2-(4-methyl-piperazin-1-yl)-thiazol-4-one

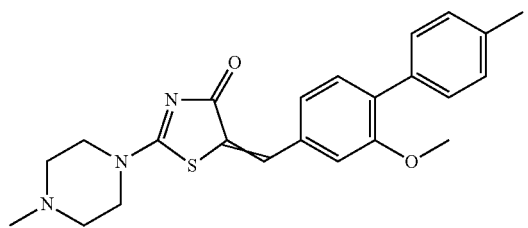

A. Preparation of Triflate Intermediate

To a flask was added '5-[1-(4-Hydroxy-3-methoxy-phenyl)-methylidene]-2-(4-methyl-piperazin-1-yl)-thiazol-4-one (200 mg, 600 μmol) (Example 36) and 1-methyl piperazine (3 mL). The solution was cooled to 0° C. in an ice bath prior to the addition of triflic anhydride (150 μL, 900 μmol). The reaction solution was quenched with the addition of water (20 mL). The reaction solution was diluted with EtOAc (30 mL), and diethylether (50 mL). The aqueous phase was removed and the organic phase was washed with 10% aq. HCl, then with sat. NaCl (40 mL) and dried over $Na_2SO_4$. The solution was filtered and concentrated in vacuo to yield a crude product to be used in the next step.

B. Preparation of Title Compound

To a $N_2$-purged flask was added the triflate intermediate from Step A (300 μmol), 4-methyl phenyl boric acid (82 mg, 600 μmol), Pd(PPh$_3$)$_4$ (34 mg, 10 mol %), $K_2CO_3$ (160 mg, 1.2 mmol), KBr (26 mg, 1 equiv), DME (5 mL), and $H_2O$ (3 mL). The reaction mixture was stirred at 90° C. for approximately 20 h. The reaction solution was then diluted with EtOAc (50 mL), passed through Celite, washed with aq. NH$_4$Cl and brine, dried over $Na_2SO_4$, filtered and concentrated in vacuo. The crude material was chromatographed (SiO$_2$, DCM/MeOH 100:0 to 92:8) to provide the title compound (103 mg, 93%). $^1$H NMR (CDCl$_3$) δ 7.76 (1H, s), 7.37 (2H, d, J=8.1 Hz), 7.31 (2H, d, J=8.1 Hz), 7.13-7.20 (3H, m), 7.03 (1H, s), 4.04 (2H, t, J=4.8 Hz), 3.79 (3H, s), 3.58 (2H, t, J=4.8 Hz), 2.46-2.51 (4H, m), 2.32 (3H, s), 2.26 (3H, s); MS (ESI) 408 (MH+).

Example 46

Preparation of '5-[1-(2-Methoxy-2',4'-dimethyl-biphenyl-4-yl)-methylidene]-2-(4-methyl-piperazin-1-yl)-thiazol-4 one

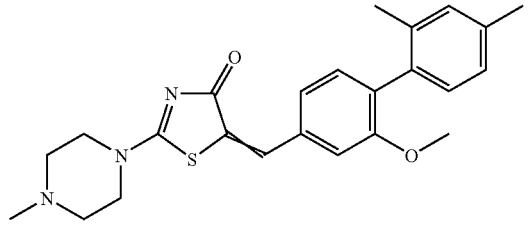

The title compound was prepared in a manner similar to that described in Example 45 by using 2,4 dimethyl phenyl boronic acid in place of 4-methyl phenyl boronic acid. MS (ESI) 422 (MH+).

Example 47

Preparation of 5-[1-(2-Methoxy-2'-trifluoromethyl-biphenyl-4-yl)-methylidene]-2-(4-methyl-piperazin-1-yl)-thiazol-4-one

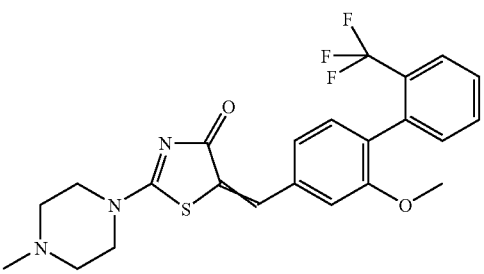

A. Preparation of 5-[1-(2-Methoxy-2'-trifluoromethyl-biphenyl-4-yl)-methylidene]-2-thioxo-thiazolidin-4-one To a flask was added rhodanine (37 mg, 275 μmol), 2-Methoxy-2'-trifluoromethyl-biphenyl-4-carboxaldehyde (70 mg, 250 μmol), acetic acid (4 mL) and NaOAc (60 mg, 3 equiv). The reaction solution was allowed to stir at 95° C. under $N_2$ for 14 h. Additional NaOAc (60 mg, 3 equiv) was added to the solution and stirred at 100° C. for an additional 24 h. The reaction solution was diluted with EtOAc (100 mL), washed with water (50 mL×3), washed with aq NaHCO$_3$ (50 mL×3), dried and concentrated. The crude material was chromatographed (SiO$_2$, Hex:EtOAc 100:0 to 70:30) to yield the intermediate compound. (79 mg, 80%).

B. Preparation of Title Compound

To a $N_2$-purged flask was added 5-[1-(2-Methoxy-2-trifluoromethyl-biphenyl-4-yl)-methylidene]-2-thioxo-thiazolidin-4-one from Step A (70 mg, 0.18 mmol), iodomethane (1.5 mL) and CHCl$_3$ (0.4 mL). The reaction solution was stirred at 40° C. for 14 h prior to concentration in vacuo. The residue was dissolved in anhydrous MeGN (5 mL) and 3 equivalents of 1-methyl piperazine was added (60 μl, 0.54 mmol). The reaction solution was stirred at 60° C. for 2.5 h. The reaction solution was diluted with EtOAc (60 mL), washed with aq NH$_4$Cl (30 mL×2), dried over Na$_2$SO$_4$, filtered, and concentrated in vacuo. The crude material was chromatographed (SiO$_2$, DCM:MeOH 100:0 to 92:8) to yield the title compound (49 mg, 59%). $^1$H NMR (CDCl$_3$) δ 7.84 (1H, s), 7.75 (1H, d, J=7.7 Hz), 7.57 (1H, t, J=7.4 Hz), 7.48 (1H, t, J=7.6 Hz), 7.17-7.29 (3H, m), 7.07 (1H, s), 4.10 (2H, t, J=4.7 Hz), 3.77 (3H, s), 3.65 (2H, t, J=4.7 Hz), 2.53-2.59 (4H, m), 2.36 (3H, s); $^{19}$F NMR (CDCl$_3$) δ −59.4; MS (ESI) 462 (MH$^+$).

Example 48

Preparation of 5-[1-[4-(2,4-Bis-trifluoromethyl benzyloxy)-3-methoxy-phenyl]-meth-(E)-ylidene]-2-[4-(furan-2-carbonyl)-piperazin-1-yl]-thiazol-4-one

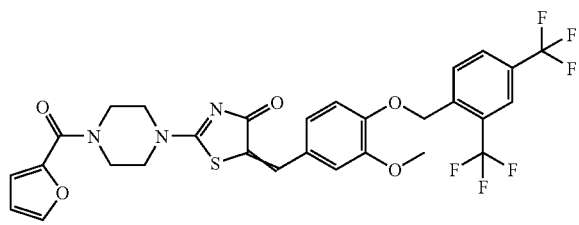

Into a 4 mL round-bottom vial was weighed 0.12 g of 5-[1-[4-(2,4-Bistrifluoromethyl-benzyloxy)-3-methoxy-phenyl]-methyl-(E)-ylidene]-2-methylsulfanyl-thiazol-4-one (0.25 mmol), 0.045 g (0.25 mmol) of 1-(2-Furoyl)piperazine, and 3 mL of DMF:THF (2:1). The resulting solution was heated to 60° C. for 3 h then the reaction was cooled and concentrated in vacuo. The resulting residue was purified by flash chromatography (SiO2), eluting with EtOAc/Hex 30-80% to afford the title compounds as a yellow solid (12 mg, 8%); $^1$H NMR (DMSO-d$_6$): δ 8.07 (d, 1H, 8 Hz), 8.00 (s, 1H), 7.92 (d, 1H, 8 Hz), 7.79 (m, 1H) 7.54 (s, 1H), 7.21 (d, 2 Hz, 1H), 7.13-7.04 (m, 2H), 6.99 (s, 1H), 6.57 (m, 1H), 5.31 (s, 2H), 3.95-3.65 (m, 11H); MS (ESI) m/z 640 [M+H]$^+$ The following compounds were prepared in a similar manner:

3-{5-[1-[4-(2,4-Bis-trifluoromethyl-benzyloxy)-3-methoxy-phenyl]-meth-(E)-ylidene]-4-oxo-4,5-dihydro-thiazol-2-ylamino}-benzoic acid ethyl ester; Yellow Solid (15 mg, 10%); $^1$H NMR (DMSO-d$_6$): δ 8.10 (m, 1H), 8.06 (d, 1H, 8 Hz), 8.00-7.94 (m, 2H), 7.90 (s, 1H), 7.87-7.80 (m, 2H) 7.57 (d, 1H, 2 Hz), 7.45 (t, 1H, 8 Hz), 7.35 (dd, 1H, 2.8 Hz), 6.86 (d, 1H, 8 Hz), 5.45 (s, 2H), 4.38 (q, 2H, 7 Hz), 4.00 (s, 3H) 1.40 (t, 3H, 7 Hz); MS (ES): 625 (MH+);

5-[1-[4 (2,4-Bis-trifluoromethyl-benzyloxy)-3-methoxy-phenyl]-methylidene]-2-(2-pyridin-2-yl-pyrrolidin-1-yl)-thiazol-4-one; MS (ES): 608 (MH+);

5-[1-[4-(2,4-Bis-trifluoromethyl-benzyloxy)-3-methoxy-phenyl]-methylidene]-2-(1-ethyl-3,4-dihydro-1H-pyrrolo[1,2-a]pyrazin-2-yl)-thiazol-4-one; MS (ES): 610 (MH+);

5-[1-[4-(2,4-Bis-trifluoromethyl-benzyloxy)-3-methoxy-phenyl]-methylidene]-2-(3-pyridin-3-yl-pyrrolidin-1-yl)-thiazol-4-one; MS (ES): 608 (MH+);

5-[1-[4-(2,4-Bis-trifluoromethyl-benzyloxy)-3-methoxy-phenyl]-methylidene]-2-[2-(5-fluoro-1H-benzoimidazol-2-yl)-pyrrolidin-1-yl]-thiazol-4-one; MS (ES): 665 (MH+);

5-[1-[4-(2,4-Bis-trifluoromethyl-benzyloxy)-3-methoxy-phenyl]-methylidene]-2-[3-(pyridine-3-carbonyl)-piperidin-1-yl]-thiazol-4-one; MS (ES): 650 (MH+);

5-[1-[4-(2,4-Bis-trifluoromethyl-benzyloxy)-3-methoxy-phenyl]-methylidene]-2-[4-(4-hydroxy-phenyl)-piperazin-1-yl]-thiazol-4-one; MS (ES): 638 (MH+);

5-[1-[4-(2,4-Bis-trifluoromethyl-benzyloxy)-3-methoxy-phenyl]-methylidene]-2-[4-(2,4-difluoro-phenyl)-piperazin-1-yl]-thiazol-4-one; MS (ES): 658 (MH+);

5-[1-[4-(2,4-Bis-trifluoromethyl-benzyloxy)-3-methoxy-phenyl]-methylidene]-2-[4-(hydroxy-pyridin-3-yl-methyl)piperidin-1-yl]-thiazol-4-one; MS (ES): 652 (MH+);

5-[1-[4-(2,4-Bis-trifluoromethyl-benzyloxy)-3-methoxy-phenyl]-methylidene]-2-[4-(2-methyl-quinolin-4-yl)-piperazin-1-yl]-thiazol-4-one; MS (ES): 687 (MH+);

5-[1-[4-(2,4-Bis-trifluoromethyl-benzyloxy)-3-methoxy-phenyl]-methylidene]-2-(3-pyridin-2-yl-pyrrolidin-1-yl)-thiazol-4-one; MS (ES): 608 (MH+);

5-[1-[4-(2,4-Bis-trifluoromethyl-benzyloxy)-3-methoxy-phenyl]methylidene]-2-[4-(2-methyl-thiazol-4-ylmethyl)-piperazin-1-yl]-thiazol-4-one; MS (ES). 657 (MH+);

5-[1-[4-(2,4-Bis-trifluoromethyl-benzyloxy)-3-methoxy-phenyl]-methylidene]-2-(4-thiophen-2-ylmethyl-piperazin-1-yl)-thiazol-4-one; MS (ES): 642 (MH+);

5-[1-[4-(2,4-Bis-trifluoromethyl-benzyloxy)-3-methoxy-phenyl]-methylidene]-2-(1-methyl-3,4-dihydro-1H-pyrrolo[1,2-a]pyrazin-2-yl)-thiazol-4-one; MS (ES): 596 (MH+);

5-[1-[4-(2,4-Bis-trifluoromethyl-benzyloxy)-3-methoxy-phenyl]-methylidene]-2-(2-pyridin-3-yl-pyrrolidin-1-yl)-4-thiazol-4-one; MS (ES): 608 (MH+);

5-[1-[4-(2,4-Bis-trifluoromethyl-benzyloxy)-3-methoxy-phenyl]-methylidene]-2-[4-(2,3-dimethyl-phenyl)-piperazin-1-yl]-thiazol-4-one; MS (ES): 650 (MH+);

5-[1-[4-(2,4-Bis-trifluoromethyl-benzyloxy)-3-methoxy-phenyl]-methylidene]-2-[4-(2,5-dimethyl-phenyl)-piperazin-1-yl]-thiazol-4-one; MS (ES): 650 (MH+);

5-[1-[4-(2,4-Bis-trifluoromethyl-benzyloxy)-3-methoxy-phenyl]-methylidene]-2-[4-(4-chloro-benzyl)-piperazin-1-yl]-thiazol-4-one; MS (ES): 670 (MH+);

5-[1-[4-(2,4-Bis-trifluoromethyl-benzyloxy)-3-methoxy-phenyl]-methylidene]-2-[4-(2-thiophen-2-yl-ethyl)-piperazin-1-yl]-thiazol-4-one; MS (ES): 656 (MH+);

3-({5-[1-[4-(2,4-Bis-trifluoromethyl-benzyloxy)-3-methoxy-phenyl]-methylidene]-4-oxo-4,5-dihydro-thiazol-2-yl}-thiophen-2-ylmethyl-amino)-propionitrile; MS (ES): 626 (MH+);

5-[1-[4-(2,4-Bis-trifluoromethyl-benzyloxy)-3-methoxy-phenyl]-methylidene]-2-(4-naphthalen-1-ylmethyl-piperazin-1-yl)-thiazol-4-one; MS (ES): 686 (MH+);

5-[1-[4-(2,4-Bis-trifluoromethyl-benzyloxy)-3-methoxy-phenyl]-methylidene]-2-[4-(5-trifluoromethyl-pyridin-2-yl)-piperazin-1-yl]-thiazol-4-one; MS (ES): 691 (MH+);

5-[1-[4-(2,4-Bis-trifluoromethyl-benzyloxy)-3-methoxy-phenyl]-methylidene]-2-[4-(2-pyridin-2-yl-ethyl)-piperazin-1-yl]-thiazol-4-one; MS (ES): 651 (MH+);

5-[1-[4-(2,4-Bis-trifluoromethyl-benzyloxy)-3-methoxy-phenyl]-methylidene]-2-(4-pyridin-3-ylmethyl-piperazin-1-yl)-thiazol-4-one; MS (ES): 637 (MH+);

5-[1-[4-(2,4-Bis-trifluoromethyl-benzyloxy)-3-methoxy-phenyl]-methylidene]-2-thiomorpholin-4-yl-thiazol-4-one; MS (ES): 563 (MH+);

5-[1-[4-(2,4-Bis-trifluoromethyl-benzyloxy)-3-methoxy-phenyl]-methylidene]-2-[4-(4-phenyl-butyl)-piperazin-1-yl]-thiazol-4-one; MS (ES): 678 (MH+);

5-[1-[4-(2,4-Bis-trifluoromethyl-benzyloxy)-3-methoxy-phenyl]-methylidene]-2-[4-(4,6-dimethoxy-pyrimidin-2-yl-methyl]-thiazol-4-one; MS (ES): 698 (MH+);

5-[1-[4-(2,4-Bis-trifluoromethyl-benzyloxy)-3-methoxy-phenyl]-methylidene]-2-[4-(tetrahydro-furan-2-carbonyl)-piperazin-1-yl]-thiazol-4-one; MS (ES): 644 (MH+);

5-[1-[4-(2,4-Bis-trifluoromethyl-benzyloxy)-3-methoxy-phenyl]-methylidene]-2-(4-pyridin-4-ylmethyl-piperazin-1-yl)-thiazol-4-one; MS (ES): 637 (MH+);

5-[1-[4-(2,4-Bis-trifluoromethylbenzyloxy)-3-methoxy-phenyl]-methylidene]-2-[4-(3-phenyl-propyl)-piperazin-1-yl]-thiazol-4-one; MS (ES): 664 (MH+);

2-(4-Benzo[1,3]dioxol-5-ylmethyl-piperazin-1-yl)-5-[1-[4-(2,4-bis-trifluoromethyl-benzyloxy)-3-methoxy-phenyl]-methylidene]-thiazol-4-one; MS (ES): 680 (MH+);

1-{5-[1-[4-(2,4-Bis-trifluoromethyl-benzyloxy)-3-methoxy-phenyl]-methylidene]-4-oxo-4,5-dihydro-thiazol-2-yl}-piperidine-4-carboxylic acid ethyl ester; MS (ES): 617 (MH+);

5-[1-[4-(2,4-Bis-trifluoromethyl-benzyloxy)-3-methoxy-phenyl]-methylidene]-2-(4-ethyl-piperazin-1-yl)-thiazol-4-one; MS (ES): 574 (MH+);

1-{5-[1-[4-(2,4-Bis-trifluoromethyl-benzyloxy)-3-methoxy-phenyl]-methylidene]-4-oxo-4,5-dihydro-thiazol-2-yl}-piperidine-3-carboxylic acid ethyl ester; MS (ES): 617 (MH+);

5-[1-[4-(2,4-Bis-trifluoromethyl-benzyloxy)-3-methoxy-phenyl]-methylidene]-2-(1,4-dioxa-8-aza-spiro[4.5]dec-8-yl)-thiazol-4-one; MS (ES): 603 (MH+);

5-[1-[4-(2,4-Bis-trifluoromethyl-benzyloxy)-3-methoxy-phenyl]-methylidene]-2-[4-(2-methoxy-ethyl)-piperazin-1-yl]-thiazol-4-one; MS (ES): 604 (MH+);

5-[1-[4-(2,4-Bis-trifluoromethyl-benzyloxy)-3-methoxy-phenyl]-methylidene]-2-(4-octyl-piperazin-1-yl)-thiazol-4-one; MS (ES): 658 (MH+);

(1-{5-[1-[4-(2,4-Bis-trifluoromethyl-benzyloxy)-3-methoxy-phenyl]-methylidene]-4-oxo-4,5-dihydro-thiazol-2-yl}-piperidin-4-yl)-carbamic acid tert-butyl ester; MS (ES): 660 (MH+);

(S)-1-{5-[1-[4-(2,4-Bis-trifluoromethyl-benzyloxy)-3-methoxy-phenyl]-methylidene]-4-oxo-4,5-dihydro-thiazol-2-yl}-pyrrolidine-2-carboxylic acid methyl ester; MS (ES): 589 (MH+);

5-[1-[4-(2,4-Bis-trifluoromethyl-benzyloxy)-3-methoxy-phenyl]-methylidene]-2-[4-(2-oxo-2-pyrrolidin-1-yl-ethyl)-piperazin-1-yl]-thiazol-4-one; MS (ES): 657 (MH+);

5-[1-[4-(2,4-Bis-trifluoromethyl-benzyloxy)-3-methoxy-phenyl]-methylidene]-2-[4-(2-morpholin-4-yl-2-oxo-ethyl)-piperazin-1-yl]-thiazol-4-one; MS (ES): 673 (MH+);

5-[1-[4-(2,4-Bis-trifluoromethyl-benzyloxy)-3-methoxy-phenyl]-methylidene]-2-(4-phenyl-piperidin-1-yl)-thiazol-4-one; MS (ES): 621 (MH+);

2-(4-Allyl-piperazin-1-yl)-5-[1-[4-(2,4-bis-trifluoromethyl-benzyloxy)-3-methoxy-phenyl]-methylidene]-thiazol-4-one; MS (ES): 586 (MH+);

2-(4-{5-[1-[4-(2,4-Bis-trifluoromethyl-benzyloxy)-3-methoxy-phenyl]-methylidene]-4-oxo-4,5-dihydro-thiazol-2-yl}-piperazin-1-yl)-benzonitrile; MS (ES). 647 (MH+);

5-[1-[4-(2,4-Bis-trifluoromethyl-benzyloxy)-3-methoxy-phenyl]-methylidene]-2-[4-(3-methoxy-propyl)-piperazin-1-yl]-thiazol-4-one; MS (ES): 618 (MH+);

5-[1-[4-(2,4-Bis-trifluoromethyl-benzyloxy)-3-methoxy-phenyl]-methylidene]-2-(4-p-tolyl-piperazin-1-yl)-thiazol-4-one; MS (ES): 636 (MH+);

5-[1-[4-(2,4-Bis-trifluoromethyl-benzyloxy)-3-methoxy-phenyl]-methylidene]-2-[4-(2-fluoro-phenyl)-piperazin-1-yl]-thiazol-4-one; MS (ES): 640 (MH+);

5-[1-[4-(2,4-Bis-trifluoromethyl-benzyloxy)-3-methoxy-phenyl]-methylidene]-2-[4-(4-trifluoromethyl-phenyl)-piperazin-1-yl]-thiazol-4-one; MS (ES): 690 (MH+);

5-[1-[4-(2,4-Bis-trifluoromethyl-benzyloxy)-3-methoxy-phenyl]-methylidene]-2-[4-(3,4-dichloro-phenyl)-piperazin-1-yl]-thiazol-4-one; MS (ES): 690 (MH+);

1-{5-[1-[4-(2,4-Bis-trifluoromethyl-benzyloxy)-3-methoxy-phenyl]-methylidene]-4-oxo-4,5-dihydro-thiazol-2-yl}-piperidine-2-carboxylic acid ethyl ester; MS (ES): 617 (MH+);

5-[1-[4-(2,4-Bis-trifluoromethyl-benzyloxy)-3-methoxy-phenyl]-methylidene]-2-(4-pyridin-4-yl-piperazin-1-yl)-thiazol-4-one; MS (ES): 623 (MH+);

(1-{5-[1-[4-(2,4-Bis-trifluoromethyl-benzyloxy)-3-methoxy-phenyl]-methylidene]-4-oxo 4,5-dihydro-thiazol-2-yl}-pyrrolidin-3-yl)-carbamic acid tert-butyl ester; MS (ES): 646 (MH+);

2-(4-Benzyl-piperidin-1-yl)-5-[1-[4-(2,4-bis-trifluoromethyl-benzyloxy)-3-methoxy-phenyl]-meth-(Z)-ylidene]-thiazol-4-one; MS (ES): 635 (MH+);

5-[1-[4-(2,4-Bis-trifluoromethyl-benzyloxy)-3-methoxy-phenyl]-methylidene]-2-[4-(2-dipropylamino-ethyl)-piperazin-1-yl]-thiazol-4-one; MS (ES): 673 (MH+);

5-[1-[4-(2,4-Bis-trifluoromethyl-benzyloxy)-3-methoxy-phenyl]-methylidene]-2-[4-(1-phenyl-ethyl)-piperazin-1-yl]-thiazol-4-one; MS (ES): 650 (MH+);

5-[1-[4-(2,4-Bis-trifluoromethyl-benzyloxy)-3-methoxy-phenyl]-methylidene]-2-(4-isopropyl-piperazin-1-yl)-thiazol-4-one; MS (ES): 588 (MH+);

5-[1-[4-(2,4-Bis-trifluoromethyl-benzyloxy)-3-methoxy-phenyl]-methylidene]-2-(4-pyrimidin-2-yl-piperazin-1-yl)-thiazol-4-one; MS (ES): 624 (MH+);

5-[1-[4-(2,4-Bis-trifluoromethyl-benzyloxy)-3-methoxy-phenyl]-methylidene]-2-(4-cyclopentyl-piperazin-1-yl)-thiazol-4-one; MS (ES): 614 (MH+);

5-[1-[4-(2,4-Bis-trifluoromethyl-benzyloxy)-3-methoxyphenyl]-methylidene]-2-(4-hexyl-piperazin-1-yl)-thiazol-4-one; MS (ES): 630 (MH+);

5-[1-[4-(2,4-Bis-trifluoromethyl-benzyloxy)-3-methoxy-phenyl]-methylidene]-2-(4-cycloheptyl-piperazin-1-yl)-thiazol-4-one; MS (ES): 642 (MH+);

5-[1-[4-(2,4-Bis-trifluoromethyl-benzyloxy)-3-methoxy-phenyl]-methylidene]-2-(4-butyl-piperazin-1-yl)-thiazol-4-one; MS (ES): 602 (MH+);

5-[1-[4-(2,4-Bis-trifluoromethyl-benzyloxy)-3-methoxy-phenyl]-methylidene]—2-[4-(2-morpholin-4-yl-ethyl)-piperazin-1-yl]-thiazol-4-one; MS (ES): 659 (MH+);

5-[1-[4-(2,4-Bis-trifluoromethyl-benzyloxy)-3-methoxy-phenyl]-methylidene]-2-(4-cyclo hexyl-piperazin-1-yl)-thiazol-4-one; MS (ES): 628 (MH+);

5-[1-[4-(2,4-Bis-trifluoromethyl-benzyloxy)-3-methoxy-phenyl]-methylidene]-2-(2,3,5,6-tetrahydro-[1,2']bipyrazinyl-4-yl)-thiazol-4-one; MS (ES): 624 (MH+);

5-[1-[4-(2,4-Bis-trifluoromethyl-benzyloxy)-3-methoxy-phenyl]-methylidene]-2-[4-(2,3-dichloro-phenyl)-piperazin-1-yl]-thiazol-4-one; MS (ES): 690 (MH+);

5-[1-[4-(2,4-Bis-trifluoromethyl-benzyloxy)-3-methoxy-phenyl]-methylidene]-2-[4-(2-trifluoromethyl-phenyl)-piperazin-1-yl]-thiazol-4-one; MS (ES): 690 (MH+);

5-[1-[4-(2,4-Bis-trifluoromethyl-benzyloxy)-3-methoxy-phenyl]-methylidene]-2-[4-(2-pyrrolidin-1-yl-ethyl)-piperazin-1-yl]-thiazol-4-one; MS (ES): 643 (MH+);

5-[1-[4-(2,4-Bis-trifluoromethyl-benzyloxy)-3-methoxy-phenyl]-methylidene]-2-[4-(tetrahydro-furan-2-ylmethyl)-piperazin-1-yl]-thiazol-4-one; MS (ES): 630 (MH+);

5-[1-[4-(2,4-Bis-trifluoromethyl-benzyloxy)-3-methoxy-phenyl]-methylidene]-2-(4-pentyl-piperazin-1-yl)-thiazol-4-one; MS (ES): 616 (MH+);

5-[1-[4-(2,4-Bis-trifluoromethyl-benzyloxy)-3-methoxy-phenyl]-methylidene]-2-[4-(2-diethylamino-ethyl)-piperazin-1-yl]-thiazol-4-one; MS (ES): 645 (MH+);

3-(4-{5-[1-[4-(2,4-Bis-trifluoromethyl-benzyloxy)-3-methoxy-phenyl]-methylidene]-4-oxo-4,5-dihydro-thiazol-2-yl}-piperazin-1-yl)-propionitrile; MS (ES): 599 (MH+);

5-[1-[4-(2,4-Bis-trifluoromethyl-benzyloxy)-3-methoxy-phenyl]-methylidene]-2-(4-heptyl-piperazin-1-yl)-thiazol-4-one; MS (ES): 644 (MH+);

5-[1-[4-(2,4-Bis-trifluoromethyl-benzyloxy)-3-methoxy-phenyl]-methylidene]-2-[4-(4-methoxy-butyl)-piperazin-1-yl]-thiazol-4-one; MS (ES): 632 (MH+);

5-[1-[4-(2,4-Bis-trifluoromethyl-benzyloxy)-3-methoxy-phenyl]-methylidene]-2-[4-(6-methyl-pyridin-2-yl)-piperazin-1-yl]-thiazol-4-one; MS (ES): 637 (MH+);

5-[1-[4-(2,4-Bis-trifluoromethyl-benzyloxy)-3-methoxy-phenyl]-methylidene]-2-[4-(2-dimethylamino-ethyl)-piperazin-1-yl]-thiazol-4-one; MS (ES): 617 (MH+);

5-[1-[4-(2,4-Bis-trifluoromethyl-benzyloxy)-3-methoxy-phenyl]-methylidene]-2-[4-(1-methyl-piperidin-4-ylmethyl)-piperazin-1-yl]-thiazol-4-one; MS (ES): 657 (MH+);

5-[1-[4-(2,4-Bis-trifluoromethyl-benzyloxy)-3-methoxy-phenyl]-methylidene]-2-[4-(2-diallylamino-ethyl)-piperazin-1-yl]-thiazol-4-one; MS (ES): 669 (MH+);

5-[1-[4-(2,4-Bis-trifluoromethyl-benzyloxy)-3-methoxy-phenyl]-methylidene]-2-(4-m-tolyl-piperazin-1-yl)-thiazol-4-one; MS (ES): 636 (MH+);

5-[1-[4-(2,4-Bis-trifluoromethyl-benzyloxy)-3-methoxy-phenyl]-methylidene]-2-[4-(1-methyl-piperidin-3-ylmethyl)-piperazin-1-yl]-thiazol-4-one; MS (ES): 657 (MH+);

5-[1-[4-(2,4-Bis-trifluoromethyl-benzyloxy)-3-methoxy-phenyl]-methylidene]-2-[4-(1-ethyl-propyl)-piperazin-1-yl]-thiazol-4-one; MS (ES): 616 (MH+);

5-[1-[4-(2,4-Bis-trifluoromethyl-benzyloxy)-3-methoxy-phenyl]-methylidene]-2-[4-(3-chloro-phenyl)-piperazin-1-yl]-thiazol-4-one; MS (ES): 656 (MH+);

5-[1-[4-(2,4-Bis-trifluoromethyl-benzyloxy)-3-methoxy-phenyl]-methylidene]-2-(4-sec-butyl-piperazin-1-yl)-thiazol-4-one; MS (ES): 602 (MH+);

5-[1-[4-(2,4-Bis-trifluoromethyl-benzyloxy)-3-methoxy-phenyl]-methylidene]-2-[4-(3-dimethylamino-propyl)-piperazin-1-yl]-thiazol-4-one; MS (ES): 631 (MH+);

5-[1-[4-(2,4-Bis-trifluoromethyl-benzyloxy)-3-methoxy-phenyl]-methylidene]-2-[4-(3-methoxy-phenyl)-piperazin-1-yl]-thiazol-4-one; MS (ES): 652 (MH+);

5-[1-[4-(2,4-Bis-trifluoromethyl-benzyloxy)-3-methoxy-phenyl]-methylidene]-2-[4-(1-methyl-butyl)-piperazin-1-yl]-thiazol-4-one; MS (ES): 616 (MH+);

5-[1-[4-(2,4-Bis-trifluoromethyl-benzyloxy)-3-methoxy-phenyl]-methylidene]-2-(4-[1,3]dioxolan-2-ylmethyl-piperazin-1-yl)-thiazol-4-one; MS (ES): 632 (MH+);

2-(4-{5-[1-[4-(2,4-Bis-trifluoromethyl-benzyloxy)-3-methoxy-phenyl]-methylidene]-4-oxo-4,5-dihydro-thiazol-2-yl}-piperazin-1-yl)-N-methyl-N-phenyl-acetamide; MS (ES): 693 (MH+);

5-[1-[4-(2,4-Bis-trifluoromethyl-benzyloxy)-3-methoxy-phenyl]-methylidene]-2-(4-o-tolyl-piperazin-1-yl)-thiazol-4-one; MS (ES): 636 (MH+);

5-[1-[4-(2,4-Bis-trifluoromethyl-benzyloxy)-3-methoxy-phenyl]-methylidene]-2-[4-(2-hydroxy-phenyl)-piperazin-1-yl]-thiazol-4-one; MS (ES): 638 (MH+);

5-[1-[4-(2,4-Bis-trifluoromethyl-benzyloxy)-3-methoxy-phenyl]-methylidene]-2-[4-(5-thiophen-2-yl-1H-pyrazol-3-yl)-piperidin-1-yl]-thiazol-4-one; MS (ES): 693 (MH+);

2-(4-{5-[1-[4-(2,4-Bis-trifluoromethyl-benzyloxy)-3-methoxy-phenyl]-methylidene]-4-oxo-4,5-dihydro-thiazol-2-yl}piperazin-1-yl)-nicotinonitrile; MS (ES): 648 (MH+);

5-[1-[4-(2,4-Bis-trifluoromethyl-benzyloxy)-3-methoxy-phenyl]-methylidene]-2-[4-(2,4-dimethyl-phenyl)-piperazin-1-yl]-thiazol-4-one; MS (ES): 650 (MH+);

4-{5-[1-[4-(2,4-Bis-trifluoromethyl-benzyloxy)-3-methoxy-phenyl]-methylidene]-4-oxo-4,5-dihydro-thiazol-2-yl}-piperazine-1-carboxylic acid tert-butyl ester; MS (ES): 646 (MH+);

1-{5-[1-[4-(2,4-Bis-trifluoromethyl-benzyloxy)-3-methoxy-phenyl]-methylidene]-4-oxo-4,5-dihydro-thiazol-2-yl}-piperidine-4-carboxylic acid methyl ester; MS (ES): 603 (MH+);

2-(4-Benzyl-piperazin-1-yl)-5-[1-[4-(2,4-bis-trifluoromethyl-benzyloxy)-3-methoxy-phenyl]-methylidene]-thiazol-4-one; MS (ES): 636 (MH+);

5-[1-[4-(2,4-Bis-trifluoromethyl-benzyloxy)-3-methoxy-phenyl]-methylidene]-2-(4-hydroxy-piperidin-1-yl)-thiazol-4-one; MS (ES): 561 (MH+);

5-[1-[4-(2,4-Bis-trifluoromethyl-benzyloxy)-3-methoxy-phenyl]-methylidene]-2-(2,6-dimethyl-morpholin-4-yl)-thiazol-4-one; MS (ES): 575 (MH+);

5-[1-[4-(2,4-Bis-trifluoromethyl-benzyloxy)-3-methoxy-phenyl]-methylidene]-2-((S)-2-hydroxymethyl-pyrrolidin-1-yl)-thiazol-4-one; MS (ES): 561 (MH+);

5-[1-[4-(2,4-Bis-trifluoromethyl-benzyloxy)-3-methoxy-phenyl]-methylidene]-2-(octahydro-quinolin-1-yl)-thiazol-4-one; MS (ES): 599 (MH+);

5-[1-[4-(2,4-Bis-trifluoromethyl-benzyloxy)-3-methoxy-phenyl]-methylidene]-2 (octahydro-isoquinolin-2-yl)-thiazol-4-one; MS (ES): 599 (MH+);

5-[1-[4-(2,4-Bis-trifluoromethyl-benzyloxy)-3-methoxy-phenyl]-methylidene]-2-[4-(2-piperidin-1-yl-ethyl)-piperazin-1-yl]-thiazol-4-one; MS (ES): 657 (MH+);

5-[1-[4-(2,4-Bis-trifluoromethyl-benzyloxy)-3-methoxy-phenyl]-methylidene]-2-[4-(1-methyl-piperidin-4-yl)-piperazin-1-yl]-thiazol-4-one; MS (ES): 643 (MH+);

5-[1-[4-(2,4-Bis-trifluoromethyl-benzyloxy)-3-methoxy-phenyl]-methylidene]-2-[4-(4-chloro-phenyl)-piperazin-1-yl]-thiazol-4-one; MS (ES): 656 (MH+);

5-[1-[4-(2,4-Bis-trifluoromethyl-benzyloxy)-3-methoxy-phenyl]-methylidene]-2-[4-(4-methoxy-phenyl)-piperazin-1-yl]-thiazol-4-one; MS (ES): 652 (MH+);

5-[1-[4-(2,4-Bis-trifluoromethyl-benzyloxy)-3-methoxy-phenyl]-methylidene]-2-[4-(3,5-dichloro-phenyl)-piperazin-1-yl]-thiazol-4-one; MS (ES): 690 (MH+);

2-[1,4']Bipiperidinyl-1'-yl-5-[1-[4-(2,4-bis-trifluoromethyl-benzyloxy)-3-methoxy-phenyl]-methylidene]-thiazol-4-one; MS (ES): 628 (MH+);

4-{5-[1-[4-(2,4-Bis-trifluoromethyl-benzyloxy)-3-methoxy-phenyl]-methylidene]-4-oxo-4,5-dihydro-thiazol-2-yl}-piperazine-1-carboxylic acid ethyl ester; MS (ES): 618 (MH+);

5-[1-[4-(2,4-Bis-trifluoromethyl-benzyloxy)-3-methoxy-phenyl]-methylidene]-2-(4-pyridin-2-ylmethyl-piperazin-1-yl)-thiazol-4-one; MS (ES): 637 (MH+);

5-[1-[4-(2,4-Bis-trifluoromethyl-benzyloxy)-3-methoxy-phenyl]-methylidene]-2-[4-(3-trifluoromethyl-phenyl)-piperazin-1-yl]-thiazol-4-one; MS (ES): 690 (MH+);

5-[1-[4-(2,4-Bis-trifluoromethyl-benzyloxy)-3-methoxy-phenyl]-methylidene]-2-(4-phenethyl-piperazin-1-yl)-thiazol-4-one; MS (ES): 650 (MH+);

5-[1-[4-(2,4-Bis-trifluoromethyl-benzyloxy)-3-methoxy-phenyl]-methylidene]-2-(2-methyl-piperidin-1-yl)-thiazol-4-cane; MS (ES): 559 (MH+);

5-[1-[4-(2,4-Bis-trifluoromethyl-benzyloxy)-3-methoxy-phenyl]-methylidene]-2-(4-methyl-piperidin-1-yl)-thiazol-4-one; MS (ES): 559 (MH+);

5-[1-[4-(2,4-Bis-trifluoromethyl-benzyloxy)-3-methoxy-phenyl]-methylidene]-2-pyrrolidin-1-yl-thiazol-4-one; MS (ES): 531 (MH+);

5-[1-[4-(2,4-Bis-trifluoromethyl-benzyloxy)-3-methoxy-phenyl]-methylidene]-2-morpholin-4-yl-thiazol-4-one; MS (ES): 547 (MH+);

5-[1-[4-(2,4-Bis-trifluoromethyl-benzyloxy)-3-methoxy-phenyl]-methylidene]-2-[cyclopropyl-(1,3,5-trimethyl-1H-pyrazol-4-ylmethyl)-amino]-thiazol-4-one; MS (ES): 639 (MH+);

5-[1-[4-(2,4-Bis-trifluoromethyl-benzyloxy)-3-methoxy-phenyl]-methylidene]-2-[4-(1H-indol-3-yl)-piperidin-1-yl]-thiazol-4-one; MS (ES): 660 (MH+);

5-[1-[4-(2,4-Bis-trifluoromethyl-benzyloxy)-3-methoxy-phenyl]-methylidene]-2-[methyl-(5-methyl-1H-indol-3-yl-methyl)-amino]-thiazol-4-one; MS (ES): 634 (MH+);

5-[1-[4-(2,4-Bis-trifluoromethyl-benzyloxy)-3-methoxy-phenyl]-methylidene]-2-[methyl-(3-phenyl-[1,2,4]oxadiazol-5-ylmethyl)-amino]-thiazol-4-one; MS (ES): 649 (MH+);

5-[1-[4-(2,4-Bis-trifluoromethyl-benzyloxy)-3-methoxy-phenyl]-methylidene]-2-[methyl-(4-methyl-thiazol-2-ylmethyl)-amino]-thiazol-4-one; MS (ES): 602 (MH+);

5-[1-[4-(2,4-Bis-trifluoromethyl-benzyloxy)-3-methoxy-phenyl]-methylidene]-2-[methyl-(5-phenyl-[1,3,4]oxadiazol-2-ylmethyl)-amino]-thiazol-4-one; MS (ES): 649 (MH+);

2-(Benzo[b]thiophen-2-ylmethyl-methyl-amino)-5-[1-[4-(2,4-bis-trifluoromethyl-benzyloxy)-3-methoxy-phenyl]-meth-(Z)-ylidene]-thiazol-4-one; MS (ES): 637 (MH+);

5-[1-[4-(2,4-Bis-trifluoromethyl-benzyloxy)-3-methoxy-phenyl]-methylidene]-2-[methyl-(5-propyl-1H-pyrazol-3-ylmethyl)-amino]-thiazol-4-one; MS (ES): 613 (MH+);

5-[1-[4-(2,4-Bis-trifluoromethyl-benzyloxy)-3-methoxy-phenyl]-methylidene]-2-(4-pyrimidin-2-yl-[1,4]diazepan-1-yl)-thiazol-4-one; MS (ES): 638 (MH+);

5-[1-[4-(2,4-Bis-trifluoromethyl-benzyloxy)-3-methoxy-phenyl]-methylidene]-2-(4-thiophen-3-ylmethyl-piperazin-1-yl)-thiazol-4-one; MS (ES): 642 (MH+);

5-[1-[4-(2,4-Bis-trifluoromethyl-benzyloxy)-3-methoxy-phenyl]-methylidene]-2-[2-(1H-indol-2-yl)-pyrrolidin-1-yl]-thiazol-4-one; MS (ES): 646 (MH+);

5-[1-[4-(2,4-Bis-trifluoromethyl-benzyloxy)-3-methoxy-phenyl]-methylidene]-2-(2-pyridin-2-yl-azepan-1-yl)-thiazol-4-one; MS (ES): 636 (MH+);

5-[1-[4-(2,4-Bis-trifluoromethyl-benzyloxy)-3-methoxy-phenyl]-methylidene]-2-[4-(3-methyl-pyridin-2-ylmethyl)-piperazin-1-yl]-thiazol-4-one; MS (ES): 651 (MH+);

5-[1-[4-(2,4-Bis-trifluoromethyl-benzyloxy)-3-methoxy-phenyl]-methylidene]-2-[methyl-(3-methyl-pyridin-2-ylmethyl)-amino]-thiazol-4-one; MS (ES): 596 (MH+);

2-(4-Benzooxazol-2-yl-[1,4]diazepan-1-yl)-5-[1-[4-(2,4-bis-trifluoromethyl-benzyloxy)-3-methoxy-phenyl]-methylidene]-thiazol-4-one; MS (ES): 677 (MH+);

5-[1-[4-(2,4-Bis-trifluoromethyl-benzyloxy)-3-methoxy-phenyl]-methylidene]-2-(methyl-thiophen-2-ylmethyl-amino)-thiazol-4-one; MS (ES): 587 (MH+);

5-[1-[4-(2,4-Bis-trifluoromethyl-benzyloxy)-3-methoxy-phenyl]-methylidene]-2-[3-(5-methyl-1H-benzoimidazol-2-yl)-piperidin-1-yl]-thiazol-4-one; MS (ES): 675 (MH+);

1-{5-[1-[4-(2,4-Bis-trifluoromethyl-benzyloxy)-3-methoxy-phenyl]-methylidene]-4-oxo-4,5-dihydro-thiazol-2-yl}-piperidine-4-carboxylic acid; MS (ES): 589 (MH+);

5-[1-[4-(2,4-Bis-trifluoromethyl-benzyloxy)-3-methoxy-phenyl]-methylidene]-2-[4-(hydroxy-pyridin-2-yl-methyl)-piperidin-1-yl]-thiazol-4-one; MS (ES): 652 (MH+);

5-[1-[4-(2,4-Bis-trifluoromethyl-benzyloxy)-3-methoxy-phenyl]-methylidene]-2-[3-(5-fluoro-1H-benzoimidazol-2-yl)-piperidin-1-yl]-thiazol-4-one; MS (ES): 679 (MH+);

5-[1-[4-(2,4-Bis-trifluoromethyl-benzyloxy)-3-methoxy-phenyl]-methylidene]-2-(methyl-quinolin-6-ylmethyl-amino)-thiazol-4-one; MS (ES): 632 (MH+);

2-(4-Benzooxazol-2-yl-piperidin-1-yl)-5-[1-[4-(2,4-bis-trifluoromethyl-benzyloxy)-3-methoxy-phenyl]-methylidene]-thiazol-4-one; MS (ES): 662 (MH+); and 5-[1-[4-(2,4-Bis-trifluoromethyl-benzyloxy)-3-methoxy-phenyl]-methylidene]-2-[2-(6-methyl-1H-benzoimidazol-2-yl)-pyrrolidin-1-yl]-thiazol-4-one. MS (ES): 661 (MH+).

Example 49

Fluorescence Polarization (FP) Assay

The human ERRα ligand binding domain consisting of amino acids 188-423 (see GenBank sequence XM048286) was cloned into the pET15b expression vector (Novagen, Inc., Madison, Wis.) with the 6-Histidine tag in frame with the N-terminus of the ligand binding domain.

6-His-tagged ERRα ligand-binding domain fusion protein was expressed in *E. Coli* and purified on Ni-NTA resin (Qiagen Inc., Valencia, Calif.) following standard protocols. The purity of the protein was checked using SDS PAGE and Coomassie blue staining. The protein was judged to be approximately 90% pure by this method.

1×FP Buffer (20 mM $KH_2PO_4$ Ph 7.3, 150 mM NaCl, 2 mM CHAPS, 2 mM EDTA, 10 mM DTT) containing 10 nM of 5,6-Carboxyfluorescein-ILRKLLQE (SynPep Corp., Dublin, Calif.), 5.5 µM His-ERRα protein and 50 µM or 10 µM of test compound were added to each well of a 384-well black assay plate.

Plates were incubated at room temperature in the dark for at least 1 hour. FP (mP) was measured on an LJL Analyst (LJL Biosystems, Inc., Sunnyvale, Calif.) (excitation wavelength: 485 nm; emission wavelength: 530 nm).

The mP value of His-ERRα plus the peptide was used as a high control and set as 100% activity. The mP value of the peptide only was set as the low control. Antagonist cut-off was set as >25% max inhibition (75% activity compared to high control).

Example 50

GAL4-ERRα Co-Transfection Assay

Compound activity was also determined in a cell based assay using a GAL4-ERRα chimera to identify active compounds.

CMX-GAL4-ERRα was constructed by cloning nucleotides encoding amino acids 174-423 of ERRα (see GenBank sequence XM048286) into the vector pCMX-GAL4 (Perlmann et al., 1993, Genes & Development 7:1411-1422) comprising nucleotides encoding for amino acids 1-147 of the GAL4 DNA binding domain.

The TK-MH100×4-Luc ($GAL4_{UAS}$-TK-Luciferase) reporter constructs were constructed by insertion of four copies of the Gal4 UAS (Kang et al. 1993, J. Biol. Chem. 268: 9629-9635) into the Hind III site of TK-Luc. The parental plasmid TK-Luc was prepared by insertion of the Herpes simplex virus thymidine kinase gene promoter (−105 to +51) obtained from the plasmid pBLCAT2 by digestion with HindIII and XhoI (described in Luckow et al., 1987, Nuc. Acid. Res. 15:5490) into the plasmid MTV-LUC described by Hollenberg and Evans, 1988, Cell 55:899-906) after removal of MTV-LTR promoter sequence from MTV-LUC via digestion with HindIII and XhoI. Correct cloning was confirmed by restriction digestion and or sequencing.

Assays were performed using CV-1 (African Green Monkey Kidney Cells) (ATCC) cells at 70 percent confluency in T175 flasks grown with media containing 10% charcoal/

Dextran-treated fetal bovine serum. Cells were transiently transfected with a DNA mixture containing 12 μg of CMX-GAL4-ERRα (comprising the ligand binding domain), 6 Sag of TK-MH100×4-Luc, and 2 μg of CMX-βGal using the transfection reagent FuGENE6 (Roche Molecular Biochemicals, Indianapolis, Ind.) following recommended protocols and instructions provided by the manufacturer. Following incubation with transfection reagents for 5 hours at 37° C., cells were washed, removed from the flasks with 1× Trypsin-EDTA solution (Sigma-Aldrich, Inc. St. Louis, Mo., and then resuspended in media containing 5% charcoal/Dextran-treated fetal bovine serum to give a final concentration of $1.1 \times 10^5$ cells/ml.

Assay plates were prepared by dispensing approximately 5 μl of each compound into a well of a 384 well plate to achieve a final compound concentration of approximately 10 μM after addition of cells. Cells were added to assay plates (45 μl) via the use of a Multiprop dispenser (MTX Labs, Inc., Vienna, Va.). The assay plates containing both compounds and screening cells were incubated for approximately 20 hours at 37° C. and 5% $CO_2$ in a tissue culture incubator.

After incubation of the transfected cells with compounds, Lysis buffer (1% Triton X-100, 10% Glycerol, 5 mM DTT, 1 mM EGTA, 25 mM Tricine) and Luciferin assay buffer (0.73 mM ATP, 22.3 mM Tricine, 0.11 mM EDTA, 33.3 mM DTT, 0.2M $MgSO_4$, 11 mM Luciferin, 6.1 mM Coenzyme A, 0.01 mM HEPES) were prepared. Media was removed from the plates and lysis buffer and luciferin assay buffer mixed in a 1:1 ratio and then 30 μl was added to each well (384-well plate). Plates were read on the Northstar (Northstar Technologies, Inc., Acton, Mass.) and data was analyzed using ActivityBase (ID Business Solutions, Ltd., Guildford, Surrey, UK). Luciferase values were normalized with β-galactosidase values using the pCMX-βGal expression plasmid, to normalize for transfection efficiency as described previously (Willy et al., 1995, Gene & Development, 9:1033-1045).

No reporter-driven luciferase activity was observed without ERR transfection, indicating the ERR-dependency of the compounds.

The following table provides in vitro ERRα activity data of representative compounds described in the Examples. Average $IC_{50}$ values for inverse agonist activity in the GAL4-ERRα assay are provided as follows: V: less than 0.5 μM; W: 0.5 μM-1 μM; X: 1 μM to 2 μM and Y: 2 μM to 5 μM. Average percent inhibition with respect to ERRα activity relative to a control (3-[4-(2,4-Bis-trifluoromethyl-benzyloxy)-3-methoxy-phenyl]-2-cyano-N-(5-trifluoromethyl-[1,3,4]thiadiazol-2-yl)-acrylamide) is provided as follows. A: 100-120% of control activity, B: 80-100% of control activity and C: 60-80% of control activity.

TABLE

| Example | ERRα IC50 | % control |
|---|---|---|
| 5-[1-[4-(2,4-Bis-trifluoromethyl-benzyloxy)-3-methoxy-phenyl]-methylidene]-2-(4-methyl-piperazin-1-yl)-thiazol-4-one | V | A |
| 5-[1-[4-(2,4-Bis-trifluoromethyl-benzyloxy)-3-methoxy-phenyl]-methylidene]-2-piperazin-1-yl-thiazol-4-one | V | A |
| 5-[1-[4-(2,4-Bis-trifluoromethyl-benzyloxy)-3-methoxy-phenyl]-methylidene]-2-(4-methanesulfonyl-piperazin-1-yl)-thiazol-4-one | V | A |
| 5-[1-[4-(2,4-Bis-trifluoromethyl-benzyloxy)-3-methoxy-phenyl]-methylidene]-2-(2-pyridin-2-yl-pyrrolidin-1-yl)-thiazol-4-one | V | A |

TABLE-continued

| Example | ERRα IC50 | % control |
|---|---|---|
| 5-[1-[4-(2,4-Bis-trifluoromethyl-benzyloxy)-3-methoxy-phenyl]-methylidene]-2-thiomorpholin-4-yl-thiazol-4-one | W | A |
| 5-[1-[4-(2,4-Bis-trifluoromethyl-benzyloxy)-3-methoxy-phenyl]-methylidene]-2-[4-(1-methyl-piperidin-4-ylmethyl)-piperazin-1-yl]-thiazol-4-one; | W | B |
| 5-[1-[4-(2,4-Bis-trifluoromethyl-benzyloxy)-3-methoxy-phenyl]-methylidene]-2-morpholin-4-yl-thiazol-4-one | W | B |
| 5-[1-[4-(2,4-Bis-trifluoromethyl-benzyloxy)-3-methoxy-phenyl]-methylidene]-2-(2,6-dimethyl-morpholin-4-yl)-thiazol-4-one | X | A |
| 5-[1-[4-(2,4-Bis-trifluoromethyl-benzyloxy)-3-methoxy-phenyl]-methylidene]-2-[3-(5-methyl-1H-benzoimidazol-2-yl)-piperidin-1-yl]-thiazol-4-one | X | B |
| 5-[1-[4-(2,4-Bis-trifluoromethyl-benzyloxy)-3-methoxy-phenyl]-methylidene]-2-[4-(4-chloro-benzyl)-piperazin-1-yl]-thiazol-4-one | Y | C |
| 5-[1-[4-(2,4-Bis-trifluoromethyl-benzyloxy)-3-methoxy-phenyl]-methylidene]-2-(4-pentyl-piperazin-1-yl)-thiazol-4-one | Y | B |

The skilled practitioner will understand that many modifications and variations may be made in the techniques and structures described and illustrated herein without departing from the spirit and scope of the present invention. Accordingly, the techniques and structures described and illustrated herein should be understood to be illustrative only and not limiting upon the scope of the present invention. The scope of the present invention is defined by the claims, which includes known equivalents and unforeseeable equivalents at the time of the filing of this application.

What is claimed is:

1. A compound of formula (I):

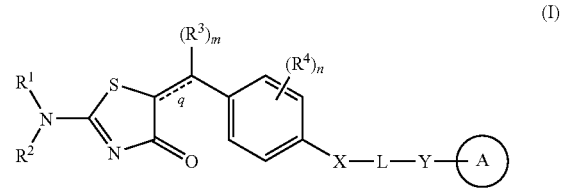

wherein:
bond q is a single bond or a double bond;
$R^1$ and $R^2$ are each independently optionally substituted alkyl, optionally substituted alkenyl, optionally substituted alkynyl, optionally substituted cycloalkyl, optionally substituted cycloalkylalkyl, optionally substituted heterocyclyl, optionally substituted heterocyclylalkyl, optionally substituted aryl, optionally substituted aralkyl, optionally substituted heteroaryl, optionally substituted heteroaralkyl, —$OR^{10}$ or —$C(O)R^{10}$; and $R^2$ can additionally be hydrogen; or
$R^1$ and $R^2$, together with the nitrogen atom to which they are attached, form an optionally substituted heterocyclic or heteroaryl ring, wherein said optionally substituted heterocyclic or heteroaryl ring may be substituted with one to twelve substituents each independently selected from the group consisting of $R^5$ and $R^6$;
$R^3$ is hydrogen, halo or optionally substituted alkyl;
each $R^4$ is independently halo, cyano, nitro, optionally substituted alkyl, optionally substituted alkenyl, optionally substituted alkynyl, optionally substituted cycloalkyl, optionally substituted cycloalkylalkyl, optionally substituted heterocyclyl, optionally substituted heterocyclylalkyl, optionally substituted aryl, optionally substituted aralkyl, optionally substituted heteroaryl, optionally substituted heteroaralkyl, —$R^9$—$N(R^{21})(R^{22})$, $R^9$—$OR^{20}$, —$R^9$—$SR^{20}$, —$R^9$—$C(O)R^{20}$, —$R^9$—$C(O)OR^{20}$, —$R^9$—$C(O)N(R^{21})(R^{22})$, —$R^9$—$OC(O)R^{20}$, —$R^9$—$N(R^8)C(O)R^{20}$, —$R^9$—$OC(O)OR^{20}$, —$R^9$—$OC(O)N(R^{21})(R^{22})$, —$R^9$—$N(R^8)C(O)OR^{20}$, —$R^9$—$N(R^8)C(O)N(R^{21})(R^{22})$, —$R^9$—$N(R^8)S(O)_2R^{23}$, —$R^9$—$S(O)_tR^{23}$ (where t is an integer from 1 to 2) or —$R^9$—$S(O)_2N(R^{21})(R^{22})$;

each $R^5$ and $R^6$ are independently selected from the group consisting of halo, cyano, nitro, optionally substituted alkyl, optionally substituted alkenyl, optionally substituted alkynyl, optionally substituted cycloalkyl, optionally substituted cycloalkylalkyl, optionally substituted heterocyclyl, optionally substituted heterocyclylalkyl, optionally substituted aryl, optionally substituted aralkyl, optionally substituted heteroaryl or optionally substituted heteroaralkyl and —$R^9$—$OR^{10}$, —$R^9$—$N(R^{11})(R^{12})$, —$R^9$—$SR^{10}$, —$R^9$—$C(J)R^{10}$, —$R^9$—$C(J)OR^{10}$, —$R^9$—$C(J)N(R^{11})(R^{12})$, —$R^9$—$N(R^8)C(O)OR^{10}$, —$R^9$—$OC(O)N(R^{11})(R^{12})$, —$R^9$—$N(R^8)C(J)N(R^{11})(R^{12})$ and —$R^9$—$S(O)_tR^{13}$ (where t is an integer from 1 to 2); or $R^5$ and $R^6$, together with the carbon to which they are attached, form oxo, thioxo, cycloalkyl, heterocyclyl, ethylene dioxy or propylene dioxy;

m is an integer from 1 to 2;

n is an integer from 0 to 4;

X is —O—, —$NR^8$—, —$S(O)_u$— (where u is an integer from 0 to 2) or a direct bond;

L is an optionally substituted branched or linear alkylene chain having 1 to 6 carbons, an optionally substituted cycloalkyl having 3 to 6 carbons, an optionally substituted branched or linear alkenylene chain having 2 to 6 carbons and 1 to 2 double bonds or an optionally substituted branched or linear alkynylene chain having 2 to 6 carbons and 1 to 2 triple bonds;

Y is —O—, —$NR^8$—, —$S(O)_u$— (where u is an integer from 0 to 2) or a direct bond;

A is 2,4-bis-trifluorophenyl;

each $R^8$ is independently hydrogen or optionally substituted alkyl each $R^9$ is independently a direct bond or optionally substituted alkylene;

each $R^{10}$ and $R^{20}$ are independently selected from the group consisting of hydrogen, optionally substituted alkyl, optionally substituted alkenyl, optionally substituted alkynyl, optionally substituted cycloalkyl, optionally substituted cycloalkylalkyl, optionally substituted heterocyclyl, optionally substituted heterocyclylalkyl, optionally substituted aryl, optionally substituted aralkyl, optionally substituted heteroaryl and optionally substituted heteroaralkyl;

$R^{11}$ and $R^{12}$ are each independently selected from the group consisting of hydrogen, optionally substituted alkyl, optionally substituted alkenyl, optionally substituted alkynyl, optionally substituted cycloalkyl, optionally substituted cycloalkylalkyl, optionally substituted heterocyclyl, optionally substituted heterocyclylalkyl, optionally substituted aryl, optionally substituted aralkyl, optionally substituted heteroaryl and optionally substituted heteroaralkyl, or $R^{11}$ and $R^{12}$, together with the nitrogen atom to which they are attached, form an optionally substituted heterocyclyl or optionally substituted heteroaryl, $R^{21}$ and $R^{22}$ are each independently selected from the group consisting of hydrogen, optionally substituted alkyl, optionally substituted alkenyl, optionally substituted alkynyl, optionally substituted cycloalkyl, optionally substituted cycloalkylalkyl, optionally substituted heterocyclyl, optionally substituted heterocyclylalkyl, optionally substituted aryl, optionally substituted aralkyl, optionally substituted heteroaryl and optionally substituted heteroaralkyl, or $R^{21}$ and $R^{22}$, together with the nitrogen atom to which they are attached, form an optionally substituted heterocyclyl or an optionally substituted heteroaryl, $R^{13}$, $R^{23}$ are each independently selected from the group consisting of optionally substituted alkyl, optionally substituted alkenyl, optionally substituted alkynyl, optionally substituted cycloalkyl, optionally substituted cycloalkylalkyl, optionally substituted heterocyclyl, optionally substituted heterocyclylalkyl, optionally substituted aryl, optionally substituted aralkyl, optionally substituted heteroaryl and optionally substituted heteroaralkyl; and J is O,S or $NR^{14}$;

wherein $R^{14}$ is selected from the group consisting of hydrogen, optionally substituted alkyl, or optionally substituted cycloalkyl;

as a single stereoisomer, a mixture of stereoisomers, or as a racemic mixture of stereoisomers; as any tautomeric form; or as a pharmaceutically acceptable salt thereof.

2. The compound of claim 1 wherein bond q is a double bond.

3. The compound of claim 1 wherein:

X is —O—;

L is methylene, ethylene or propylene; and

Y is —O— or a direct bond.

4. The compound of claim 1 wherein Y is —O—.

5. The compound of claim 1 having the formula (II):

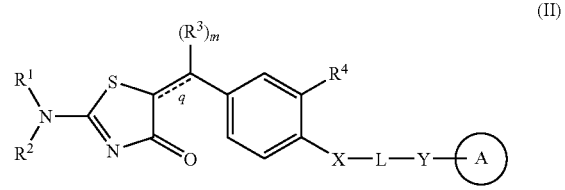

where $R^4$ is halo, haloalkyl, cyano, —$OR^{20}$, —$N(R^{21})(R^{22})$ or —$SR^{20}$; and $R^{20}$, $R^{21}$ and $R^{22}$ are as described in claim 1.

6. The compound of claim 1 wherein:

$R^4$ is —$OR^{20}$; and;

$R^{20}$ is selected from the group consisting of optionally substituted alkyl, optionally substituted alkenyl or optionally substituted alkynyl.

7. The compound of claim 1 having the formula (II):

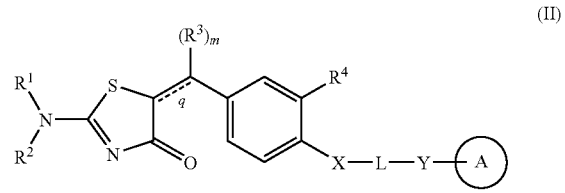

wherein:

R$^4$ is halo, cyano, optionally substituted alkyl, —R$^9$—C(O)R$^{20}$, —R$^9$—C(O)OR$^{20}$, —R$^9$—C(O)N(R$^{21}$)(R$^{22}$), —R$^9$—OC(O)R$^{20}$, —R$^9$—N(R$^8$)C(O)R$^{20}$, —R$^9$—OC(O)OR$^{20}$, —R$^9$—OC(O)N(R$^{21}$)(R$^{22}$), —R$^9$—N(R$^8$)C(O)OR$^{20}$, —R$^9$—N(R$^8$)C(O)N(R$^{21}$)(R$^{22}$), —R$^9$—N(R$^8$)S(O)$_2$R$^{23}$, —R$^9$—S(O)$_t$R$^{23}$ (where t is an integer from 1 to 2) or —R$^9$—S(O)$_2$N(R$^{21}$)(R$^{22}$);

where R$^8$, R$^9$, R$^{20}$, R$^{21}$, R$^{22}$ and R$^{23}$ are as described in claim 1.

8. The compound of claim 1 wherein:

R$^1$ is optionally substituted alkyl, optionally substituted alkenyl, optionally substituted alkynyl, optionally substituted cycloalkyl, optionally substituted cycloalkylalkyl, optionally substituted heterocyclyl, optionally substituted heterocyclylalkyl, optionally substituted aryl, optionally substituted aralkyl, optionally substituted heteroaryl, optionally substituted heteroaralkyl, —OR$^{10}$ or —C(O)R$^{10}$; and R$^2$ is hydrogen, optionally substituted alkyl, optionally substituted alkenyl, optionally substituted alkynyl, optionally substituted cycloalkyl, optionally substituted cycloalkylalkyl, optionally substituted heterocyclyl, optionally substituted heterocyclylalkyl, optionally substituted aryl, optionally substituted aralkyl, optionally substituted heteroaryl, optionally substituted heteroaralkyl, —OR$^{10}$ or —C(O)R$^{10}$;

where R$^{10}$ is as described in claim 1.

9. The compound of claim 1 wherein:

R$^1$ is optionally substituted alkyl, optionally substituted alkenyl or optionally substituted alkynyl and R$^2$ is hydrogen.

10. The compound of claim 9 wherein L is methylene.

11. The compound of claim 9 wherein said compound is selected from the group consisting of:

5-[1-[4-(2,4-bis-trifluoromethyl-benzyloxy)-3-methoxy-phenyl]-methylidene]-2-(3-dimethylamino-propylamino)-thiazol-4-one;

5-[1-[4-(2,4-bis-trifluoromethyl-benzyloxy)-3-methoxy-phenyl]-methylidene]-2-(2-methoxy-ethylamino)-thiazol-4-one;

5-[1-[4-(2,4-bis-trifluoromethyl-benzyloxy)-3-methoxy-phenyl]-methylidene]-2-ethylamino-thiazol-4-one;

5-[1-[4-(2,4-bis-trifluoromethyl-benzyloxy)-3-methoxy-phenyl]-methylidene]-2-methylamino-thiazol-4-one;

5-[1-[4-(2,4-bis-trifluoromethyl-benzyloxy)-3-methoxy-phenyl]-methylidene]-2-propylamino-thiazol-4-one; and 5-[1-[4-(2,4-bis-trifluoromethyl-benzyloxy)-3-methoxy-phenyl]-methylidene]-2-dimethylamino-thiazol-4-one;

as a single stereoisomer, a mixture of stereoisomers, or as a racemic mixture of stereoisomers; as any tautomeric form; or as a pharmaceutically acceptable salt thereof.

12. The compound of claim 8 wherein:

R$^1$ is optionally substituted cycloalkyl, optionally substituted cycloalkylalkyl, optionally substituted heterocyclyl, optionally substituted heterocyclylalkyl, optionally substituted aryl, optionally substituted aralkyl, optionally substituted heteroaryl, optionally substituted heteroaralkyl, —OR$^{10}$, or —C(O)R$^{10}$;

R$^2$ is hydrogen; and

L is methylene;

where R$^{10}$ is as described in claim 1.

13. The compound of claim 12 wherein said compound is selected from the group consisting of:

5-[1-[4-(2,4-bis-trifluoromethyl-benzyloxy)-3-methoxy-phenyl]-methylidene]-2-(4-methoxy-benzylamino)-thiazol-4-one;

5-[1-[4-(2,4-bis-trifluoromethyl-benzyloxy)-3-methoxy-phenyl]-methylidene]-2-(2,4-difluoro-benzylamino)-thiazol-4-one 5-[1-[4-(2,4-bis-trifluoromethyl-benzyloxy)-3-methoxy-phenyl]-methylidene]-2-phenethylamino-thiazol-4-one;

5-[1-[4-(2,4-bis-trifluoromethyl-benzyloxy)-3-methoxy-phenyl]-methylidene]-2-cyclohexylamino-thiazol-4-one;

5-[1-[4-(2,4-bis-trifluoromethyl-benzyloxy)-3-methoxy-phenyl]-methylidene]-2-(2-morpholin-4-yl-ethylamino)-thiazol-4-one;

5-[1-[4-(2,4-bis-trifluoromethyl-benzyloxy)-3-methoxy-phenyl]-methylidene]-2-hydroxyamino-thiazol-4-one;

3-{5-[1-[4-(2,4-bis-trifluoromethyl-benzyloxy)-3-methoxy-phenyl]-methylidene]-4-oxo-4,5-dihydro-thiazol-2-ylamino}-benzoic acid ethyl ester; and 5-[1-[4-(2,4-bis-trifluoromethyl-benzyloxy)-3-methoxy-phenyl]-methylidene]-2-phenylamino-thiazol-4-one;

as a single stereoisomer, a mixture of stereoisomers, or as a racemic mixture of stereoisomers; as any tautomeric form; or as a pharmaceutically acceptable salt thereof.

14. The compound of claim 8 wherein:

R$^1$ is optionally substituted alkyl, optionally substituted alkenyl, optionally substituted alkynyl, optionally substituted cycloalkyl, optionally substituted cycloalkylalkyl, optionally substituted heterocyclyl, optionally substituted heterocyclylalkyl, optionally substituted aryl, optionally substituted aralkyl, optionally substituted heteroaryl, optionally substituted heteroaralkyl, —OR$^{10}$, or —C(O)R$^{10}$; and R$^2$ is optionally substituted alkyl, optionally substituted alkenyl, optionally substituted alkynyl or optionally substituted cycloalkyl;

where R$^{10}$ is as described in claim 1.

15. The compound of claim 14 wherein L is methylene.

16. The compound of claim 14 wherein said compound is selected from the group consisting of:

5-[1-[4-(2,4-bis-trifluoromethyl-benzyloxy)-3-methoxy-phenyl]-methylidene]-2-(ethyl-phenyl-amino)-thiazol-4-one;

3-({5-[1-[4-(2,4-bis-trifluoromethyl-benzyloxy)-3-methoxy-phenyl]-methylidene]-4-oxo-4,5-dihydro-thiazol-2-yl}-thiophen-2-ylmethyl-amino)-propionitrile;

5-[1-[4-(2,4-Bis-trifluoromethyl-benzyloxy)-3-methoxy-phenyl]-methylidene]-2-[cyclopropyl-(1,3,5-trimethyl-1H-pyrazol-4-ylmethyl)-amino]-thiazol-4-one;

5-[1-[4-(2,4-bis-trifluoromethyl-benzyloxy)-3-methoxy-phenyl]-methylidene]-2-[methyl-(5-methyl-1H-indol-3-ylmethyl)-amino]-thiazol-4-one;

5-[1-[4-(2,4-bis-trifluoromethyl-benzyloxy)-3-methoxy-phenyl]-methylidene]-2-[methyl-(3-phenyl-[1,2,4]oxadiazol-5-ylmethyl)-amino]-thiazol-4-one;

5-[1-[4-(2,4-bis-trifluoromethyl-benzyloxy)-3-methoxy-phenyl]-methylidene]-2-[methyl-(4-methyl-thiazol-2-ylmethyl)-amino]-thiazol-4-one;

5-[1-[4-(2,4-bis-trifluoromethyl-benzyloxy)-3-methoxy-phenyl]-methylidene]-2-[methyl-(5-phenyl-[1,3,4]oxadiazol-2-ylmethyl)-amino]-thiazol-4-one;

2-(benzo[b]thiophen-2-ylmethyl-methyl-amino)-5-[1-[4-(2,4-bis-trifluoromethyl-benzyloxy)-3-methoxy-phenyl]-methylidene]-thiazol-4-one;

5-[1-[4-(2,4-bis-trifluoromethyl-benzyloxy)-3-methoxy-phenyl]-methylidene]-2-[methyl-(5-propyl-1H-pyrazol-3-ylmethyl)-amino]-thiazol-4-one;

5-[1-[4-(2,4-bis-trifluoromethyl-benzyloxy)-3-methoxy-phenyl]-methylidene]-2-[methyl-(3-methyl-pyridin-2-ylmethyl)-amino]-thiazol-4-one;

5-[1-[4-(2,4-bis-trifluoromethyl-benzyloxy)-3-methoxy-phenyl]-methylidene]-2-(methyl-thiophen-2-ylmethyl-amino)-thiazol-4-one; and 5-[1-[4-(2,4-bis-trifluoromethyl-benzyloxy)-3-methoxy-phenyl]-methylidene]-2-(methyl-quinolin-6-ylmethyl-amino)-thiazol-4-one;

as a single stereoisomer, a mixture of stereoisomers, or as a racemic mixture of stereoisomers; as any tautomeric form; or as a pharmaceutically acceptable salt thereof.

17. The compound of claim 3 wherein:
n is 0; and
A is -2,4-bis-trifluorophenyl.

18. The compound of claim 17 wherein said compound is 5-[1-[4-(2,4-Bis-trifluoromethyl-benzyloxy)-phenyl]-methylidene]-2-(4-methyl-piperazin-1-yl)-thiazol-4-one;

as a single stereoisomer, a mixture of stereoisomers, or as a racemic mixture of stereoisomer; as any tautomeric form; or as a pharmaceutically acceptable salt thereof.

19. The compound of claim 3 wherein:
$R^1$ and $R^2$, together with the nitrogen atom to which they are attached, form an optionally substituted heterocyclic ring, wherein said optionally substituted heterocyclic ring may be substituted with one to twelve substituents each independently selected from the group consisting of optionally substituted alkyl, optionally substituted alkenyl, optionally substituted alkynyl, optionally substituted cycloalkyl, optionally substituted cycloalkylalkyl, optionally substituted heterocyclyl, optionally substituted heterocyclylalkyl, optionally substituted aryl, optionally substituted aralkyl, optionally substituted heteroaryl, optionally substituted heteroaralkyl, $-R^9-OR^{10}$, $-R^9-N(R^{11})(R^{12})$, $-R^9-C(J)R^{10}$, $-R^9-C(J)OR^{10}$, $-R^9-C(J)N(R^{11})(R^{12})$, $-R^9-N(R^8)C(O)OR^{10}$, $-R^9-OC(O)N(R^{11})(R^{12})$, $-R^9-N(R^8)C(J)N(R^{11})(R^{12})$ and $-R^9-S(O)_tR^{13}$ (where t is an integer from 1 to 2).

20. The compound of claim 19 wherein A -2,4-bis-trifluorophenyl.

21. The compound of claim 20 wherein L is methylene.

22. The compound of claim 19 wherein said optionally substituted heterocyclyl formed by $R^1$ and $R^2$, is unsubstituted pyrrolidine; or substituted pyrrolidine having the structure:

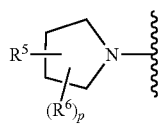

wherein p is an integer from 0 to seven, and $R^5$ and $R^6$ are as described in claim 1.

23. The compound of claim 22 wherein:
p is 0 to 7;
$R^5$ is selected from the group consisting of optionally substituted alkyl, optionally substituted aryl, optionally substituted heteroaryl, $-R^9-C(J)R^{10}$, $-R^9-C(J)OR^{10}$, $-R^9-C(J)N(R^{11})(R^{12})$ and $-R^9-N(R^8)C(O)OR^{10}$, and $R^6$ is each independently selected from the group consisting of halo, cyano, nitro, $-R^9-OR^{10}$, $-R^9-N(R^{11})(R^{12})$ and $-R^9-SR^{10}$;
wherein $R^9$, $R^{10}$, $R^{11}$ and $R^{12}$ are as described in claim 1.

24. The compound of claim 23 wherein p is 0.

25. The compound of claim 22 selected from the group consisting of:
5-[1-[4-(2,4-bis-trifluoromethyl-benzyloxy)-3-methoxy-phenyl]-methylidene]-2-(2-pyridin-2-yl-pyrrolidin-1-yl)-thiazol-4-one;

5-[1-[4-(2,4-bis-trifluoromethyl-benzyloxy)-3-methoxy-phenyl]-methylidene]-2-(3-pyridin-2-yl-pyrrolidin-1-yl)-thiazol-4-one;

5-[1-[4-(2,4-bis-trifluoromethyl-benzyloxy)-3-methoxy-phenyl]-methylidene]-2-(2-pyridin-3-yl-pyrrolidin-1-yl)-thiazol-4-one;

(S)-1-{5-[1-[4-(2,4-bis-trifluoromethyl-benzyloxy)-3-methoxy-phenyl]-methylidene]-4-oxo-4,5-dihydro-thiazol-2-yl}-pyrrolidine-2-carboxylic acid methyl ester;

5-[1-[4-(2,4-bis-trifluoromethyl-benzyloxy)-3-methoxy-phenyl]-methylidene]-2-(3-pyridin-3-yl-pyrrolidin-1-yl)-thiazol-4-one;

5-[1-[4-(2,4-bis-trifluoromethyl-benzyloxy)-3-methoxy-phenyl]-methylidene]-2-[2-(5-fluoro-1H-benzoimidazol-2-yl)-pyrrolidin-1-yl]-thiazol-4-one;

(1-{5-[1-[4-(2,4-bis-trifluoromethyl-benzyloxy)-3-methoxy-phenyl]-methylidene]-4-oxo-4,5-dihydro-thiazol-2-yl}-pyrrolidin-3-yl)-carbamic acid tert-butyl ester;

5-[1-[4-(2,4-bis-trifluoromethyl-benzyloxy)-3-methoxy-phenyl]-methylidene]-2-((S)-2-hydroxymethyl-pyrrolidin-1-yl)-thiazol-4-one;

5-[1-[4-(2,4-bis-trifluoromethyl-benzyloxy)-3-methoxy-phenyl]-methylidene]-2-pyrrolidin-1-yl-thiazol-4-one;

5-[1-[4-(2,4-bis-trifluoromethyl-benzyloxy)-3-methoxy-phenyl]-methylidene]-2-[2-(1H-indol-2-yl)-pyrrolidin-1-yl]-thiazol-4-one; and 5-[1-[4-(2,4-bis-trifluoromethyl-benzyloxy)-3-methoxy-phenyl]-methylidene]-2-[2-(6-methyl-1H-benzoimidazol-2-yl)-pyrrolidin-1-yl]-thiazol-4-one;

as a single stereoisomer, a mixture of stereoisomers, or as a racemic mixture of stereoisomers; as any tautomeric form; or as a pharmaceutically acceptable salt thereof.

26. The compound of claim 19 wherein said optionally substituted heterocyclyl formed by $R^1$ and $R^2$ is unsubstituted piperidine; or substituted piperidine having the structure:

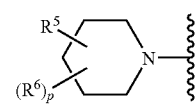

wherein p is an integer from 0 to nine and $R^5$ and $R^6$ are as described in claim 1.

27. The compound of claim 26 wherein:
p is an integer from 0 to nine;
$R^5$ is selected from the group consisting of optionally substituted alkyl, optionally substituted aralkyl, optionally substituted heterocyclyl, optionally substituted heteroaryl, optionally substituted heteroaralkyl, $-R^9-OR^{10}$, $-R^9-N(R^{11})(R^{12})$, $-R^9-SR^{10}$, $-R^9-C(J)R^{10}$, $R^9-C(J)OR^{10}$, $-R^9-C(J)N(R^{11})(R^{12})$ and $-R^9-N(R^8)C(O)OR^{10}$;

$R^6$ is each independently selected from the group consisting of halo, cyano, nitro, $-R^9-OR^{10}$, $-R^9-N(R^{11})(R^{12})$ and $-R^9-SR^{10}$; or R⁵ and R⁶, together on the same carbon, form oxo, thioxo, cycloalkyl, ethylene dioxy or propylene dioxy;
wherein R⁹, R¹⁰, R¹¹ and R¹² are as described in claim 1.

28. The compound of claim 27 wherein p is 0.

29. The compound of claim 26 is selected from the group consisting of:
  5-[1-[4-(2,4-bis-trifluoromethyl-benzyloxy)-3-methoxy-phenyl]-methylidene]-2-piperidin-1-yl-thiazol-4-one;
  5-[1-[4-(2,4-bis-trifluoromethyl-benzyloxy)-3-methoxy-phenyl]-methylidene]-2-[3-(pyridine-3-carbonyl)-piperidin-1-yl]-thiazol-4-one;
  5-[1-[4-(2,4-bis-trifluoromethyl-benzyloxy)-3-methoxy-phenyl]-methylidene]-2-[4-(hydroxy-pyridin-3-yl-methyl)-piperidin-1-yl]-thiazol-4-one;
  1-{5-[1-[4-(2,4-bis-trifluoromethyl-benzyloxy)-3-methoxy-phenyl]-methylidene]-4-oxo-4,5-dihydro-thiazol-2-yl}-piperidine-4-carboxylic acid ethyl ester;
  1-{5-[1-[4-(2,4-bis-trifluoromethyl-benzyloxy)-3-methoxy-phenyl]-methylidene]-4-oxo-4,5-dihydro-thiazol-2-yl}-piperidine-3-carboxylic acid ethyl ester;
  5-[1-[4-(2,4-bis-trifluoromethyl-benzyloxy)-3-methoxy-phenyl]-methylidene]-2-(1,4-dioxa-8-aza-spiro[4.5]dec-8-yl)-thiazol-4-one;
  (1-{5-[1-[4-(2,4-bis-trifluoromethyl-benzyloxy)-3-methoxy-phenyl]-methylidene]-4-oxo-4,5-dihydro-thiazol-2-yl}-piperidin-4-yl)-carbamic acid tert-butyl ester;
  5-[1-[4-(2,4-bis-trifluoromethyl-benzyloxy)-3-methoxy-phenyl]-methylidene]-2-(4-phenyl-piperidin-1-yl)-thiazol-4-one;
  1-{5-[1-[4-(2,4-bis-trifluoromethyl-benzyloxy)-3-methoxy-phenyl]-methylidene]-4-oxo-4,5-dihydro-thiazol-2-yl}-piperidine-2-carboxylic acid ethyl ester;
  2-(4-benzyl-piperidin-1-yl)-5-[1-[4-(2,4-bis-trifluoromethyl-benzyloxy)-3-methoxy-phenyl]-methylidene]-thiazol-4-one;
  5-[1-[4-(2,4-bis-trifluoromethyl-benzyloxy)-3-methoxy-phenyl]-methylidene]-2-[4-(5-thiophen-2-yl-1H-pyrazol-3-yl)-piperidin-1-yl]-thiazol-4-one;
  1-{5-[1-[4-(2,4-bis-trifluoromethyl-benzyloxy)-3-methoxy-phenyl]-methylidene]-4-oxo-4,5-dihydro-thiazol-2-yl}-piperidine-4-carboxylic acid methyl ester;
  5-[1-[4-(2,4-bis-trifluoromethyl-benzyloxy)-3-methoxy-phenyl]-methylidene]-2-(4-hydroxy-piperidin-1-yl)-thiazol-4-one;
  2-[1,4']bipiperidinyl-1'-yl-5-[1-[4-(2,4-bis-trifluoromethyl-benzyloxy)-3-methoxy-phenyl]-methylidene]-thiazol-4-one;
  5-[1-[4-(2,4-bis-trifluoromethyl-benzyloxy)-3-methoxy-phenyl]-methylidene]-2-(2-methyl-piperidin-1-yl)-thiazol-4-one;
  5-[1-[4-(2,4-bis-trifluoromethyl-benzyloxy)-3-methoxy-phenyl]-methylidene]-2-(4-methyl-piperidin-1-yl)-thiazol-4-one;
  5-[1-[4-(2,4-bis-trifluoromethyl-benzyloxy)-3-methoxy-phenyl]-methylidene]-2-[4-(1H-indol-3-yl)-piperidin-1-yl]-thiazol-4-one;
  5-[1-[4-(2,4-bis-trifluoromethyl-benzyloxy)-3-methoxy-phenyl]-methylidene]-2-[3-(5-methyl-1H-benzoimidazol-2-yl)-piperidin-1-yl]-thiazol-4-one;
  1-{5-[1-[4-(2,4-bis-trifluoromethyl-benzyloxy)-3-methoxy-phenyl]-methylidene]-4-oxo-4,5-dihydro-thiazol-2-yl}-piperidine-4-carboxylic acid;
  5-[1-[4-(2,4-bis-trifluoromethyl-benzyloxy)-3-methoxy-phenyl]-methylidene]-2-[4-(hydroxy-pyridin-2-yl-methyl)-piperidin-1-yl]-thiazol-4-one;
  5-[1-[4-(2,4-bis-trifluoromethyl-benzyloxy)-3-methoxy-phenyl]-methylidene]-2-[3-(5-fluoro-1H-benzoimidazol-2-yl)-piperidin-1-yl]-thiazol-4-one; and
  2-(4-benzooxazol-2-yl-piperidin-1-yl)-5-[1-[4-(2,4-bis-trifluoromethyl-benzyloxy)-3-methoxy-phenyl]-methylidene]-thiazol-4-one;
  as a single stereoisomer, a mixture of stereoisomers, or as a racemic mixture of stereoisomers; as any tautomeric form; or as a pharmaceutically acceptable salt thereof.

30. The compound of claim 19 wherein said optionally substituted heterocyclyl formed by R¹ and R², is unsubstituted piperazine; or substituted piperazine having the structure:

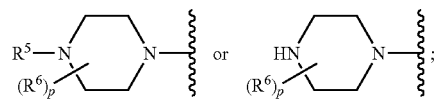

wherein p is an integer from 0 to 8 and R⁵ and R⁶ are as described in claim 1.

31. The compound of claim 30 wherein:
R⁵ is selected from the group consisting of optionally substituted alkyl, optionally substituted alkenyl, optionally substituted alkynyl, optionally substituted cycloalkyl, optionally substituted cycloalkylalkyl, optionally substituted heterocyclyl, optionally substituted heterocyclylalkyl, optionally substituted aryl, optionally substituted aralkyl, optionally substituted heteroaryl, optionally substituted heteroaralkyl, —R⁹—C(J)R¹⁰, —R⁹—C(J)OR¹⁰, —R⁹—C(J)N(R¹¹)(R¹²) and —R⁹—S(O)ᵣR¹³;
R⁶ is each independently selected from the group consisting of halo, cyano, nitro, —R⁹—OR¹⁰, —R⁹—N(R¹¹)(R¹²) and —R⁹—SR¹⁰;
wherein R⁹, R¹⁰, R¹¹, R¹² and R¹² are as described in claim 1.

32. The compound of claim 31 wherein p is 0.

33. The compound of claim 30 wherein said optionally substituted heterocyclyl is unsubstituted piperazine.

34. The compound of claim 33 wherein said compound is
  5-[1-[4-(2,4-bis-trifluoromethyl-benzyloxy)-3-methoxy-phenyl]-methylidene]-2-piperazin-1-yl-thiazol-4-one; or
  5-[1-[4-(2,4-bis-trifluoromethyl-benzyloxy)-3-methoxy-phenyl]-methylidene]-2-(2-methyl-piperazin-1-yl)-thiazol-4-one;
  as a single stereoisomer, a mixture of stereoisomers, or as a racemic mixture of stereoisomers; as any tautomeric form; or as a pharmaceutically acceptable salt thereof.

35. The compound of claim 30 wherein R⁵ is selected from the group consisting of optionally substituted alkyl, optionally substituted alkenyl and optionally substituted alkynyl.

36. The compound of claim 35 wherein said compound is selected from the group consisting of:
  5-[1-[4-(2,4-bis-trifluoromethyl-benzyloxy)-3-methoxy-phenyl]-methylidene]-2-(4-methyl-piperazin-1-yl)-thiazol-4-one;
  5-[1-[4-(2,4-bis-trifluoromethyl-benzyloxy)-3-methoxy-phenyl]-ethylidene]-2-(4-methyl-piperazin-1-yl)-thiazol-4-one;
  5-[1-[4-(2,4-bis-trifluoromethyl-benzyloxy)-3-methoxy-phenyl]-methylidene]-2-(4-ethyl-piperazin-1-yl)-thiazol-4-one;

5-[1-[4-(2,4-bis-trifluoromethyl-benzyloxy)-3-methoxy-phenyl]-methylidene]-2-[4-(2-methoxy-ethyl)-piperazin-1-yl]-thiazol-4-one;

5-[1-[4-(2,4-bis-trifluoromethyl-benzyloxy)-3-methoxy-phenyl]-methylidene]-2-(4-octyl-piperazin-1-yl)-thiazol-4-one;

2-(4-allyl-piperazin-1-yl)-5-[1-[4-(2,4-bis-trifluoromethyl-benzyloxy)-3-methoxy-phenyl]-methylidene]-thiazol-4-one;

5-[1-[4-(2,4-bis-trifluoromethyl-benzyloxy)-3-methoxy-phenyl]-methylidene]-2-[4-(3-methoxy-propyl)-piperazin-1-yl]-thiazol-4-one;

5-[1-[4-(2,4-bis-trifluoromethyl-benzyloxy)-3-methoxy-phenyl]-methylidene]-2-[4-(2-dipropylamino-ethyl)-piperazin-1-yl]-thiazol-4-one;

5-[1-[4-(2,4-bis-trifluoromethyl-benzyloxy)-3-methoxy-phenyl]-methylidene]-2-(4-isopropyl-piperazin-1-yl)-thiazol-4-one;

5-[1-[4-(2,4-bis-trifluoromethyl-benzyloxy)-3-methoxy-phenyl]-methylidene]-2-(4-hexyl-piperazin-1-yl)-thiazol-4-one;

5-[1-[4-(2,4-bis-trifluoromethyl-benzyloxy)-3-methoxy-phenyl]-methylidene]-2-(4-butyl-piperazin-1-yl)-thiazol-4-one;

5-[1-[4-(2,4-bis-trifluoromethyl-benzyloxy)-3-methoxy-phenyl]-methylidene]-2-(4-pentyl-piperazin-1-yl)-thiazol-4-one;

5-[1-[4-(2,4-bis-trifluoromethyl-benzyloxy)-3-methoxy-phenyl]-methylidene]-2-[4-(2-diethylamino-ethyl)-piperazin-1-yl]-thiazol-4-one;

3-(4-{5-[1-[4-(2,4-bis-trifluoromethyl-benzyloxy)-3-methoxy-phenyl]-methylidene]-4-oxo-4,5-dihydro-thiazol-2-yl}-piperazin-1-yl)-propionitrile;

5-[1-[4-(2,4-bis-trifluoromethyl-benzyloxy)-3-methoxy-phenyl]-methylidene]-2-(4-heptyl-piperazin-1-yl)-thiazol-4-one;

5-[1-[4-(2,4-bis-trifluoromethyl-benzyloxy)-3-methoxy-phenyl]-methylidene]-2-[4-(4-methoxy-butyl)-piperazin-1-yl]-thiazol-4-one;

5-[1-[4-(2,4-bis-trifluoromethyl-benzyloxy)-3-methoxy-phenyl]-methylidene]-2-[4-(2-dimethylamino-ethyl)-piperazin-1-yl]-thiazol-4-one;

5-[1-[4-(2,4-bis-trifluoromethyl-benzyloxy)-3-methoxy-phenyl]-methylidene]-2-[4-(2-diallylamino-ethyl)-piperazin-1-yl]-thiazol-4-one;

5-[1-[4-(2,4-bis-trifluoromethyl-benzyloxy)-3-methoxy-phenyl]-methylidene]-2-[4-(1-ethyl-propyl)-piperazin-1-yl]-thiazol-4-one;

5-[1-[4-(2,4-bis-trifluoromethyl-benzyloxy)-3-methoxy-phenyl]-methylidene]-2-(4-sec-butyl-piperazin-1-yl)-thiazol-4-one;

5-[1-[4-(2,4-bis-trifluoromethyl-benzyloxy)-3-methoxy-phenyl]-methylidene]-2-[4-(3-dimethylamino-propyl)-piperazin-1-yl]-thiazol-4-one;

5-[1-[4-(2,4-bis-trifluoromethyl-benzyloxy)-3-methoxy-phenyl]-methylidene]-2-[4-(1-methyl-butyl)-piperazin-1-yl]-thiazol-4-one;

5-[1-[4-(2,4-bis-trifluoromethyl-benzyloxy)-phenyl]-methylidene]-2-piperazin-1-yl)-thiazol-4-one; and 5-[4-(2,4-bis-trifluoromethyl-benzyloxy)-3-methoxy-benzyl]-2-(4-methyl-piperazin-1-yl)-thiazol-4-one;

as a single stereoisomer, a mixture of stereoisomers, or as a racemic mixture of stereoisomers; as any tautomeric form; or as a pharmaceutically acceptable salt thereof.

37. The compound of claim 30 wherein $R^5$ is selected from the group consisting of optionally substituted cycloalkyl, optionally substituted cycloalkylalkyl, optionally substituted heterocyclyl and optionally substituted heterocyclylalkyl.

38. The compound of claim 37 wherein said compound is selected from the group consisting of:

2-(4-benzo[1,3]dioxol-5-ylmethyl-piperazin-1-yl)-5-[1-[4-(2,4-bis-trifluoromethyl-benzyloxy)-3-methoxy-phenyl]-methylidene]-thiazol-4-one;

5-[1-[4-(2,4-bis-trifluoromethyl-benzyloxy)-3-methoxy-phenyl]-methylidene]-2-(4-cyclopentyl-piperazin-1-yl)-thiazol-4-one;

5-[1-[4-(2,4-bis-trifluoromethyl-benzyloxy)-3-methoxy-phenyl]-methylidene]-2-(4-cycloheptyl-piperazin-1-yl)-thiazol-4-one;

5-[1-[4-(2,4-bis-trifluoromethyl-benzyloxy)-3-methoxy-phenyl]-methylidene]-2-[4-(2-morpholin-4-yl-ethyl)-piperazin-1-yl]-thiazol-4-one;

5-[1-[4-(2,4-bis-trifluoromethyl-benzyloxy)-3-methoxy-phenyl]-methylidene]-2-(4-cyclohexyl-piperazin-1-yl)-thiazol-4-one;

5-[1-[4-(2,4-bis-trifluoromethyl-benzyloxy)-3-methoxy-phenyl]-methylidene]-2-[4-(2-pyrrolidin-1-yl-ethyl)-piperazin-1-yl]-thiazol-4-one;

5-[1-[4-(2,4-bis-trifluoromethyl-benzyloxy)-3-methoxy-phenyl]-methylidene]-2-[4-(tetrahydro-furan-2-ylmethyl)-piperazin-1-yl]-thiazol-4-one;

5-[1-[4-(2,4-bis-trifluoromethyl-benzyloxy)-3-methoxy-phenyl]-methylidene]-2-[4-(1-methyl-piperidin-4-ylmethyl)-piperazin-1-yl]-thiazol-4-one;

5-[1-[4-(2,4-bis-trifluoromethyl-benzyloxy)-3-methoxy-phenyl]-methylidene]-2-[4-(1-methyl-piperidin-3-ylmethyl)-piperazin-1-yl]-thiazol-4-one;

5-[1-[4-(2,4-bis-trifluoromethyl-benzyloxy)-3-methoxy-phenyl]-methylidene]-2-(4-[1,3]dioxolan-2-ylmethyl-piperazin-1-yl)-thiazol-4-one;

5-[1-[4-(2,4-bis-trifluoromethyl-benzyloxy)-3-methoxy-phenyl]-methylidene]-2-[4-(2-piperidin-1-yl-ethyl)-piperazin-1-yl]-thiazol-4-one; and 5-[1-[4-(2,4-bis-trifluoromethyl-benzyloxy)-3-methoxy-phenyl]-methylidene]-2-[4-(1-methyl-piperidin-4-yl)-piperazin-1-yl]-thiazol-4-one;

as a single stereoisomer, a mixture of stereoisomers, or as a racemic mixture of stereoisomers; as any tautomeric form; or as a pharmaceutically acceptable salt thereof.

39. The compound of claim 30 wherein $R^5$ is selected from the group consisting of optionally substituted aryl, optionally substituted aralkyl, optionally substituted heteroaryl and optionally substituted heteroaralkyl.

40. The compound of claim 39 wherein said compound is selected from the group consisting of:

5-[1-[4-(2,4-bis-trifluoromethyl-benzyloxy)-3-methoxy-phenyl]-methylidene]-2-(4-pyridin-2-yl-piperazin-1-yl)-thiazol-4-one;

5-[1-[4-(2,4-bis-trifluoromethyl-benzyloxy)-3-methoxy-phenyl]-methylidene]-2-(4-phenyl-piperazin-1-yl)-thiazol-4-one;

5-[1-[4-(2,4-bis-trifluoromethyl-benzyloxy)-3-methoxy-phenyl]-methylidene]-2-[4-(4-hydroxy-phenyl)-piperazin-1-yl]-thiazol-4-one;

5-[1-[4-(2,4-bis-trifluoromethyl-benzyloxy)-3-methoxy-phenyl]-methylidene]-2-[4-(2,4-difluoro-phenyl)-piperazin-1-yl]-thiazol-4-one;

5-[1-[4-(2,4-bis-trifluoromethyl-benzyloxy)-3-methoxy-phenyl]-methylidene]-2-[4-(2-methyl-quinolin-4-yl)-piperazin-1-yl]-thiazol-4-one;

5-[1-[4-(2,4-bis-trifluoromethyl-benzyloxy)-3-methoxy-phenyl]-methylidene]-2-[4-(2-methyl-thiazol-4-ylmethyl)-piperazin-1-yl]-thiazol-4-one;

5-[1-[4-(2,4-bis-trifluoromethyl-benzyloxy)-3-methoxy-phenyl]-methylidene]-2-(4-thiophen-2-ylmethyl-piperazin-1-yl)-thiazol-4-one;
5-[1-[4-(2,4-bis-trifluoromethyl-benzyloxy)-3-methoxy-phenyl]-methylidene]-2-[4-(2,3-dimethyl-phenyl)-piperazin-1-yl]-thiazol-4-one;
5-[1-[4-(2,4-bis-trifluoromethyl-benzyloxy)-3-methoxy-phenyl]-methylidene]-2-[4-(2,5-dimethyl-phenyl)-piperazin-1-yl]-thiazol-4-one;
5-[1-[4-(2,4-bis-trifluoromethyl-benzyloxy)-3-methoxy-phenyl]-methylidene]-2-[4-(4-chloro-benzyl)-piperazin-1-yl]-thiazol-4-one;
5-[1-[4-(2,4-bis-trifluoromethyl-benzyloxy)-3-methoxy-phenyl]-methylidene]-2-[4-(2-thiophen-2-yl-ethyl)-piperazin-1-yl]-thiazol-4-one;
5-[1-[4-(2,4-bis-trifluoromethyl-benzyloxy)-3-methoxy-phenyl]-methylidene]-2-(4-naphthalen-1-ylmethyl-piperazin-1-yl)-thiazol-4-one;
5-[1-[4-(2,4-bis-trifluoromethyl-benzyloxy)-3-methoxy-phenyl]-methylidene]-2-[4-(5-trifluoromethyl-pyridin-2-yl)-piperazin-1-yl]-thiazol-4-one;
5-[1-[4-(2,4-bis-trifluoromethyl-benzyloxy)-3-methoxy-phenyl]-methylidene]-2-[4-(2-pyridin-2-yl-ethyl)-piperazin-1-yl]-thiazol-4-one;
5-[1-[4-(2,4-bis-trifluoromethyl-benzyloxy)-3-methoxy-phenyl]-methylidene]-2-(4-pyridin-3-ylmethyl-piperazin-1-yl)-thiazol-4-one;
5-[1-[4-(2,4-bis-trifluoromethyl-benzyloxy)-3-methoxy-phenyl]-methylidene]-2-[4-(4-phenyl-butyl)-piperazin-1-yl]-thiazol-4-one;
5-[1-[4-(2,4-bis-trifluoromethyl-benzyloxy)-3-methoxy-phenyl]-methylidene]-2-[4-(4,6-dimethoxy-pyrimidin-2-ylmethyl)-piperazin-1-yl]-thiazol-4-one;
5-[1-[4-(2,4-bis-trifluoromethyl-benzyloxy)-3-methoxy-phenyl]-methylidene]-2-(4-pyridin-4-ylmethyl-piperazin-1-yl)-thiazol-4-one;
5-[1-[4-(2,4-bis-trifluoromethyl-benzyloxy)-3-methoxy-phenyl]-methylidene]-2-[4-(3-phenyl-propyl)-piperazin-1-yl]-thiazol-4-one;
2-(4-benzo[1,3]dioxol-5-ylmethyl-piperazin-1-yl)-5-[1-[4-(2,4-bis-trifluoromethyl-benzyloxy)-3-methoxy-phenyl]-methylidene]-thiazol-4-one;
2-(4-{5-[1-[4-(2,4-bis-trifluoromethyl-benzyloxy)-3-methoxy-phenyl]-methylidene]-4-oxo-4,5-dihydro-thiazol-2-yl}-piperazin-1-yl)-benzonitrile;
5-[1-[4-(2,4-bis-trifluoromethyl-benzyloxy)-3-methoxy-phenyl]-methylidene]-2-(4-p-tolyl-piperazin-1-yl)-thiazol-4-one;
5-[1-[4-(2,4-bis-trifluoromethyl-benzyloxy)-3-methoxy-phenyl]-methylidene]-2-[4-(2-fluoro-phenyl)-piperazin-1-yl]-thiazol-4-one;
5-[1-[4-(2,4-bis-trifluoromethyl-benzyloxy)-3-methoxy-phenyl]-methylidene]-2-[4-(4-trifluoromethyl-phenyl)-piperazin-1-yl]-thiazol-4-one;
5-[1-[4-(2,4-bis-trifluoromethyl-benzyloxy)-3-methoxy-phenyl]-methylidene]-2-[4-(3,4-dichloro-phenyl)-piperazin-1-yl]-thiazol-4-one;
5-[1-[4-(2,4-bis-trifluoromethyl-benzyloxy)-3-methoxy-phenyl]-methylidene]-2-(4-pyridin-4-yl-piperazin-1-yl)-thiazol-4-one;
5-[1-[4-(2,4-bis-trifluoromethyl-benzyloxy)-3-methoxy-phenyl]-methylidene]-2-[4-(1-phenyl-ethyl)-piperazin-1-yl]-thiazol-4-one;
5-[1-[4-(2,4-bis-trifluoromethyl-benzyloxy)-3-methoxy-phenyl]-methylidene]-2-(4-pyrimidin-2-yl-piperazin-1-yl)-thiazol-4-one;
5-[1-[4-(2,4-bis-trifluoromethyl-benzyloxy)-3-methoxy-phenyl]-methylidene]-2-(2,3,5,6-tetrahydro-[1,2']bipyrazinyl-4-yl)-thiazol-4-one;
5-[1-[4-(2,4-bis-trifluoromethyl-benzyloxy)-3-methoxy-phenyl]-methylidene]-2-[4-(2,3-dichloro-phenyl)-piperazin-1-yl]-thiazol-4-one;
5-[1-[4-(2,4-bis-trifluoromethyl-benzyloxy)-3-methoxy-phenyl]-methylidene]-2-[4-(2-trifluoromethyl-phenyl)-piperazin-1-yl]-thiazol-4-one;
5-[1-[4-(2,4-bis-trifluoromethyl-benzyloxy)-3-methoxy-phenyl]-methylidene]-2-[4-(6-methyl-pyridin-2-yl)-piperazin-1-yl]-thiazol-4-one;
5-[1-[4-(2,4-bis-trifluoromethyl-benzyloxy)-3-methoxy-phenyl]-methylidene]-2-(4-m-tolyl-piperazin-1-yl)-thiazol-4-one;
5-[1-[4-(2,4-bis-trifluoromethyl-benzyloxy)-3-methoxy-phenyl]-methylidene]-2-[4-(3-chloro-phenyl)-piperazin-1-yl]-thiazol-4-one;
5-[1-[4-(2,4-Bis-trifluoromethyl-benzyloxy)-3-methoxy-phenyl]-methylidene]-2-[4-(3-methoxy-phenyl)-piperazin-1-yl]-thiazol-4-one;
5-[1-[4-(2,4-Bis-trifluoromethyl-benzyloxy)-3-methoxy-phenyl]-methylidene]-2-(4-o-tolyl-piperazin-1-yl)-thiazol-4-one;
5-[1-[4-(2,4-Bis-trifluoromethyl-benzyloxy)-3-methoxy-phenyl]-methylidene]-2-[4-(2-hydroxy-phenyl)-piperazin-1-yl]-thiazol-4-one;
2-(4-{5-[1-[4-(2,4-Bis-trifluoromethyl-benzyloxy)-3-methoxy-phenyl]-methylidene]-4-oxo-4,5-dihydro-thiazol-2-yl}-piperazin-1-yl)-nicotinonitrile;
5-[1-[4-(2,4-Bis-trifluoromethyl-benzyloxy)-3-methoxy-phenyl]-methylidene]-2-[4-(2,4-dimethyl-phenyl)-piperazin-1-yl]-thiazol-4-one;
2-(4-Benzyl-piperazin-1-yl)-5-[1-[4-(2,4-bis-trifluoromethyl-benzyloxy)-3-methoxy-phenyl]-methylidene]-thiazol-4-one;
5-[1-[4-(2,4-Bis-trifluoromethyl-benzyloxy)-3-methoxy-phenyl]-methylidene]-2-[4-(4-chloro-phenyl)-piperazin-1-yl]-thiazol-4-one;
5-[1-[4-(2,4-Bis-trifluoromethyl-benzyloxy)-3-methoxy-phenyl]-methylidene]-2-[4-(4-methoxy-phenyl)-piperazin-1-yl]-thiazol-4-one;
5-[1-[4-(2,4-Bis-trifluoromethyl-benzyloxy)-3-methoxy-phenyl]-methylidene]-2-[4-(3,5-dichloro-phenyl)-piperazin-1-yl]-thiazol-4-one;
5-[1-[4-(2,4-Bis-trifluoromethyl-benzyloxy)-3-methoxy-phenyl]-methylidene]-2-(4-pyridin-2-ylmethyl-piperazin-1-yl)-thiazol-4-one;
5-[1-[4-(2,4-Bis-trifluoromethyl-benzyloxy)-3-methoxy-phenyl]-methylidene]-2-[4-(3-trifluoromethyl-phenyl)-piperazin-1-yl]-thiazol-4-one;
5-[1-[4-(2,4-Bis-trifluoromethyl-benzyloxy)-3-methoxy-phenyl]-methylidene]-2-(4-phenethyl-piperazin-1-yl)-thiazol-4-one; and
5-[1-[4-(2,4-bis-trifluoromethyl-benzyloxy)-3-methoxy-phenyl]-methylidene]-2-(4-thiophen-3-ylmethyl-piperazin-1-yl)-thiazol-4-one; and
5-[1-[4-(2,4-bis-trifluoromethyl-benzyloxy)-3-methoxy-phenyl]-methylidene]-2-[4-(3-methyl-pyridin-2-ylmethyl)-piperazin-1-yl]-thiazol-4-one;

as a single stereoisomer, a mixture of stereoisomers, or as a racemic mixture of stereoisomers; as any tautomeric form; or as a pharmaceutically acceptable salt thereof.

41. The compound of claim 30 wherein $R^5$ is selected from the group consisting of —C(O)$R^{10}$, —C(O)O$R^{10}$, —C(O)N($R^{11}$)($R^{12}$), —C(S)N($R^{11}$)($R^{12}$) and —S(O)$_2R^{13}$;

where $R^{10}$, $R^{11}$, $R^{12}$ and $R^{13}$ are as described in claim 1.

42. The compound of claim 41 wherein said compound is selected from the group consisting of:
- 5-[1-[4-(2,4-bis-trifluoromethyl-benzyloxy)-3-methoxy-phenyl]-methylidene]-2-[4-(furan-2-carbonyl)-piper-azin-1-yl]-thiazol-4-one;
- 2-(4-acetyl-piperazin-1-yl)-5-[1-[4-(2,4-bis-trifluoromethyl-benzyloxy)-3-methoxy-phenyl]-methylidene]-thiazol-4-one;
- 5-[1-[4-(2,4-bis-trifluoromethyl-benzyloxy)-3-methoxy-phenyl]-methylidene]-2-(4-methanesulfonyl-piper-azin-1-yl)-thiazol-4-one;
- 5-[1-[4-(2,4-bis-trifluoromethyl-benzyloxy)-3-methoxy-phenyl]-methylidene]-2-[4-(tetrahydro-furan-2-carbo-nyl)-piperazin-1-yl]-thiazol-4-one;
- 5-[1-[4-(2,4-bis-trifluoromethyl-benzyloxy)-3-methoxy-phenyl]-methylidene]-2-[4-(2-oxo-2-pyrrolidin-1-yl-ethyl)-piperazin-1-yl]-thiazol-4-one;
- 5-[1-[4-(2,4-bis-trifluoromethyl-benzyloxy)-3-methoxy-phenyl]-methylidene]-2-[4-(2-morpholin-4-yl-2-oxo-ethyl)-piperazin-1-yl]-thiazol-4-one;
- 2-(4-{5-[1-[4-(2,4-bis-trifluoromethyl-benzyloxy)-3-methoxy-phenyl]-methylidene]-4-oxo-4,5-dihydro-thiazol-2-yl}-piperazin-1-yl)-N-methyl-N-phenyl-ac-etamide;
- 4-{5-[1-[4-(2,4-bis-trifluoromethyl-benzyloxy)-3-meth-oxy-phenyl]-methylidene]-4-oxo-4,5-dihydro-thiazol-2-yl}-piperazine-1-carboxylic acid tert-butyl ester;
- 4-{5-[1-[4-(2,4-bis-trifluoromethyl-benzyloxy)-3-meth-oxy-phenyl]-methylidene]-4-oxo-4,5-dihydro-thiazol-2-yl}-piperazine-1-carboxylic acid ethyl ester;
- 4-{5-[1-[4-(2,4-Bis-trifluoromethyl-benzyloxy)-3-meth-oxy-phenyl]-methylidene]-4-oxo-4,5-dihydro-thiazol-2-yl}-piperazine-1-carbothioic acid (4-methoxy-phe-nyl)-amide;
- 4-{5-[1-[4-(2,4-bis-trifluoromethyl-benzyloxy)-3-meth-oxy-phenyl]-methylidene]-4-oxo-4,5-dihydro-thiazol-2-yl}-piperazine-1-carbothioic acid phenethyl-amide; and
- 5-[(4-{5-[1-[4-(2,4-bis-trifluoromethyl-benzyloxy)-3-methoxy-phenyl]-methylidene]-4-oxo-4,5-dihydro-thiazol-2-yl}-piperazine-1-carbothioyl)-amino]-2-(6-hydroxy-3-oxo-3H-xanthen-9-yl)-benzoic acid;

as a single stereoisomer, a mixture of stereoisomers, or as a racemic mixture of stereoisomers; as any tautomeric form; or as a pharmaceutically acceptable salt thereof.

43. The compound of claim 19 wherein said optionally substituted heterocyclyl formed by $R^1$ and $R^2$ is unsubstituted morpholine; or substituted morpholine having the structure:

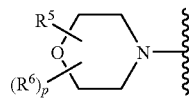

wherein p is an integer from 0 to 7 and $R^5$ and $R^6$ are as described in claim 1.

44. The compound of claim 43 wherein $R^5$ and each $R^6$ are independently selected from the group consisting of halo, cyano, nitro, —$R^9$—O$R^{10}$, —$R^9$—N($R^{11}$)($R^{12}$) and —$R^9$—S$R^{10}$;

where $R^9$, $R^{10}$, $R^{11}$ and $R^{12}$ are as described in claim 1.

45. The compound of claim 43 selected from the group consisting of:
- 5-[1-[4-(2,4-bis-trifluoromethyl-benzyloxy)-3-methoxy-phenyl]-methylidene]-2-morpholin-4-yl-thiazol-4-one;
- 5-[1-[4-(2,4-bis-trifluoromethyl-benzyloxy)-3-methoxy-phenyl]-methylidene]-2-(3,5-dimethyl-morpholin-4-yl)-thiazol-4-one;
- 5-[1-[4-(2,4-bis-trifluoromethyl-benzyloxy)-3-methoxy-phenyl]-methylidene]-2-(2,6-dimethyl-morpholin-4-yl)-thiazol-4-one;
- 5-[1-[4-(2,4-bis-trifluoromethyl-benzyloxy)-3-methoxy-phenyl]-methylidene]-2-morpholin-4-yl-thiazol-4-one;

as a single stereoisomer, a mixture of stereoisomers, or as a racemic mixture of stereoisomers; as any tautomeric form; or as a pharmaceutically acceptable salt thereof.

46. The compound of claim 19 wherein said optionally substituted heterocyclyl formed by $R^1$ and $R^2$ is unsubstituted thiomorpholine; or substituted thiomorpholine having the structure:

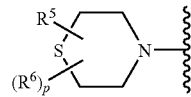

wherein p is an integer from 0 to 7 and $R^5$ and $R^6$ are as described in claim 1.

47. The compound of claim 46 wherein $R^5$ and each $R^6$ are independently selected from the group consisting of halo, cyano, nitro, optionally substituted alkyl, —$R^9$—O$R^{10}$, —$R^9$—N($R^{11}$)($R^{12}$), and —$R^9$—S$R^{10}$;

where $R^9$, $R^{10}$, $R^{11}$ and $R^{12}$ are as described in claim 1.

48. The compound of claim 46 selected from the group consisting of:
- 5-[1-[4-(2,4-bis-trifluoromethyl-benzyloxy)-3-methoxy-phenyl]-methylidene]-2-thiomorpholin-4-yl-thiazol-4-one; and
- 5-[1-[4-(2,4-bis-trifluoromethyl-benzyloxy)-3-methoxy-phenyl]-methylidene]-2-thiomorpholin-4-yl-thiazol-4-one;

as a single stereoisomer, a mixture of stereoisomers, or as a racemic mixture of stereoisomers; as any tautomeric form; or as a pharmaceutically acceptable salt thereof.

49. The compound of claim 19 wherein said optionally substituted heterocyclyl formed by $R^1$ and $R^2$ is unsubstituted azepine; or optionally substituted azepine having the structure:

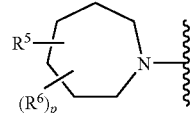

wherein p is an integer from 0 to 11 and $R^5$ and $R^6$ are as described in claim 1.

50. The compound of claim 49 wherein $R^5$ and $R^6$ are each independently selected from halo, cyano, nitro, optionally substituted alkyl, optionally substituted aryl, optionally substituted heteroaryl, —$R^9$—O$R^{10}$, —$R^9$—N($R^{11}$)($R^{12}$) and —$R^9$—S$R^{10}$;

wherein $R^9$, $R^{10}$, $R^{11}$ and $R^{12}$ are as described in claim 1.

51. The compound of claim 50 wherein said compound is 5-[1-[4-(2,4-bis-trifluoromethyl-benzyloxy)-3-methoxy-phenyl]-methylidene]-2-(2-pyridin-2-yl-azepan-1-yl)-thiazol-4-one;
as a single stereoisomer, a mixture of stereoisomers, or as a racemic mixture of stereoisomers; as any tautomeric form; or as a pharmaceutically acceptable salt thereof.

52. The compound of claim 19 wherein said optionally substituted heterocyclyl formed by $R^1$ and $R^2$ is optionally substituted diazepine.

53. The compound of claim 52 wherein said diazepine is unsubstituted diazepine; or substituted diazepine having the structure:

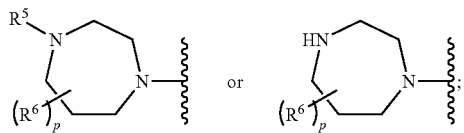

wherein p is an integer from 0 to 10 and $R^5$ and $R^6$ are as described in claim 1.

54. The compound of claim 53 wherein $R^5$ and $R^6$ are each independently selected from halo, cyano, nitro, optionally substituted alkyl, optionally substituted heterocyclyl, optionally substituted aryl, optionally substituted heteroaryl, —$R^9$—$OR^{10}$, —$R^9$—$N(R^{11})(R^{12})$, —$R^9$—$SR^{10}$, —$R^9$—C(J)$R^{10}$, —$R^9$—C(J)$OR^{10}$, —$R^9$—C(J)N($R^{11}$)($R^{12}$) and —$R^9$—S(O)$_r R^{13}$;
wherein $R^9$, $R^{10}$, $R^{11}$ and $R^{12}$ are as described in claim 1.

55. The compound of claim 52 selected from the group consisting of:
5-[1-[4-(2,4-bis-trifluoromethyl-benzyloxy)-3-methoxy-phenyl]-methylidene]-2-(4-pyrimidin-2-yl-[1,4]diazepan-1-yl)-thiazol-4-one; and
2-(4-benzooxazol-2-yl-[1,4]diazepan-1-yl)-5-[1-[4-(2,4-bis-trifluoromethyl-benzyloxy)-3-methoxy-phenyl]-methylidene]-thiazol-4-one;
as a single stereoisomer, a mixture of stereoisomers, or as a racemic mixture of stereoisomers; as any tautomeric form; or as a pharmaceutically acceptable salt thereof.

56. The compound of claim 19 wherein said optionally substituted heterocyclyl is bicyclic piperidine optionally substituted with $R^5$ and $R^6$ or bicyclic piperazine optionally substituted with $R^5$ and $R^6$.

57. The compound of claim 56 selected from the group consisting of:
5-[1-[4-(2,4-bis-trifluoromethyl-benzyloxy)-3-methoxy-phenyl]-methylidene]-2-(octahydro-quinolin-1-yl)-thiazol-4-one;
5-[1-[4-(2,4-bis-trifluoromethyl-benzyloxy)-3-methoxy-phenyl]-methylidene]-2-(octahydro-isoquinolin-2-yl)-thiazol-4-one;
5-[1-[4-(2,4-bis-trifluoromethyl-benzyloxy)-3-methoxy-phenyl]-methylidene]-2-(1-methyl-3,4-dihydro-1H-pyrrolo[1,2-a]pyrazin-2-yl)-thiazol-4-one;
as a single stereoisomer, a mixture of stereoisomers, or as a racemic mixture of stereoisomers; as any tautomeric form; or as a pharmaceutically acceptable salt thereof.

58. The compound of claim 1 where bond q is a single bond.

59. The compound of claim 58 wherein:
X is —O—;
L is methylene and
Y is a direct bond.

60. The compound of claim 58 wherein said compound is 5-[4-(2,4-bis-trifluoromethyl-benzyloxy)-3-methoxy-benzyl]-2-(4-methyl-piperazin-1-yl)-thiazol-4-one, as a single stereoisomer, a mixture of stereoisomers, or as a racemic mixture of stereoisomers; as any tautomeric form; or as a pharmaceutically acceptable salt thereof.

61. A compound according to claim 1 selected from which is 3-{5-[1-[4-(2,4-Bis-trifluoromethyl-benzyloxy)-3-methoxy-phenyl]-meth-(E)-ylidene]-4-oxo-4,5-dihydro-thiazol-2-ylamino}-benzoic acid ethyl ester, as a single stereoisomer, a mixture of stereoisomers, or as a racemic mixture of stereoisomers; as any tautomeric form; or as a pharmaceutically acceptable salt thereof.

* * * * *

UNITED STATES PATENT AND TRADEMARK OFFICE
CERTIFICATE OF CORRECTION

| | | |
|---|---|---|
| PATENT NO. | : 7,977,489 B2 | Page 1 of 1 |
| APPLICATION NO. | : 11/577611 | |
| DATED | : July 12, 2011 | |
| INVENTOR(S) | : Martin et al. | |

It is certified that error appears in the above-identified patent and that said Letters Patent is hereby corrected as shown below:

At Column 65, line 43, replace "A is 2,4-bis-trifluorophenyl;" with -- A is 2,4-bis-trifluoromethylphenyl; --

At Column 69, line 18, replace "A is -2,4-bis-trifluorophenyl." with -- A is 2,4-bis-trifluoromethylphenyl. --

At Column 69, lines 43-44, replace "A -2,4-bis-trifluorophenyl." with -- A is 2,4-bis-trifluoromethylphenyl. --

Signed and Sealed this
Tenth Day of January, 2012

David J. Kappos
*Director of the United States Patent and Trademark Office*